US007005291B1

(12) United States Patent
Nair et al.

(10) Patent No.: US 7,005,291 B1
(45) Date of Patent: Feb. 28, 2006

(54) TRANSFORMED MICROORGANISMS AND GENES USEFUL IN THE PRODUCTION OF GLYCEROL AND 1,3-PROPANEDIOL

(75) Inventors: Ramesh V. Nair, Wilmington, DE (US); Mark S. Payne, Wilmington, DE (US); Donald E. Trimbur, Redwood City, CA (US); Fernando Valle, Burlingame, CA (US)

(73) Assignees: E. I. du Pont de Nemours and Company, Wilmington, DE (US); Genencor International, Palo Alto, CA (US)

( * ) Notice: Subject to any disclaimer, the term of this patent is extended or adjusted under 35 U.S.C. 154(b) by 638 days.

(21) Appl. No.: 09/695,786

(22) Filed: Oct. 25, 2000

Related U.S. Application Data

(62) Division of application No. 08/982,783, filed on Dec. 2, 1997, now abandoned.

(51) Int. Cl.
*C12N 1/00* (2006.01)
*C12N 1/21* (2006.01)
*C12N 9/04* (2006.01)
*C12N 9/12* (2006.01)
*C12N 15/52* (2006.01)

(52) U.S. Cl. .............................. 435/252.3; 435/252.33; 435/254.11; 435/190; 435/194; 536/23.2

(58) Field of Classification Search ................ 435/159, 435/252.3, 252.33, 254.11, 194, 190, 325, 435/410; 536/23.2
See application file for complete search history.

(56) References Cited

U.S. PATENT DOCUMENTS 6,358,716 B1 * 3/2002 Bulthuis et al. ............. 435/159
6,514,733 B1 * 2/2003 Laffend et al. ............. 435/158

FOREIGN PATENT DOCUMENTS

| FR | 2 725 145 A1 | 12/1996 |
|---|---|---|
| WO | WO96 35795 | 11/1996 |
| WO | WO96 35796 | 11/1996 |
| WO | WO96 35799 | 11/1996 |
| WO | WO96 41888 | 12/1996 |
| WO | WO 97 07199 A1 | 2/1997 |
| WO | WO98 21339 | 5/1998 |
| WO | WO 98 21340 A1 | 5/1998 |
| WO | WO98 21341 | 5/1998 |

OTHER PUBLICATIONS

Ben-Amotz et al., Experientia, 38, 49-52, 1982.
Albertyn et al., Mol. Cell. Biol., 14, 4135-4144, 1994.
Wang et al., J. Bact. , 176, 7091-7095, 1994.
Hirayama et al., "Cloning and characterization of seven cDNAs for hyperosmolarity-responsive (HOR) genes of Saccharomyces", *Mol. Gen. Genet,* 249, 127-138, 1995.
Omori et al., Breeding of High Glycerol-Producing Shochu Yeast (*Sacchromyces cerevisiae*) with Acquired Salt Tolerance, *Journal of Fermentation and Bioengineering*, 79, 560-565, 1995.
Larason et al., Mol. Microbiol., 10, 1101, 1993.
Eustace, R. et al., Department of Micrbiology and Genetics, Selective hybridization and wine yeasts for higher yields of glycerol.
Norbeck et al., J. Biol. Chem., 271, 13875; 1996.
Can. J. Microbiol., 33:112-117, 1987.

* cited by examiner

*Primary Examiner*—Gabriele E Bugaisky

(57) ABSTRACT

Recombinant organisms are provided comprising genes encoding a glycerol-3-phosphate dehydrogenase and/or a glycerol-3-phosphatase activity useful for the production of glycerol from a variety of carbon substrates. The organisms further contain disruptions in the endogenous genes encoding proteins having glycerol kinase and glycerol dehydrogenase activities.

7 Claims, 1 Drawing Sheet

Figure 1:
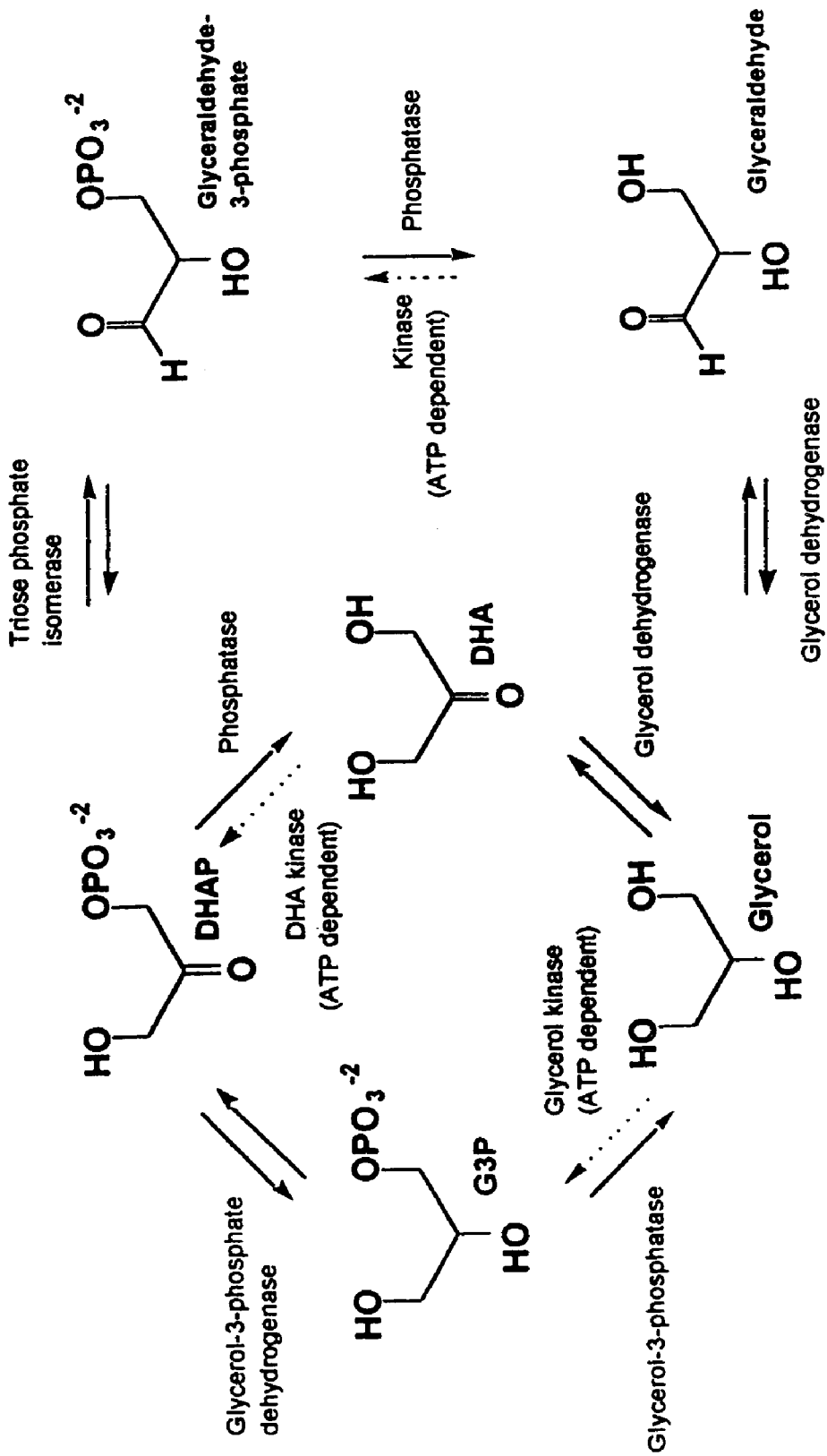

TRANSFORMED MICROORGANISMS AND GENES USEFUL IN THE PRODUCTION OF GLYCEROL AND 1,3-PROPANEDIOL

This application is a division of U.S. application Ser. No. 08/982,783 filed 2 Dec. 1997 (now abandoned).

FIELD OF INVENTION

The present invention relates to the field of molecular biology and the use of recombinant organisms for the production of glycerol and compounds derived from the glycerol biosynthetic pathway. More specifically the invention describes the construction of a recombinant cell for the production of glycerol and derived compounds from a carbon substrate, the cell containing foreign genes encoding proteins having glycerol-3-phosphate dehydrogenase (G3PDH) and glycerol-3-phosphatase (G3P phosphatase) activities where the endogenous genes encoding the glycerol-converting glycerol kinase and glycerol dehydrogenase activities have been deleted.

BACKGROUND

Glycerol is a compound in great demand by industry for use in cosmetics, liquid soaps, food, pharmaceuticals, lubricants, anti-freeze solutions, and in numerous other applications. The esters of glycerol are important in the fat and oil industry. Historically, glycerol has been isolated from animal fat and similar sources; however, the process is laborious and inefficient. Microbial production of glycerol is preferred.

Not all organisms have a natural capacity to synthesize glycerol. However, the biological production of glycerol is known for some species of bacteria, algae, and yeast. The bacteria *Bacillus licheniformis* and *Lactobacillus lycopersica* synthesize glycerol. Glycerol production is found in the halotolerant algae *Dunaliella* sp. and *Asteromonas gracilis* for protection against high external salt concentrations (Ben-Amotz et al., (1982) *Experientia* 38:49–52). Similarly, various osmotolerant yeast synthesize glycerol as a protective measure. Most strains of *Saccharomyces* produce some glycerol during alcoholic fermentation and this production can be increased by the application of osmotic stress (Albertyn et al., (1994) *Mol. Cell. Biol.* 14, 4135–4144). Earlier this century glycerol was produced commercially with *Saccharomyces* cultures to which steering reagents were added such as sulfites or alkalis. Through the formation of an inactive complex, the steering agents block or inhibit the conversion of acetaldehyde to ethanol; thus, excess reducing equivalents (NADH) are available to or "steered" towards dihydroxyacetone phosphate (DHAP) for reduction to produce glycerol. This method is limited by the partial inhibition of yeast growth that is due to the sulfites. This limitation can be partially overcome by the use of alkalis which create excess NADH equivalents by a different mechanism. In this practice, the alkalis initiated a Cannizarro disproportionation to yield ethanol and acetic acid from two equivalents of acetaldehyde. Thus, although production of glycerol is possible from naturally occurring organisms, production is often subject to the need to control osmotic stress of the cultures and the production of sulfites. A method free from these limitations is desirable. Production of glycerol from recombinant organisms containing foreign genes encoding key steps in the glycerol biosynthetic pathway is one possible route to such a method.

A number of the genes involved in the glycerol biosynthetic pathway have been isolated. For example, the gene encoding glycerol-3-phosphate dehydrogenase (DAR1, GPD1) has been cloned and sequenced from *Saccharomyces diastaticus* (Wang et al., (1994), *J. Bact.* 176:7091–7095). The DAR1 gene was cloned into a shuttle vector and used to transform *E. coli* where expression produced active enzyme. Wang et al., supra, recognizes that DAR1 is regulated by the cellular osmotic environment but does not suggest how the gene might be used to enhance glycerol production in a recombinant organism.

Other glycerol-3-phosphate dehydrogenase enzymes have been isolated. For example, sn-glycerol-3-phosphate dehydrogenase has been cloned and sequenced from *S. cerevisiae* (Larason et al., (1993) Mol. Microbiol., 10:1101). Albertyn et al., (1994) *Mol. Cell. Biol.*, 14:4135) teach the cloning of GPD1 encoding a glycerol-3-phosphate dehydrogenase from *S. cerevisiae*. Like Wang et al., both Albertyn et al. and Larason et al. recognize the osmo-sensitvity of the regulation of this gene but do not suggest how the gene might be used in the production of glycerol in a recombinant organism.

As with G3PDH, glycerol-3-phosphatase has been isolated from *Saccharomyces cerevisiae* and the protein identified as being encoded by the GPP1 and GPP2 genes (Norbeck et al., (1996) *J. Biol. Chem.*, 271:13875). Like the genes encoding G3PDH, it appears that GPP2 is osmotically-induced.

Although the genes encoding G3PDH and G3P phosphatase have been isolated, there is no teaching in the art that demonstrates glycerol production from recombinant organisms with G3PDH/G3P phosphatase expressed together or separately. Further, there is no teaching to suggest that efficient glycerol production from any wild-type organism is possible using these two enzyme activities that does not require applying some stress (salt or an osmolyte) to the cell. In fact, the art suggests that G3PDH activities may not affect glycerol production. For example, Eustace ((1987), *Can. J. Microbiol.*, 33:112–117)) teaches hybridized yeast strains that produced glycerol at greater levels than the parent strains. However, Eustace also demonstrates that G3PDH activity remained constant or slightly lower in the hybridized strains as opposed to the wild type.

Glycerol is an industrially useful material. However, other compounds may be derived from the glycerol biosynthetic pathway that also have commercial significance. For example, glycerol-producing organisms may be engineered to produce 1,3-propanediol (U.S. Pat. No. 5,686,276), a monomer having potential utility in the production of polyester fibers and the manufacture of polyurethanes and cyclic compounds. It is known for example that in some organisms, glycerol is converted to 3-hydroxypropionaldehyde and then to 1,3-propanediol through the actions of a dehydratase enzyme and an oxidoreductase enzyme, respectively. Bacterial strains able to produce 1,3-propanediol have been found, for example, in the groups *Citrobacter, Clostridium, Enterobacter, Ilyobacter, Klebsiella, Lactobacillus*, and *Pelobacter*. Glycerol dehydratase and diol dehydratase systems are described by Seyfried et al. (1996)*J. Bacteriol.* 178:5793–5796 and Tobimatsu et al. (1995) *J. Biol. Chem.* 270:7142–7148, respectively. Recombinant organisms, containing exogenous dehydratase enzyme, that are able to produce 1,3-propanediol have been described (U.S. Pat. No. 5,686,276). Although these organisms produce 1,3-propanediol, it is clear that they would benefit from a system that would minimize glycerol conversion.

There are a number of advantages in engineering a glycerol-producing organism for the production of 1,3-propanediol where conversion of glycerol is minimized. A microorganism capable of efficiently producing glycerol under physiological conditions is industrially desirable, especially when the glycerol itself will be used as a substrate in vivo as part of a more complex catabolic or biosynthetic pathway that could be perturbed by osmotic stress or the addition of steering agents (e.g., the production of 1,3-propanediol). Some attempts at creating glycerol kinase and glycerol dehydrogenase mutants have been made. For example, De Koning et al. (1990)*Appl. Microbiol Biotechnol.* 32:693–698 report the methanol-dependent production of dihydroxyacetone and glycerol by mutants of the methylotrophic yeast *Hansenula polymorpha* blocked in dihydroxyacetone kinase and glycerol kinase. Methanol and an additional substrate, required to replenish the xyulose-5-phosphate co-substrate of the assimilation reaction, were used to produce glycerol; however, a dihydroxyacetone reductase (glycerol dehydrogenase) is also required. Similarly, Shaw and Cameron, Book of Abstracts, 211th ACS National Meeting, New Orleans, La., Mar. 24–28 (1996), BIOT-154 Publisher: American Chemical Society, Washington, D.C., investigate the deletion of of ldhA (lactate dehydrogenase), glpK (glycerol kinase), and tpiA (triosephosphate isomerase) for the optimization of 1,3-propanediol production. They do not suggest the expression of cloned genes for G3PDH or G3P phosphatase for the production of glycerol or 1,3-propanediol and they do not discuss the impact of glycerol dehydrogenase.

The problem to be solved, therefore, is the lack of a process to direct carbon flux towards glycerol production by the addition or enhancement of certain enzyme activities, especially G3PDH and G3P phosphatase which respectively catalyze the conversion of dihydroxyacetone phosphate (DHAP) to glycerol-3-phosphate (G3P) and then to glycerol. The problem is complicated by the need to control the carbon flux away from glycerol by deletion or decrease of certain enzyme activities, especially glycerol kinase and glycerol dehydrogenase which respectively catalyze the conversion of glycerol plus ATP to G3P and glycerol to dihydroxyacetone (or glyceraldehyde).

SUMMARY OF THE INVENTION

The present invention provides a method for the production of glycerol from a recombinant organism comprising: transforming a suitable host cell with an expression cassette comprising either one or both of (a) a gene encoding a protein having glycerol-3-phosphate dehydrogenase activity and (b) a gene encoding a protein having glycerol-3-phosphate phosphatase activity, where the suitable host cell contains a disruption in either one or both of (a) a gene encoding an endogenous glycerol kinase and (b) a gene encoding an endogenous glycerol dehydrogenase, wherein the disruption prevents the expression of active gene product; culturing the transformed host cell in the presence of at least one carbon source selected from the group consisting of monosaccharides, oligosaccharides, polysaccharides, and single-carbon substrates, whereby glycerol is produced; and recovering the glycerol produced.

The present invention further provides a process for the production of 1,3-propanediol from a recombinant organism comprising: transforming a suitable host cell with an expression cassette comprising either one or both of (a) a gene encoding a protein having glycerol-3-phosphate dehydrogenase activity and (b) a gene encoding a protein having glycerol-3-phosphate phosphatase activity, the suitable host cell having at least one gene encoding a protein having a dehydratase activity and having a disruption in either one or both of (a) a gene encoding an endogenous glycerol kinase and (b) a gene encoding an endogenous glycerol dehydrogenase, wherein the disruption in the genes of (a) or (b) prevents the expression of active gene product; culturing the transformed host cell in the presence of at least one carbon source selected from the group consisting of monosaccharides, oligosaccharides, polysaccharides, and single-carbon substrates whereby 1,3-propanediol is produced; and recovering the 1,3-propanediol produced.

Additionally, the invention provides for a process for the production of 1,3-propanediol from a recombinant organism where multiple copies of endogeneous genes are introduced.

Further embodiments of the invention include host cells transformed with heterologous genes for the glycerol pathway as well as host cells which contain endogeneous genes for the glycerol pathway.

Additionally, the invention provides recombinant cells suitable for the production either glycerol or 1,3-propanediol, the host cells having genes expressing either one or both of a glycerol-3-phosphate dehydrogenase activity and a glycerol-3-phosphate phosphatase activity wherein the cell also has disruptions in either one or both of a gene encoding an endogenous glycerol kinase and a gene encoding an endogenous glycerol dehydrogenase, wherein the disruption in the genes prevents the expression of active gene product.

BRIEF DESCRIPTION OF THE FIGURES, BIOLOGICAL DEPOSITS AND SEQUENCE LISTING

FIG. 1 illustrates the representative enzymatic pathways involving glycerol metabolism.

Applicants have made the following biological deposits under the terms of the Budapest Treaty on the International Recognition of the Deposit of Micro-organisms for the Purposes of Patent Procedure:

| Depositor Identification Reference | Int'l. Depository Designation | Date of Deposit |
| --- | --- | --- |
| *Escherichia coli* pAH2L/DH5α (containing the GPP2 gene) | ATCC 98187 | Sep. 26, 1996 |
| *Escherichia coli* (pDAR1A/AA200) (containing the DAR1 gene) | ATCC 98248 | Nov. 6, 1996 |
| FM5 *Escherichia coli* RJF10m (containing a glpK disruption) | ATCC 98597 | Nov. 25, 1997 |
| FM5 *Escherichia coli* MSP33.6 (containing a gldA disruption) | ATCC 98598 | Nov. 25, 1997 |

"ATCC" refers to the American Type Culture Collection international depository located at 10801 University Blvd. Manassas, Va. 20110-2209 U.S.A. The designation is the accession number of the deposited material.

Applicants have provided 43 sequences in conformity with the Rules for the Standard Representation of Nucleotide and Amino Acid Sequences in Patent Applications (Annexes I and II to the Decision of the President of the EPO, published in Supplement No. 2 to OJ EPO, 12/1992) and with 37 C.F.R. 1.821–1.825 and Appendices A and B (Requirements for Application Disclosures Containing Nucleotides and/or Amino Acid Sequences).

DETAILED DESCRIPTION OF THE INVENTION

The present invention solves the problem stated above by providing a method for the biological production of glycerol from a fermentable carbon source in a recombinant organism. The method provides a rapid, inexpensive and environmentally-responsible source of glycerol useful in the cosmetics and pharmaceutical industries. The method uses a microorganism containing cloned homologous or heterologous genes encoding glycerol-3-phosphate dehydrogenase (G3PDH) and/or glycerol-3-phosphatase (G3P phosphatase). These genes are expressed in a recombinant host having disruptions in genes encoding endogenous glycerol kinase and/or glycerol dehydrogenase enzymes. The method is useful for the production of glycerol, as well as any end products for which glycerol is an intermediate. The recombinant microorganism is contacted with a carbon source and cultured and then glycerol or any end products derived therefrom are isolated from the conditioned media. The genes may be incorporated into the host microorganism separately or together for the production of glycerol.

Applicants' process has not previously been described for a recombinant organism and required the isolation of genes encoding the two enzymes and their subsequent expression in a host cell having disruptions in the endogenous kinase and dehydrogenase genes. It will be appreciated by those familiar with this art that Applicants' process may be generally applied to the production compounds where glycerol is a key intermediate, e.g., 1,3-propanediol.

As used herein the following terms may be used for interpretation of the claims and specification.

The terms "glycerol-3-phosphate dehydrogenase" and "G3PDH" refer to a polypeptide responsible for an enzyme activity that catalyzes the conversion of dihydroxyacetone phosphate (DHAP) to glycerol-3-phosphate (G3P). In vivo G3PDH may be NADH; NADPH; or FAD-dependent. The NADH-dependent enzyme (EC 1.1.1.8) is encoded, for example, by several genes including GPD1 (GenBank Z74071x2), or GPD2 (GenBank Z35169x1), or GPD3 (GenBank G984182), or DAR1 (GenBank Z74071x2). The NADPH-dependent enzyme (EC 1.1.1.94) is encoded by gpsA (GenBank U321643, (cds 197911–196892) G466746 and L45246). The FAD-dependent enzyme (EC 1.1.99.5) is encoded by GUT2 (GenBank Z47047x23), or glpD (GenBank G147838), or glpABC (GenBank M20938).

The terms "glycerol-3-phosphatase", "sn-glycerol-3-phosphatase", or "d,l-glycerol phosphatase", and "G3P phosphatase" refer to a polypeptide responsible for an enzyme activity that catalyzes the conversion of glycerol-3-phosphate and water to glycerol and inorganic phosphate. G3P phosphatase is encoded, for example, by GPP1 (GenBank Z47047x125), or GPP2 (GenBank U18813x11).

The term "glycerol kinase" refers to a polypeptide responsible for an enzyme activity that catalyzes the conversion of glycerol and ATP to glycerol-3-phosphate and ADP. The high energy phosphate donor ATP may be replaced by physiological substitutes (e.g. phosphoenolpyruvate). Glycerol kinase is encoded, for example, by GUT1 (GenBank U1 1583x19) and glpK (GenBank L19201).

The term "glycerol dehydrogenase" refers to a polypeptide responsible for an enzyme activity that catalyzes the conversion of glycerol to dihydroxyacetone (E.C. 1.1.1.6) or glycerol to glyceraldehyde (E.C. 1.1.1.72). A polypeptide responsible for an enzyme activity that catalyzes the conversion of glycerol to dihydroxyacetone is also referred to as a "dihydroxyacetone reductase". Glycerol dehydrogenase may be dependent upon NADH (E.C. 1.1.1.6), NADPH (E.C. 1.1.1.72), or other cofactors (e.g., E.C. 1.1.99.22). A NADH-dependent glycerol dehydrogenase is encoded, for example, by gldA (GenBank U00006).

The term "dehydratase enzyme" will refer to any enzyme that is capable of isomerizing or converting a glycerol molecule to the product 3-hydroxypropion-aldehyde. For the purposes of the present invention the dehydratase enzymes include a glycerol dehydratase (E.C. 4.2.1.30) and a diol dehydratase (E.C. 4.2.1.28) having preferred substrates of glycerol and 1,2-propanediol, respectively. In *Citrobacter freundii*, for example, glycerol dehydratase is encoded by three polypeptides whose gene sequences are represented by dhaB, dhaC and dhaE (GenBank U09771: base pairs 8556–10223, 10235–10819, and 10822–11250, respectively). In *Klebsiella oxytoca*, for example, diol dehydratase is encoded by three polypeptides whose gene sequences are represented by pddA, pddB, and pddC (GenBank D45071: base pairs 121–1785, 1796–2470, and 2485–3006, respectively).

The terms "GPD1", "DAR1", "OSG1", "D2830", and "YDL022W" will be used interchangeably and refer to a gene that encodes a cytosolic glycerol-3-phosphate dehydrogenase and is characterized by the base sequence given as SEQ ID NO:1.

The term "GPD2" refers to a gene that encodes a cytosolic glycerol-3-phosphate dehydrogenase and is characterized by the base sequence given in SEQ ID NO:2.

The terms "GUT2" and "YIL155C" are used interchangeably and refer to a gene that encodes a mitochondrial glycerol-3-phosphate dehydrogenase and is characterized by the base sequence given in SEQ ID NO:3.

The terms "GPP1", "RHR2" and "YIL053W" are used interchangeably and refer to a gene that encodes a cytosolic glycerol-3-phosphatase and is characterized by the base sequence given in SEQ ID NO:4.

The terms "GPP2", "HOR2" and "YER062C" are used interchangeably and refer to a gene that encodes a cytosolic glycerol-3-phosphatase and is characterized by the base sequence given as SEQ ID NO:5.

The term "GUT1" refers to a gene that encodes a cytosolic glycerol kinase and is characterized by the base sequence given as SEQ ID NO:6. The term "glpK" refers to another gene that encodes a glycerol kinase and is characterized by the base sequence given in GeneBank L19201, base pairs 77347–78855.

The term "gldA" refers to a gene that encodes a glycerol dehydrogenase and is characterized by the base sequence given in GeneBank U00006, base pairs 3174–4316. The term "dhaD" refers to another gene that encodes a glycerol dehydrogenase and is characterized by the base sequence given in GeneBank U09771, base pairs 2557–3654.

As used herein, the terms "function" and "enzyme function" refer to the catalytic activity of an enzyme in altering the energy required to perform a specific chemical reaction. Such an activity may apply to a reaction in equilibrium where the production of both product and substrate may be accomplished under suitable conditions.

The terms "polypeptide" and "protein" are used interchangeably.

The terms "carbon substrate" and "carbon source" refer to a carbon source capable of being metabolized by host organisms of the present invention and particularly mean carbon sources selected from the group consisting of monosaccharides, oligosaccharides, polysaccharides, and one-carbon substrates or mixtures thereof.

"Conversion" refers to the metabolic processes of an organism or cell that by means of a chemical reaction degrades or alters the complexity of a chemical compound or substrate.

The terms "host cell" and "host organism" refer to a microorganism capable of receiving foreign or heterologous genes and additional copies of endogeneous genes and expressing those genes to produce an active gene product.

The terms "production cell" and "production organism" refer to a cell engineered for the production of glycerol or compounds that may be derived from the glycerol biosynthetic pathway. The production cell will be recombinant and contain either one or both of a gene that encodes a protein having a glycerol-3-phosphate dehydrogenase activity and a gene encoding a protein having a glycerol-3-phosphatase activity. In addition to the G3PDH and G3P phosphatase genes, the host cell will contain disruptions in one or both of a gene encoding an endogenous glycerol kinase and a gene encoding an endogenous glycerol dehydrogenase. Where the production cell is designed to produce 1,3-propanediol, it will additionally contain a gene encoding a protein having a dehydratase activity.

The terms "foreign gene", "foreign DNA", "heterologous gene", and "heterologous DNA" all refer to genetic material native to one organism that has been placed within a different host organism.

The term "endogenous" as used herein with reference to genes or polypeptides expressed by genes, refers to genes or polypeptides that are native to a production cell and are not derived from another organism. Thus an "endogenous glycerol kinase" and an "endogenous glycerol dehydrogenase" are terms referring to polypeptides encoded by genes native to the production cell.

The terms "recombinant organism" and "transformed host" refer to any organism transformed with heterologous or foreign genes. The recombinant organisms of the present invention express foreign genes encoding G3PDH and G3P phosphatase for the production of glycerol from suitable carbon substrates. Additionally, the terms "recombinant organism" and "transformed host" refer to any organism transformed with endogenous (or homologous) genes so as to increase the copy number of the genes.

"Gene" refers to a nucleic acid fragment that expresses a specific protein, including regulatory sequences preceding (5' non-coding) and following (3' non-coding) the coding region. The terms "native" and "wild-type" gene refer to the gene as found in nature with its own regulatory sequences.

The terms "encoding" and "coding" refer to the process by which a gene, through the mechanisms of transcription and translation, produces an amino acid sequence. The process of encoding a specific amino acid sequence is meant to include DNA sequences that may involve base changes that do not cause a change in the encoded amino acid, or which involve base changes which may alter one or more amino acids, but do not affect the functional properties of the protein encoded by the DNA sequence. Therefore, the invention encompasses more than the specific exemplary sequences. Modifications to the sequence, such as deletions, insertions, or substitutions in the sequence which produce silent changes that do not substantially affect the functional properties of the resulting protein molecule are also contemplated. For example, alterations in the gene sequence which reflect the degeneracy of the genetic code, or which result in the production of a chemically equivalent amino acid at a given site, are contemplated; thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a biologically equivalent product. Nucleotide changes which result in alteration of the N-terminal and C-terminal portions of the protein molecule would also not be expected to alter the activity of the protein. In some cases, it may in fact be desirable to make mutants of the sequence in order to study the effect of alteration on the biological activity of the protein. Each of the proposed modifications is well within the routine skill in the art, as is determination of retention of biological activity in the encoded products. Moreover, the skilled artisan recognizes that sequences encompassed by this invention are also defined by their ability to hybridize, under stringent conditions (0.1×SSC, 0.1% SDS, 65° C.), with the sequences exemplified herein.

The term "expression" refers to the transcription and translation to gene product from a gene coding for the sequence of the gene product.

The terms "plasmid", "vector", and "cassette" as used herein refer to an extra chromosomal element often carrying genes which are not part of the central metabolism of the cell and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

The terms "transformation" and "transfection" refer to the acquisition of new genes in a cell after the incorporation of nucleic acid. The acquired genes may be integrated into chromosomal DNA or introduced as extrachromosomal replicating sequences. The term "transformant" refers to the cell resulting from a transformation.

The term "genetically altered" refers to the process of changing hereditary material by transformation or mutation. The terms "disruption" and "gene interrupt" as applied to genes refer to a method of genetically altering an organism by adding to or deleting from a gene a significant portion of that gene such that the protein encoded by that gene is either not expressed or not expressed in active form.

Glycerol Biosynthetic Pathway

It is contemplated that glycerol may be produced in recombinant organisms by the manipulation of the glycerol biosynthetic pathway found in most microorganisms. Typically, a carbon substrate such as glucose is converted to glucose-6-phosphate via hexokinase in the presence of ATP. Glucose-phosphate isomerase catalyzes the conversion of glucose-6-phosphate to fructose-6-phosphate and then to fructose-1,6-diphosphate through the action of 6-phosphofructokinase. The diphosphate is then taken to dihydroxyacetone phosphate (DHAP) via aldolase. Finally NADH-dependent G3PDH converts DHAP to glycerol-3-phosphate which is then dephosphorylated to glycerol by G3P phosphatase. (Agarwal (1990), *Adv. Biochem. Engrg.* 41:114).

Genes Encoding G3PDH, glycerol dehydrogenase, G3P Phosphatase and Glycerol Kinase The present invention provides genes suitable for the expression of G3PDH and G3P phosphatase activities in a host cell.

Genes encoding G3PDH are known. For example, GPD1 has been isolated from *Saccharomyces* and has the base sequence given by SEQ ID NO: 1, encoding the amino acid sequence given in SEQ ID NO:7 (Wang et al., supra). Similarly, G3PDH activity has also been isolated from *Saccharomyces* encoded by GPD2 having the base sequence given in SEQ ID NO:2 encoding the amino acid sequence given in SEQ ID NO:8 (Eriksson et al., (1995) *Mol. Microbiol.*, 17:95).

For the purposes of the present invention it is contemplated that any gene encoding a polypeptide responsible for G3PDH activity is suitable wherein that activity is capable of catalyzing the conversion of dihydroxyacetone phosphate (DHAP) to glycerol-3-phosphate (G3P). Further, it is contemplated that any gene encoding the amino acid sequence of G3PDH as given by SEQ ID NOS:7, 8, 9, 10, 11 and 12 corresponding to the genes GPD1, GPD2, GUT2, gpsA, glpD, and the α subunit of glpABC respectively, will be functional in the present invention wherein that amino acid sequence may encompass amino acid substitutions, deletions or additions that do not alter the function of the enzyme. The skilled person will appreciate that genes encoding G3PDH isolated from other sources will also be suitable for use in the present invention. For example, genes isolated from prokaryotes include GenBank accessions M34393, M20938, L06231, U12567, L45246, L45323, L45324, L45325, U32164, U32689, and U39682. Genes isolated from fungi include GenBank accessions U30625, U30876 and X56162; genes isolated from insects include GenBank accessions X61223 and X14179; and genes isolated from mammalian sources include GenBank accessions U12424, M25558 and X78593.

Genes encoding G3P phosphatase are known. For example, GPP2 has been isolated from *Saccharomyces cerevisiae* and has the base sequence given by SEQ ID NO:5, which encodes the amino acid sequence given in SEQ ID NO: 13 (Norbeck et al., (1996), *J. Biol. Chem.*, 271: 13875).

For the purposes of the present invention, any gene encoding a G3P phosphatase activity is suitable for use in the method wherein that activity is capable of catalyzing the conversion of glycerol-3-phosphate and water to glycerol and inorganic phosphate. Further, any gene encoding the amino acid sequence of G3P phosphatase as given by SEQ ID NOS.: 13 and 14 corresponding to the genes GPP2 and GPP1 respectively, will be functional in the present invention including any amino acid sequence that encompasses amino acid substitutions, deletions or additions that do not alter the function of the G3P phosphatase enzyme. The skilled person will appreciate that genes encoding G3P phosphatase isolated from other sources will also be suitable for use in the present invention. For example, the dephosphorylation of glycerol-3-phosphate to yield glycerol may be achieved with one or more of the following general or specific phosphatases: alkaline phosphatase (EC 3.1.3.1) [GenBank M19159, M29663, U02550 or M33965]; acid phosphatase (EC 3.1.3.2) [GenBank U51210, U19789, U28658 or L20566]; glycerol-3-phosphatase (EC 3.1.3.21) [GenBank Z38060 or U18813x11]; glucose-1-phosphatase (EC 3.1.3.10) [GenBank M33807]; glucose-6-phosphatase (EC 3.1.3.9) [GenBank U00445]; fructose-1,6-bisphosphatase (EC 3.1.3.11) [GenBank X12545 or J03207] or phosphotidyl glycero phosphate phosphatase (EC 3.1.3.27) [GenBank M23546 and M23628].

Genes encoding glycerol kinase are known. For example, GUT1 encoding the glycerol kinase from *Saccharomyces* has been isolated and sequenced (Pavlik et al. (1993), *Curr. Genet.*, 24:21) and the base sequence is given by SEQ ID NO:6, which encodes the amino acid sequence given in SEQ ID NO: 15. Alternatively, glpK encodes a glycerol kinase from *E. coli* and is characterized by the base sequence given in GeneBank L19201, base pairs 77347–78855.

Genes encoding glycerol dehydrogenase are known. For example, gldA encodes a glycerol dehydrogenase from *E. coli* and is characterized by the base sequence given in GeneBank U00006, base pairs 3174–4316. Alternatively, dhaD refers to another gene that encodes a glycerol dehydrogenase from *Citrobacter freundii* and is characterized by the base sequence given in GeneBank U09771, base pairs 2557–3654.

Host Cells

Suitable host cells for the recombinant production of glycerol by the expression of G3PDH and G3P phosphatase may be either prokaryotic or eukaryotic and will be limited only by their ability to express active enzymes. Preferred host cells will be those bacteria, yeasts, and filamentous fungi typically useful for the production of glycerol such as *Citrobacter, Enterobacter, Clostridium, Klebsiella, Aerobacter, Lactobacillus, Aspergillus, Saccharomyces, Schizosaccharomyces, Zygosaccharomyces, Pichia, Kluyveromyces, Candida, Hansenula, Debaryomyces, Mucor, Torulopsis, Methylobacter, Escherichia, Salmonella, Bacillus, Streptomyces* and *Pseudomonas*. Preferred in the present invention are *E. coli* and *Saccharomyces*.

Where glycerol is a key intermediate in the production of 1,3-propanediol the host cell will either have an endogenous gene encoding a protein having a dehydratase activity or will acquire such a gene through transformation. Host cells particularly suited for production of 1,3-propanediol are *Citrobacter, Enterobacter, Clostridium, Klebsiella, Aerobacter, Lactobacillus*, and *Salmonella*, which have endogenous genes encoding dehydratase enzymes. Additionally, host cells that lack such an endogeneous gene include *E. coli*.

Vectors and Expression Cassettes

The present invention provides a variety of vectors and transformation and expression cassettes suitable for the cloning, transformation and expression of G3PDH and G3P phosphatase into a suitable host cell. Suitable vectors will be those which are compatible with the bacterium employed. Suitable vectors can be derived, for example, from a bacteria, a virus (such as bacteriophage T7 or a M-13 derived phage), a cosmid, a yeast or a plant. Protocols for obtaining and using such vectors are known to those in the art (Sambrook et al., Molecular Cloning: A Laboratory Manual—volumes 1, 2, 3 (Cold Spring Harbor Laboratory: Cold Spring Harbor, N.Y., 1989)).

Typically, the vector or cassette contains sequences directing transcription and translation of the appropriate gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell. Such control regions need not be derived from the genes native to the specific species chosen as a production host.

Initiation control regions, or promoters, which are useful to drive expression of the G3PDH and G3P phosphatase genes in the desired host cell are numerous and familiar to those skilled in the art. Virtually any promoter capable of driving these genes is suitable for the present invention including but not limited to CYC1, HIS3, GAL1, GAL10, ADH1, PGK, PHO5, GAPDH, ADC1, TRP1, URA3, LEU2, ENO, and TPI (useful for expression in *Saccharomyces*); AOX1 (useful for expression in *Pichia*); and lac, trp, $\lambda P_L$, $\lambda P_R$, T7, tac, and trc, (useful for expression in *E. coli*).

Termination control regions may also be derived from various genes native to the preferred hosts. Optionally, a termination site may be unnecessary; however, it is most preferred if included.

For effective expression of the instant enzymes, DNA encoding the enzymes are linked operably through initiation codons to selected expression control regions such that expression results in the formation of the appropriate messenger RNA.

Transformation of Suitable Hosts and Expression of G3PDH And G3P Phosphatase for the Production of Glycerol Once suitable cassettes are constructed they are used to transform appropriate host cells. Introduction of the cassette containing the genes encoding G3PDH and/or G3P phosphatase into the host cell may be accomplished by known procedures such as by transformation, e.g., using calcium-permeabilized cells, electroporation, or by transfection using a recombinant phage virus (Sambrook et al., supra).

In the present invention AH21 and DAR1 cassettes were used to transform the *E. coli* DH5α and FM5 as fully described in the GENERAL METHODS and EXAMPLES.

Random and Site Specific Mutagenisis for Disrupting Enzyme Activities:

Enzyme pathways by which organisms metabolize glycerol are known in the art, FIG. 1. Glycerol is converted to glycerol-3-phosphate (G3P) by an ATP-dependent glycerol kinase; the G3P may then be oxidized to DHAP by G3PDH. In a second pathway, glycerol is oxidized to dihydroxyacetone (DHA) by a glycerol dehydrogenase; the DHA may then be converted to DHAP by an ATP-dependent DHA kinase. In a third pathway, glycerol is oxidized to glyceraldehyde by a glycerol dehydrogenase; the glyceraldehyde may be phosphorylated to glyceraldehyde-3-phosphate by an ATP-dependent kinase. DHAP and glyceraldehyde-3-phosphate, interconverted by the action of triosephosphate isomerase, may be further metabolized via central metabolism pathways. These pathways, by introducing by-products, are deleterious to glycerol production.

One aspect of the present invention is the ability to provide a production organism for the production of glycerol where the glycerol-converting activities of glycerol kinase and glycerol dehydrogenase have been deleted. Methods of creating deletion mutants are common and well known in the art. For example, wild type cells may be exposed to a variety of agents such as radiation or chemical mutagens and then screened for the desired phenotype. When creating mutations through radiation either ultraviolet (UV) or ionizing radiation may be used. Suitable short wave UV wavelengths for genetic mutations will fall within the range of 200 nm to 300 nm where 254 nm is preferred. UV radiation in this wavelength principally causes changes within nucleic acid sequence from guanidine and cytosine to adenine and thymidine. Since all cells have DNA repair mechanisms that would repair most UV induced mutations, agents such as caffeine and other inhibitors may be added to interrupt the repair process and maximize the number of effective mutations. Long wave UV mutations using light in the 300 nm to 400 nm range are also possible but are generally not as effective as the short wave UV light unless used in conjunction with various activators such as psoralen dyes that interact with the DNA.

Mutagenesis with chemical agents is also effective for generating mutants and commonly used substances include chemicals that affect nonreplicating DNA such as $HNO_2$ and $NH_2OH$, as well as agents that affect replicating DNA such as acridine dyes, notable for causing frameshift mutations. Specific methods for creating mutants using radiation or chemical agents are well documented in the art. See for example Thomas D. Brock in Biotechnology: *A Textbook of Industrial Microbiology*, Second Edition (1989) Sinauer Associates, Inc., Sunderland, Mass., or Deshpande, Mukund V., *Appl. Biochem. Biotechnol.*, 36, 227, (1992), herein incorporated by reference.

After mutagenesis has occurred, mutants having the desired phenotype may be selected by a variety of methods. Random screening is most common where the mutagenized cells are selected for the ability to produce the desired product or intermediate. Alternatively, selective isolation of mutants can be performed by growing a mutagenized population on selective media where only resistant colonies can develop. Methods of mutant selection are highly developed and well known in the art of industrial microbiology. See Brock, Supra., DeMancilha et al., *Food Chem.*, 14, 313, (1984).

Biological mutagenic agents which target genes randomly are well known in the art. See for example De Bruijn and Rossbach in *Methods for General and Molecular Bacteriology* (1994) American Society for Microbiology, Washington, D.C. Alternatively, provided that gene sequence is known, chromosomal gene disruption with specific deletion or replacement is achieved by homologous recombination with an appropriate plasmid. See for example Hamilton et al. (1989) *J. Bacteriol.* 171:4617–4622, Balbas et al. (1993) *Gene* 136: 211–213, Gueldener et al. (1996) *Nucleic Acids Res.* 24: 2519–2524, and Smith et al. (1996) *Methods Mol. Cell. Biol.* 5: 270–277.

It is contemplated that any of the above cited methods may be used for the deletion or inactivation of glycerol kinase and glycerol dehydrogenase activities in the preferred production organism.

Media and Carbon Substrates

Fermentation media in the present invention must contain suitable carbon substrates. Suitable substrates may include but are not limited to monosaccharides such as glucose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. Additionally, the carbon substrate may also be one-carbon substrates such as carbon dioxide, or methanol for which metabolic conversion into key biochemical intermediates has been demonstrated.

Glycerol production from single carbon sources (e.g., methanol, formaldehyde or formate) has been reported in methylotrophic yeasts (Yamada et al. (1989), *Agric. Biol. Chem.*, 53(2):541–543) and in bacteria (Hunter et al. (1985), *Biochemistry*, 24:4148–4155). These organisms can assimilate single carbon compounds, ranging in oxidation state from methane to formate, and produce glycerol. The pathway of carbon assimilation can be through ribulose monophosphate, through serine, or through xylulose-monophosphate (Gottschalk, *Bacterial Metabolism*, Second Edition, Springer-Verlag: New York (1986)). The ribulose monophosphate pathway involves the condensation of formate with ribulose-5-phosphate to form a 6 carbon sugar that becomes fructose and eventually the three carbon product, glyceraldehyde-3-phosphate. Likewise, the serine pathway assimilates the one-carbon compound into the glycolytic pathway via methylenetetrahydrofolate.

In addition to one and two carbon substrates, methylotrophic organisms are also known to utilize a number of other carbon-containing compounds such as methylamine, glucosamine and a variety of amino acids for metabolic activity. For example, methylotrophic yeast are known to utilize the carbon from methylamine to form trehalose or glycerol (Bellion et al. (1993), *Microb. Growth C1-Compd.*, [Int. Symp.], 7th, 415–32. Editor(s): Murrell, J. Collin; Kelly, Don P. Publisher: Intercept, Andover, UK). Similarly, various species of *Candida* will metabolize alanine or oleic acid (Sulter et al. (1990), *Arch. Microbiol.*, 153(5):485–9). Hence, the source of carbon utilized in the present invention may encompass a wide variety of carbon-containing substrates and will only be limited by the choice of organism.

Although all of the above mentioned carbon substrates and mixtures thereof are suitable in the present invention, preferred carbon substrates are monosaccharides, oligosaccharides, polysaccharides, single-carbon substrates or mixtures thereof. More preferred are sugars such as glucose, fructose, sucrose, maltose, lactose and single carbon substrates such as methanol and carbon dioxide. Most preferred as a carbon substrate is glucose.

In addition to an appropriate carbon source, fermentation media must contain suitable minerals, salts, cofactors, buffers and other components, known to those skilled in the art, suitable for the growth of the cultures and promotion of the enzymatic pathway necessary for glycerol production.

Culture Conditions

Typically cells are grown at 30° C. in appropriate media. Preferred growth media are common commercially prepared media such as Luria Bertani (LB) broth, Sabouraud Dextrose (SD) broth, or Yeast medium (YM) broth. Other defined or synthetic growth media may also be used and the appropriate medium for growth of the particular microorganism will be known by one skilled in the art of microbiology or fermentation science. The use of agents known to modulate catabolite repression directly or indirectly, e.g., cyclic adenosine 3':5'-monophosphate, may also be incorporated into the reaction media. Similarly, the use of agents known to modulate enzymatic activities (e.g., sulfites, bisulfites, and alkalis) that lead to enhancement of glycerol production may be used in conjunction with or as an alternative to genetic manipulations.

Suitable pH ranges for the fermentation are between pH 5.0 to pH 9.0 where the range of pH 6.0 to pH 8.0 is preferred for the initial condition.

Reactions may be performed under aerobic or anaerobic conditions where anaerobic or microaerobic conditions are preferred.

Identification of G3PDH, Zlycerol Dehydrogenase, G3P Phosphatase, and Glycerol Kinase Activities The levels of expression of the proteins G3PDH, G3P phosphatase glycerol dehydrogenase, and glycerol kinase are measured by enzyme assays. Generally, G3PDH activity and glycerol dehydrogenase activity assays rely on the spectral properties of the cosubstrate, NADH, in the DHAP conversion to G-3-P and the DHA conversion to glycerol, respectively. NADH has intrinsic UV/vis absorption and its consumption can be monitored spectrophotometrically at 340 nm. G3P phosphatase activity can be measured by any method of measuring the inorganic phosphate liberated in the reaction. The most commonly used detection method uses the visible spectroscopic determination of a blue-colored phosphomolybdate ammonium complex. Glycerol kinase activity can be measured by the detection of G3P from glycerol and ATP, for example, by NMR. Assays can be directed toward more specific characteristics of individual enzymes if necessary, for example, by the use of alternate cofactors.

Identification and Recovery of Glycerol and Other Products (e.g. 1,3-Propanediol)

Glycerol and other products (e.g. 1,3-propanediol) may be identified and quantified by high performance liquid chromatography (HPLC) and gas chromatography/mass spectroscopy (GC/MS) analyses on the cell-free extracts. Preferred is a HPLC method where the fermentation media are analyzed on an analytical ion exchange column using a mobile phase of 0.01N sulfuric acid in an isocratic fashion.

Methods for the recovery of glycerol from fermentation media are known in the art. For example, glycerol can be obtained from cell media by subjecting the reaction mixture to the following sequence of steps: filtration; water removal; organic solvent extraction; and fractional distillation (U.S. Pat. No. 2,986,495).

DESCRIPTION OF THE PREFERRED EMBODIMENTS

Production of Glycerol

The present invention describes a method for the production of glycerol from a suitable carbon source utilizing a recombinant organism. Particularly suitable in the invention is a bacterial host cell, transformed with an expression cassette carrying either or both of a gene that encodes a protein having a glycerol-3-phosphate dehydrogenase activity and a gene encoding a protein having a glycerol-3-phosphatase activity. In addition to the G3PDH and G3P phosphatase genes, the host cell will contain disruptions in either or both of genes encoding endogenous glycerol kinase and glycerol dehydrogenase enzymes. The combined effect of the foreign G3PDH and G3P phosphatase genes (providing a pathway from the carbon source to glycerol) with the gene disruptions (blocking the conversion of glycerol) results in an organism that is capable of efficient and reliable glycerol production.

Although the optimal organism for glycerol production contains the above mentioned gene disruptions, glycerol production is possible with a host cell containing either one or both of the foreign G3PDH and G3P phosphatase genes in the absence of such disruptions. For example, the recombinant *E. coli* strain AA200 carrying the DAR1 gene (Example 1) was capable of producing between 0.38 g/L and 0.48 g/L of glycerol depending on fermentation parameters. Similarly, the *E. coli* DH5α, carrying and expressible GPP2 gene (Example 2), was capable of 0.2 g/L of glycerol production. Where both genes are present, (Example 3 and 4), glycerol production attained about 40 g/L. Where both genes are present in conjunction with an elimination of the endogenous glycerol kinase activity, a reduction in the conversion of glycerol may be seen (Example 8). Furthermore, the presence of glycerol dehydrogenase activity is linked to the conversion of glycerol under glucose-limited conditions; thus, it is anticipated that the elimination of glycerol dehydrogenase activity will result in the reduction of glycerol conversion (Example 8).

Production of 1,3-Propanediol

The present invention may also be adapted for the production of 1,3-propanediol by utilizing recombinant organisms expressing the foreign G3PDH and/or G3P phosphatase genes and containing disruptions in the endogenous glycerol kinase and/or glycerol dehydrogenase activities. Additionally, the invention provides for the process for the production of 1,3-propanediol from a recombinant organism where multiple copies of endogeneous genes are introduced. In addition to these genetic alterations, the production cell will require the presence of a gene encoding an active dehydratase enzyme. The dehydratase enzyme activity may either be a glycerol dehydratase or a diol dehydratase. The dehydratase enzyme activity may result from either the expression of an endogenous gene or from the expression of a foreign gene transfected into the host organism. Isolation and expression of genes encoding suitable dehydratase enzymes are well known in the art and are taught by applicants in PCT/US96/06705, filed 5 Nov. 1996 and U.S. Pat. No. 5,686,276 and U.S. Pat. No. 5,633,362, hereby incorporated by reference. It will be appreciated that, as glycerol is a key intermediate in the production of 1,3-propanediol, where the host cell contains a dehydratase activity in conjunction with expressed foreign G3PDH and/or G3P phosphatase genes and in the absence of the glycerol-converting glycerol kinase or glycerol dehydrogenase activities, the cell will be particularly suited for the production of 1,3-propanediol.

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

EXAMPLES

General Methods

Procedures for phosphorylations, ligations, and transformations are well known in the art. Techniques suitable for use in the following examples may be found in Sambrook et al., *Molecular Cloning: A Laboratory Manual*, Second Edition, Cold Spring Harbor Laboratory Press (1989).

Materials and methods suitable for the maintenance and growth of bacterial cultures are well known in the art. Techniques suitable for use in the following examples may be found in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994) or in *Biotechnology: A Textbook of Industrial Microbiology* (Thomas D. Brock, Second Edition (1989) Sinauer Associates, Inc., Sunderland, Mass.). All reagents and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

The meaning of abbreviations is as follows: "h" means hour(s), "min" means minute(s), "sec" means second(s), "d" means day(s), "mL" means milliliters, "L" means liters.

Cell Strains

The following *Escherichia coli* strains were used for transformation and expression of G3PDH and G3P phosphatase. Strains were obtained from the *E. coli* Genetic Stock Center, ATCC, or Life Technologies (Gaithersburg, Md.). AA200 (garB10 fhuA22 ompF627 fadL701 relA1 pit-10 spoT1 tpi-1 phoMS510 mcrb1) (Anderson et al., (1970), *J. Gen. Microbiol.*, 62:329). BB20 (tonA22 ΔphoA8 fadL701 relA1 glpR2 glpD3 pit-10 gpsA20 spoT1 T2R) (Cronan et al., *J. Bact.*, 118:598). DH5α (deoR endA1 gyrA96 hsdR17 recA1 relA1 supE44 thi-1 Δ(lacZYA-argFV169) phi80lacZΔM15 F⁻) (Woodcock et al., (1989), *Nucl. Acids Res.*, 17:3469). FM5 *Escherichia coli* (ATCC 53911).

Identification of Glycerol

The conversion of glucose to glycerol was monitored by HPLC and/or GC. Analyses were performed using standard techniques and materials available to one of skill in the art of chromatography. One suitable method utilized a Waters Maxima 820 HPLC system using UV (210 nm) and RI detection. Samples were injected onto a Shodex SH-1011 column (8 mm×300 mm; Waters, Milford, Mass.) equipped with a Shodex SH-1011P precolumn (6 mm×50 mm), temperature-controlled at 50° C., using 0.01 N $H_2SO_4$ as mobile phase at a flow rate of 0.69 mL/min. When quantitative analysis was desired, samples were prepared with a known amount of trimethylacetic acid as an external standard. Typically, the retention times of 1,3-propanediol (RI detection), glycerol (RI detection) and glucose (RI detection) were 21.39 min, 17.03 min and 12.66 min, respectively.

Glycerol was also analyzed by GC/MS. Gas chromatography with mass spectrometry detection for separation and quantitation of glycerol was performed using a DB-WAX column (30 m, 0.32 mm I.D., 0.25 um film thickness, J & W Scientific, Folsom, Calif.) at the following conditions: injector: split, 1:15; sample volume: 1 uL; temperature profile: 150° C. intitial temperature with 30 sec hold, 40° C./min to 180° C., 20° C./min to 240° C., hold for 2.5 min. Detection: EI Mass Spectrometry (Hewlett Packard 5971, San Fernando, Calif.), quantitative SIM using ions 61 m/z and 64 m/z as target ions for glycerol and glycerol-d8, and ion 43 m/z as qualifier ion for glycerol. Glycerol-d8 was used as an internal standard.

Assay for Glycerol-3-Phosphatase. G3P Phosphatase

The assay for enzyme activity was performed by incubating the extract with an organic phosphate substrate in a bis-Tris or MES and magnesium buffer, pH 6.5. The substrate used was either 1-α-glycerol phosphate, or d,1-α-glycerol phosphate. The final concentrations of the reagents in the assay are: buffer (20 mM bis-Tris or 50 mM MES); $MgCl_2$ (10 mM); and substrate (20 mM). If the total protein in the sample was low and no visible precipitation occurs with an acid quench, the sample was conveniently assayed in the cuvette. This method involved incubating an enzyme sample in a cuvette that contained 20 mM substrate (50 μL, 200 mM), 50 mM MES, 10 mM $MgCl_2$, pH 6.5 buffer. The final phosphatase assay volume was 0.5 mL. The enzyme-containing sample was added to the reaction mixture; the contents of the cuvette were mixed and then the cuvette was placed in a circulating water bath at T=37° C. for 5 to 120 min, the length of time depending on whether the phosphatase activity in the enzyme sample ranged from 2 to 0.02 U/mL. The enzymatic reaction was quenched by the addition of the acid molybdate reagent (0.4 mL). After the Fiske SubbaRow reagent (0.1 mL) and distilled water (1.5 mL) were added, the solution was mixed and allowed to develop.

After 10 min, to allow full color development, the absorbance of the samples was read at 660 nm using a Cary 219 UV/Vis spectrophotometer. The amount of inorganic phosphate released was compared to a standard curve that was prepared by using a stock inorganic phosphate solution (0.65 mM) and preparing 6 standards with final inorganic phosphate concentrations ranging from 0.026 to 0.130 μmol/mL.

Spectrophotometric Assay for Glycerol 3-Phosphate Dehydrogenase (G3PDH) Activity The following procedure was used as modified below from a method published by Bell et al. (1975), *J. Biol. Chem.*, 250:7153–8. This method involved incubating an enzyme sample in a cuvette that contained 0.2 mM NADH; 2.0 mM dihydroxyacetone phosphate (DHAP), and enzyme in 0.1 M Tris/HCl, pH 7.5 buffer with 5 mM DTT, in a total volume of 1.0 mL at 30° C. The spectrophotometer was set to monitor absorbance changes at the fixed wavelength of 340 nm. The instrument was blanked on a cuvette containing buffer only. After the enzyme was added to the cuvette, an absorbance reading was taken. The first substrate, NADH (50 uL 4 mM NADH; absorbance should increase approx 1.25 AU), was added to determine the background rate. The rate should be followed for at least 3 min. The second substrate, DHAP (50 uL 40 mM DHAP), was then added and the absorbance change over time was monitored for at least 3 min to determine to determine the gross rate. G3PDH activity was defined by subtracting the background rate from the gross rate.

$^{13}$C-NMR Assay for Glycerol Kinase Activity

An appropriate amount of enzyme, typically a cell-free crude extract, was added to a reaction mixture containing 40 mM ATP, 20 mM MgSO$_4$, 21 mM uniformly $^{13}$C labelled glycerol (99%, Cambridge Isotope Laboratories), and 0.1 M Tris-HCl, pH 9 for 75 min at 25° C. The conversion of glycerol to glycerol 3-phosphate was detected by $^{13}$C-NMR (125 MHz): glycerol (63.11 ppm, d, J=41 Hz and 72.66 ppm, t, J=41 Hz); glycerol 3-phosphate (62.93 ppm, d, J=41 Hz; 65.31 ppm, br d, J=43 Hz; and 72.66 ppm, dt, J=6, 41 Hz).

NADH-linked Glycerol Dehydrogenase Assay

NADH-linked glycerol dehydrogenase activity in *E. coli* strains (gldA) was determined after protein separation by non-denaturing polyacrylamide gel electrophoresis. The conversion of glycerol plus NAD+ to dihydroxyacetone plus NADH was coupled with the conversion of 3-[4,5-dimethylthiazol-2-yl]-2,5-diphenyltetrazolium bromide (MTT) to a deeply colored formazan, using phenazine methosulfate (PMS) as mediator. (Tang et al. (1997) *J. Bacteriol.* 140:182).

Electrophoresis was performed in duplicate by standard procedures using native gels (8–16% TG, 1.5 mm, 15 lane gels from Novex, San Diego, Calif.). Residual glycerol was removed from the gels by washing 3× with 50 mM Tris or potassium carbonate buffer, pH 9 for 10 min. The duplicate gels were developed, with and without glycerol (approx. 0.16 M final concentration), in 15 mL of assay solution containing 50 mM Tris or potassium carbonate, pH 9, 60 mg ammonium sulfate, 75 mg NAD+, 1.5 mg MTT, and 0.5 mg PMS.

The presence or absence of NADH-linked glycerol dehydrogenase activity in *E. coli* strains (gldA) was also determined, following polyacrylamide gel electrophoresis, by reaction with polyclonal antibodies raised to purified *K. pneumoniae* glycerol dehydrogenase (dhaD).

Plasmid Construction and Strain Construction

Cloning and Expression of Glycerol 3-Phosphatase for Increase of Glycerol Production in *E. coli* DH5α and FM5

The *Saccharomyces cerevisiae* chromosomeV lamda clone 6592 (Gene Bank, accession # U18813x11) was obtained from ATCC. The glycerol 3-phosphate phosphatase (GPP2) gene was cloned by cloning from the lamda clone as target DNA using synthetic primers (SEQ ID NO: 16 with SEQ ID NO: 17) incorporating an BamHI-RBS-XbaI site at the 5' end and a SmaI site at the 3' end. The product was subcloned into pCR-Script (Stratagene, Madison, Wis.) at the SrfI site to generate the plasmids pAH15 containing GPP2. The plasmid pAH15 contains the GPP2 gene in the inactive orientation for expression from the lac promoter in pCR-Script SK+. The BamHI-SmaI fragment from pAH15 containing the GPP2 gene was inserted into pBlueScriptII SK+ to generate plasmid pAH19. The pAH19 contains the GPP2 gene in the correct orientation for expression from the lac promoter. The XbaI-PstI fragment from pAH19 containing the GPP2 gene was inserted into pPHOX2 to create plasmid pAH21. The pAH21/DH5α is the expression plasmid.

Plasmids for the Over-Expression of DAR1 in *E. coli*

DAR1 was isolated by PCR cloning from genomic *S. cerevisiae* DNA using synthetic primers (SEQ ID NO: 18 with SEQ ID NO: 19). Successful PCR cloning places an NcoI site at the 5' end of DAR1 where the ATG within NcoI is the DAR1 initiator methionine. At the 3' end of DAR1 a BamHI site is introduced following the translation terminator. The PCR fragments were digested with NcoI+BamHI and cloned into the same sites within the expression plasmid pTrc99A (Pharmacia, Piscataway, N.J.) to give pDAR1A.

In order to create a better ribosome binding site at the 5' end of DAR1, an SpeI-RBS-NcoI linker obtained by annealing synthetic primers (SEQ ID NO:20 with SEQ ID NO:21) was inserted into the NcoI site of pDAR1A to create pAH40. Plasmid pAH40 contains the new RBS and DAR1 gene in the correct orientation for expression from the trc promoter of pTrc99A (Pharmacia, Piscataway, N.J.). The NcoI-BamHI fragement from pDAR1A and an second set of SpeI-RBS-NcoI linker obtained by annealing synthetic primers (SEQ ID NO:22 with SEQ ID NO:23) was inserted into the SpeI-BamHI site of pBC-SK+ (Stratagene, Madison, Wis.) to create plasmid pAH42. The plasmid pAH42 contains a chloramphenicol resistant gene.

Construction of Expression Cassettes for DAR1 and GPP2

Expression cassettes for DAR1 and GPP2 were assembled from the individual DAR1 and GPP2 subclones described above using standard molecular biology methods. The BamHI-PstI fragment from pAH19 containing the ribosomal binding site (RBS) and GPP2 gene was inserted into pAH40 to create pAH43. The BamHI-PstI fragment from pAH19 containing the RBS and GPP2 gene was inserted into pAH42 to create pAH45.

The ribosome binding site at the 5' end of GPP2 was modified as follows. A BamHI-RBS-SpeI linker, obtained by annealing synthetic primers GATCCAGGAAACAGA (SEQ ID NO:24) with CTAGTCTGTTTCCTG (SEQ ID NO:25) to the XbaI-PstI fragment from pAH19 containing the GPP2 gene, was inserted into the BamHI-PstI site of pAH40 to create pAH48. Plasmid pAH48 contains the DAR1 gene, the modified RBS, and the GPP2 gene in the correct orientation for expression from the trc promoter of pTrc99A (Pharmacia, Piscataway, N.J.).

Transformation of E. coli

All the plasmids described here were transformed into *E. coli* DH5α or FM5 using standard molecular biology techniques. The transformants were verified by its DNA RFLP pattern.

Example 1

Production of Glycerol from E. coli Transformed with G3PDH Gene

Media

Synthetic media was used for anaerobic or aerobic production of glycerol using *E. coli* cells transformed with pDAR1A. The media contained per liter 6.0 g $Na_2HPO_4$, 3.0 g $KH_2PO_4$, 1.0 g $NH_4Cl$, 0.5 g NaCl, 1 mL 20% $MgSO_4 \cdot 7H_2O$, 8.0 g glucose, 40 mg casamino acids, 0.5 ml 1% thiamine hydrochloride, 100 mg ampicillin.

Growth Conditions

Strain AA200 harboring pDAR1A or the pTrc99A vector was grown in aerobic conditions in 50 mL of media shaking at 250 rpm in 250 mL flasks at 37° C. At $A_{600}$ 0.2–0.3 isopropylthio-β-D-galactoside was added to a final concentration of 1 mM and incubation continued for 48 h. For anaerobic growth samples of induced cells were used to fill Falcon #2054 tubes which were capped and gently mixed by rotation at 37° C. for 48 h. Glycerol production was determined by HPLC analysis of the culture supernatants. Strain pDAR1A/AA200 produced 0.38 g/L glycerol after 48 h under anaerobic conditions, and 0.48 g/L under aerobic conditions.

Example 2

Production of Glycerol from E. coli Transformed with G3P Phosphatase Gene (GPP2)

Media

Synthetic phoA media was used in shake flasks to demonstrate the increase of glycerol by GPP2 expression in *E. coli*. The phoA medium contained per liter: Amisoy, 12 g; ammonium sulfate, 0.62 g; MOPS, 10.5 g; Na-citrate, 1.2 g; NaOH (1 M), 10 mL; 1 M $MgSO_4$, 12 mL; 100× trace elements, 12 mL; 50% glucose, 10 mL; 1% thiamine, 10 mL; 100 mg/mL L-proline, 10 mL; 2.5 mM $FeCl_3$, 5 mL; mixed phosphates buffer, 2 mL (5 mL 0.2 M $NaH_2PO_4$+9 mL 0.2 M $K_2HPO_4$), and pH to 7.0. The 100× traces elements for phoA medium/L contained: $ZnSO_4 \cdot 7H_2O$, 0.58 g; $MnSO_4 \cdot H_2O$, 0.34 g; $CuSO_4 \cdot 5H_2O$, 0.49 g; $CoCl_2 \cdot 6H_2O$, 0.47 g; $H_3BO_3$, 0.12 g, $NaMoO_4 \cdot 2H_2O$, 0.48 g.

Shake Flasks Experiments

The strains pAH21/DH5α (containing GPP2 gene) and pPHOX2/DH5α (control) were grown in 45 mL of media (phoA media, 50 ug/mL carbenicillin, and 1 ug/mL vitamin $B_{12}$) in a 250 mL shake flask at 37° C. The cultures were grown under aerobic condition (250 rpm shaking) for 24 h. Glycerol production was determined by HPLC analysis of the culture supernatant. pAH21/DH5α produced 0.2 g/L glycerol after 24 h.

Example 3

Production of Glycerol from D-Glucose using Recombinant *E. coli* Containing both GPP2 and DAR1

Growth for demonstration of increased glycerol production by *E. coli* DH5α-containing pAH43 proceeds aerobically at 37° C. in shake-flask cultures (erlenmeyer flasks, liquid volume ⅕th of total volume).

Cultures in minimal media/1% glucose shake-flasks are started by inoculation from overnight LB/1% glucose culture with antibiotic selection. Minimal media are: filter-sterilized defined media, final pH 6.8 (HCl), contained per liter: 12.6 g $(NH_4)_2SO_4$, 13.7 g $K_2HPO_4$, 0.2 g yeast extract (Difco), 1 g $NaHCO_3$, 5 mg vitamin $B_{12}$, 5 mL Modified Balch's Trace-Element Solution (the composition of which can be found in *Methods for General and Molecular Bacteriology* (P. Gerhardt et al., eds, p. 158, American Society for Microbiology, Washington, D.C. (1994)). The shake-flasks are incubated at 37° C. with vigorous shaking for overnight, after which they are sampled for GC analysis of the supernatant. The pAH43/DH5α showed glycerol production of 3.8 g/L after 24 h.

Example 4

Production of Glycerol from D-Glucose using Recombinant E. coli Containing Both GPP2 and DAR1

Example 4 illustrates the production of glucose from the recombinant *E. coli* DH5α/pAH48, containing both the GPP2 and DAR1 genes.

The strain DH5a/pAH48 was constructed as described above in the GENERAL METHODS.

Pre-Culture

DH5α/pAH48 were pre-cultured for seeding into a fermentation run. Components and protocols for the pre-culture are listed below.

| Pre-Culture Media | |
|---|---|
| $KH_2PO_4$ | 30.0 g/L |
| Citric acid | 2.0 g/L |
| $MgSO_4 \cdot 7H_2O$ | 2.0 g/L |
| 98% $H_2SO_4$ | 2.0 mL/L |
| Ferric ammonium citrate | 0.3 g/L |
| $CaCl_2 \cdot 2H_2O$ | 0.2 g/L |
| Yeast extract | 5.0 g/L |
| Trace metals | 5.0 mL/L |
| Glucose | 10.0 g/L |
| Carbenicillin | 100.0 mg/L |

The above media components were mixed together and the pH adjusted to 6.8 with $NH_4OH$. The media was then filter sterilized.

Trace metals were used according to the following recipe:

| Citric acid, monohydrate | 4.0 g/L |
|---|---|
| $MgSO_4 \cdot 7H_2O$ | 3.0 g/L |
| $MnSO_4 \cdot 7H_2O$ | 0.5 g/L |
| NaCl | 1.0 g/L |
| $FeSO4 \cdot 7H_2O$ | 0.1 g/L |
| $CoCl2 \cdot 6H_2O$ | 0.1 g/L |
| CaCl2 | 0.1 g/L |
| $ZnSO_4 \cdot 7H_2O$ | 0.1 g/L |
| $CuSO_4 \cdot 5H_2O$ | 10 mg/L |
| $AlK(SO_4)_2 \cdot 12H_2O$ | 10 mg/L |
| $H_3BO_3$ | 10 mg/L |

-continued

| | |
|---|---|
| $Na_2MoO_4 \cdot 2H_2O$ | 10 mg/L |
| $NiSO4.6H_2O$ | 10 mg/L |
| $Na_2SeO_3$ | 10 mg/L |
| $Na_2WO_4 \cdot 2H_2O$ | 10 mg/L |

Cultures were started from seed culture inoculated from 50 μL frozen stock (15% glycerol as cryoprotectant) to 600 mL medium in a 2-L Erlenmeyer flask. Cultures were grown at 30° C. in a shaker at 250 rpm for approximately 12 h and then used to seed the fermenter.

Fermentation Growth

| Fermentation growth | |
|---|---|
| Vessel | |
| 15-L stirred tank fermenter | |
| Medium | |
| $KH_2PO_4$ | 6.8 g/L |
| Citric acid | 2.0 g/L |
| $MgSO_4 \cdot 7H_2O$ | 2.0 g/L |
| 98% $H_2SO_4$ | 2.0 mL/L |
| Ferric ammonium citrate | 0.3 g/L |
| $CaCl_2 \cdot 2H_2O$ | 0.2 g/L |
| Mazu DF204 antifoam | 1.0 mL/L |

The above components were sterilized together in the fermenter vessel. The pH was raised to 6.7 with $NH_4OH$. Yeast extract (5 g/L) and trace metals solution (5 mL/L) were added aseptically from filter sterilized stock solutions. Glucose was added from 60% feed to give final concentration of 10 g/L. Carbenicillin was added at 100 mg/L. Volume after inoculation was 6 L.

Environmental Conditions for Fermentation

The temperature was controlled at 36° C. and the air flow rate was controlled at 6 standard liters per minute. Back pressure was controlled at 0.5 bar. The agitator was set at 350 rpm. Aqueous ammonia was used to control pH at 6.7. The glucose feed (60% glucose monohydrate) rate was controlled to maintain excess glucose.

Results

The results of the fermentation run are given in Table 1.

TABLE 1

| EFT (hr) | OD550 (AU) | [Glucose] (g/L) | [Glycerol] (g/L) | Total Glucose Fed (g) | Total Glycerol Produced (g) |
|---|---|---|---|---|---|
| 0 | 0.8 | 9.3 | | 25 | |
| 6 | 4.7 | 4.0 | 2.0 | 49 | 14 |
| 8 | 5.4 | 0 | 3.6 | 71 | 25 |
| 10 | 6.7 | 0.0 | 4.7 | 116 | 33 |
| 12 | 7.4 | 2.1 | 7.0 | 157 | 49 |
| 14.2 | 10.4 | 0.3 | 10.0 | 230 | 70 |
| 16.2 | 18.1 | 9.7 | 15.5 | 259 | 106 |
| 18.2 | 12.4 | 14.5 | | 305 | |
| 20.2 | 11.8 | 17.4 | 17.7 | 353 | 119 |
| 22.2 | 11.0 | 12.6 | | 382 | |
| 24.2 | 10.8 | 6.5 | 26.6 | 404 | 178 |
| 26.2 | 10.9 | 6.8 | | 442 | |
| 28.2 | 10.4 | 10.3 | 31.5 | 463 | 216 |
| 30.2 | 10.2 | 13.1 | 30.4 | 493 | 213 |
| 32.2 | 10.1 | 8.1 | 28.2 | 512 | 196 |
| 34.2 | 10.2 | 3.5 | 33.4 | 530 | 223 |
| 36.2 | 10.1 | 5.8 | | 548 | |
| 38.2 | 9.8 | 5.1 | 36.1 | 512 | 233 |

Example 5

Engineering of Glycerol Kinase Mutants of *E. Coli* FM5 for Production of Glycerol from Glucose Construction of Integration Plasmid for Glycerol Kinase Gene Replacement in *E. coli* FM5

*E. coli* FM5 genomic DNA was prepared using the Puregene DNA Isolation Kit (Gentra Systems, Minneapolis, Minn.). A 1.0 kb DNA fragment containing partial glpF and glycerol kinase (glpK) genes was amplified by PCR (Mullis and Faloona, *Methods Enzymol.*, 155:335–350, 1987) from FM5 genomic DNA using primers SEQ ID NO:26 and SEQ ID NO:27. A 1.1 kb DNA fragment containing partial glpK and glpX genes was amplified by PCR from FM5 genomic DNA using primers SEQ ID NO:28 and SEQ ID NO:29. A MunI site was incorporated into primer SEQ ID NO:28. The 5' end of primer SEQ ID NO:28 was the reverse complement of primer SEQ ID NO:27 to enable subsequent overlap extension PCR. The gene splicing by overlap extension technique (Horton et al., *BioTechniques*, 8:528–535, 1990) was used to generate a 2.1 kb fragment by PCR using the above two PCR fragments as templates and primers SEQ ID NO:26 and SEQ ID NO:29. This fragment represented a deletion of 0.8 kb from the central region of the 1.5 kb glpK gene. Overall, this fragment had 1.0 kb and 1.1 kb flanking regions on either side of the MunI cloning site (within the partial glpK) to allow for chromosomal gene replacement by homologous recombination.

The above 2.1 kb PCR fragment was blunt-ended (using mung bean nuclease) and cloned into the pCR-Blunt vector using the Zero Blunt PCR Cloning Kit (Invitrogen, San Diego, Calif.) to yield the 5.6 kb plasmid pRN100 containing kanamycin and Zeocin resistance genes. The 1.2 kb HincII fragment from pLoxCat1 (unpublished results), containing a chloramphenicol-resistance gene flanked by bacteriophage P1 loxP sites (Snaith et al., *Gene*, 166:173–174, 1995), was used to interrupt the glpK fragment in plasmid pRN100 by ligating it to MunI-digested (and blunt-ended) plasmid pRN100 to yield the 6.9 kb plasmid pRN101-1. A 376 bp fragment containing the R6K origin was amplified by PCR from the vector pGP704 (Miller and Mekalanos, *J. Bacteriol.*, 170:2575–2583, 1988) using primers SEQ ID NO:30 and SEQ ID NO:31, blunt-ended, and ligated to the 5.3 kb Asp718-AatII fragment (which was blunt-ended) from pRN101-1 to yield the 5.7 kb plasmid pRN102-1 containing kanamycin and chloramphenicol resistance genes. Substitution of the ColE1 origin region in pRN101-1 with the R6K origin to generate $pRN_1O_2$-1 also involved deletion of most of the Zeocin resistance gene. The host for pRN102-1 replication was *E. coli* SY327 (Miller and Mekalanos, *J. Bacteriol.*, 170:2575–2583, 1988) which contains the pir gene necessary for the function of the R6K origin.

Engineering of Glycerol Kinase Mutant RJF10m with Chloramphenicol Resistance Gene Interrupt

*E. coli* FM5 was electrotransformed with the non-replicative integration plasmid pRN102-1 and transformants that were chloramphenicol-resistant (12.5 µg/mL) and kanamycin-sensitive (30 µg/mL) were further screened for glycerol non-utilization on M9 minimal medium containing 1 mM glycerol. An EcoRI digest of genomic DNA from one such mutant, RJF10m, when probed with the intact glpK gene via Southern analysis (Southern, *J. Mol. Biol.*, 98:503–517, 1975) indicated that it was a double-crossover integrant (glpK gene replacement) since the two expected 7.9 kb and 2.0 kb bands were observed, owing to the presence of an additional EcoRI site within the chloramphenicol resistance gene. The wild-type control yielded the single expected 9.4 kb band. A $^{13}C$ NMR analysis of mutant RJF10m confirmed that it was incapable of converting $^{13}C$-labeled glycerol and ATP to glycerol-3-phosphate. This glpK mutant was further analyzed by genomic PCR using primer combinations SEQ ID NO:32 and SEQ ID NO:33, SEQ ID NO:34 and SEQ ID NO:35, and SEQ ID NO:32 and SEQ ID NO:35 which yielded the expected 2.3 kb, 2.4 kb, and 4.0 kb PCR fragments respectively. The wild-type control yielded the expected 3.5 kb band with primers SEQ ID NO:32 and SEQ ID NO:35. The glpK mutant RJF10m was electrotransformed with plasmid pAH48 to allow glycerol production from glucose. The glpK mutant *E. coli* RJF10m has been deposited with ATCC under the terms of the Budapest Treaty on 24 Nov. 1997.

Engineering of Glycerol Kinase Mutant RJF10 with Chloramphenicol Resistance Gene Interrupt Removed After overnight growth on YENB medium (0.75% yeast extract, 0.8% nutrient broth) at 37° C., *E. coli* RJF10m in a water suspension was electrotransformed with plasmid pJW168 (unpublished results), which contained the bacteriophage P1 Cre recombinase gene under the control of the IPTG-inducible lacUV5 promoter, a temperature-sensitive pSC101 replicon, and an ampicillin resistance gene. Upon outgrowth in SOC medium at 30° C., transformants were selected at 30° C. (permissive temperature for pJW168 replication) on LB agar medium supplemented with carbenicillin (50 µg/mL) and IPTG (1 mM). Two serial overnight transfers of pooled colonies were carried out at 30° C. on fresh LB agar medium supplemented with carbenicillin and IPTG in order to allow excision of the chromosomal chloramphenicol resistance gene via recombination at the loxP sites mediated by the Cre recombinase (Hoess and Abremski, *J. Mol. Biol.*, 181:351–362, 1985). Resultant colonies were replica-plated on to LB agar medium supplemented with carbenicillin and IPTG and LB agar supplemented with chloramphenicol (12.5 µg/mL) to identify colonies that were carbenicillin-resistant and chloramphenicol-sensitive indicating marker gene removal. An overnight 30° C. culture of one such colony was used to inoculate 10 mL of LB medium. Upon growth at 30° C. to OD (600 nm) of 0.6, the culture was incubated at 37° C. overnight. Several dilutions were plated on prewarmed LB agar medium and the plates incubated overnight at 42° C. (the non-permissive temperature for pJW168 replication). Resultant colonies were replica-plated on to LB agar medium and LB agar medium supplemented with carbenicillin (75 µg/mL) to identify colonies that were carbenicillin-sensitive indicating loss of plasmid pJW168. One such glpK mutant, RJF10, was further analyzed by genomic PCR using primers SEQ ID NO:32 and SEQ ID NO:35 and yielded the expected 3.0 kb band confirming marker gene excision. Glycerol non-utilization by mutant RJF10 was confirmed by lack of growth on M9 minimal medium containing 1 mM glycerol. The glpK mutant RJF10 was electrotransformed with plasmid pAH48 to allow glycerol production from glucose.

Example 6

Construction of E. coli Strain with GLDA Gene Knockout

The gldA gene was isolated from *E. coli* by PCR (K. B. Mullis and F. A. Faloona (1987) Meth. Enzymol. 155: 335–350) using primers SEQ ID NO:36 and SEQ ID NO:37, which incorporate terminal Sph1 and Xba1 sites, respectively, and cloned (T. Maniatis 1982 Molecular Cloning. A Laboratory Manual. Cold Spring Harbor, Cold Spring Harbor, N.Y.) between the Sph1 and Xba1 sites in pUC18, to generate pKP8. pKP8 was cut at the unique Sal1 and Nco1 sites within the gldA gene, the ends flushed with Klenow and religated, resulting in a 109 bp deletion in the middle of gldA and regeneration of a unique Sal1 site, to generate pKP9. A 1.4 kb DNA fragment containing the gene conferring kanamycin resistance (kan), and including about 400 bps of DNA upstream of the translational start codon and about 100 bps of DNA downstream of the translational stop codon, was isolated from pET-28a(+) (Novagen, Madison, Wis.) by PCR using primers SEQ ID NO:38 and SEQ ID NO:39, which incorporate terminal Sal1 sites, and subcloned into the unique Sal1 site of pKP9, to generate pKP13. A 2.1 kb DNA fragment beginning 204 bps downstream of the gldA translational start codon and ending 178 bps upstream of the gldA translational stop codon, and containing the kan insertion, was isolated from pKP13 by PCR using primers SEQ ID NO:40 and SEQ ID NO:41, which incorporate terminal Sph1 and Xba1 sites, respectively, was subcloned between the Sph1 and Xba1 sites in pMAK705 (Genencor International, Palo Alto, Calif.), to generate pMP33. *E. coli* FM5 was transformed with pMP33 and selected on 20 ug/mL kan at 30° C., which is the permissive temperature for pMAK705 replication. One colony was expanded overnight at 30° C. in liquid media supplemented with 20 ug/mL kan. Approximately 32,000 cells were plated on 20 ug/mL kan and incubated for 16 hrs at 44° C., which is the restrictive temperature for pMAK705 replication. Transformants growing at 44° C. have plasmid integrated into the chromosome, occuring at a frequency of approximately 0.0001. PCR and Southern blot (E. M. Southern 1975 *J. Mol. Biol.* 98:503–517) analyses were used to determine the nature of the chromosomal integration events in the transformants. Western blot analysis (H. Towbin, et al. (1979) *Proc. Natl. Acad. Sci.* 76:4350) was used to determine whether glycerol dehydrogenase protein, the product of gldA, is produced in the transformants. An activity assay was used to determine whether glycerol dehydrogenase activity remained in the transformants. Activity in glycerol dehydrogenase bands on native gels was determined by coupling the conversion of glycerol+NAD(+)→dihydroxyacetone+NADH to the conversion of a tetrazolium dye, MTT [3-(4,5-dimethylthiazol-2-yl)-2,5-diphenyltetrazolium bromide] to a deeply colored formazan, with phenazine methosulfate as mediator. Glycerol dehydrogenase also requires the presence of 30 mM ammonium sulfate and 100 mM Tris, pH 9 (C.-T. Tang, et al. (1997) *J. Bacteriol.* 140:182). Of 8 transformants analyzed, 6 were determined to be gldA knockouts. *E. coli* MSP33.6 has been deposited with ATCC under the terms of the Budapest Treaty on 24 Nov. 1997.

Example 7

Construction of E. coli Strain with GLPK and GLDA Gene Knockouts

A 1.6 kb DNA fragment containing the gldA gene, and including 228 bps of DNA upstream of the translational start codon and 220 bps of DNA downstream of the translational stop codon was isolated from E. coli by PCR using primers SEQ ID NO:42 and SEQ ID NO:43, which incorporate terminal Sph1 and Xba1 sites, repectively, and cloned between the Sph1 and Xba1 sites of pUC18, to generate pQN2. pQN2 was cut at the unique Sal1 and Nco1 sites within the gldA gene, the ends flushed with Klenow and religated, resulting in a 109 bp deletion in the middle of gldA and regeneration of a unique Sal1 site, to generate pQN4. A 1.2 kb DNA fragment containing the gene conferring kanamycin resistance (kan), and flanked by loxP sites was isolated from pLoxKan2 (Genecor International, Palo Alto, Calif.) as a Stu1/Xho1 fragment, the ends flushed with Klenow, and subcloned into pQN4 at the Sal1 site after flushing with Klenow, to generate pQN8. The Sph1/Xba1 fragment from pQN8 containing the kan-interupted gldA was subcloned between the Sph1 and Xba1 sites of pGP704, using E. coli SY327 as host, to generate pQN9. E. coli RJF10 (see EXAMPLE 5) was transformed with pQN9 and selected on kan. Since the pGP704 backbone cannot replicate in most E. coli hosts, transformants arise by integration of the plasmid, (or portions of it) into the chromosome. Double crossover integration events are determined by identifying those transformants which are kan resistant and ampicillin sensitive. PCR and Southern blot analyses are used to determine the nature of the chromosomal integration events in the transformants. Western blot analysis is used to determine whether glycerol dehydrogenase, the product of gldA, is produced in the transformants. Activity assays are used to determine whether glycerol dehydrogenase activity remains in the transformants. The kan marker is removed from the chromosome using the Cre-producing plasmid pJW168, as described in EXAMPLE 5.

Example 8

Consumption of Glycerol Produced from D-Glucose by Recombinant E. coli Containing Both GPP2 and DAR1 with and without Glycerol Kinase (GLPK) Activity EXAMPLE 8 illustrates the consumption of glycerol by the recombinant E. coli FM5/pAH48 and RJF10/pAH48. The strains FM5/pAH48 and RJF10/pAH48 were constructed as described above in the GENERAL METHODS.

Pre-Culture

FM5/pAH48 and RJF10/pAH48 were pre-cultured for seeding a fermenter in the same medium used for fermentation, or in LB supplemented with 1% glucose. Either carbenicillin or ampicillin were used (100 mg/L) for plasmid maintenance. The medium for fermentation is as described in EXAMPLE 4.

Cultures were started from frozen stocks (15% glycerol as cryoprotectant) in 600 mL medium in a 2-L Erlenmeyer flask, grown at 30° C. in a shaker at 250 rpm for approximately 12 h, and used to seed the fermenter.

Fermentation Growth

A 15-L stirred tank fermenter with 5–7 L initial volume was prepared as described in EXAMPLE 4. Either carbenicillin or ampicillin were used (100 mg/L) for plasmid maintenance.

Environmental Conditions to Evaluate Glycerol Kinase (GlpK) Activity The temperature was controlled at 30° C. and the air flow rate controlled at 6 standard liters per minute. Back pressure was controlled at 0.5 bar. Dissolved oxygen tension was controlled at 10% by stirring. Aqueous ammonia was used to control pH at 6.7. The glucose feed (60% glucose) rate was controlled to maintain excess glucose until glycerol had accumulated to at least 25 g/L. Glucose was then depleted, resulting in the net metabolism of glycerol. Table 2 shows the resulting conversion of glycerol.

TABLE 2

Conversion of glycerol by FM5/pAH48 (wt) and RJF10/pAH48 (glpK)

| Strain | number of examples | rate of glycero consumption g/OD/hr |
|---|---|---|
| FM5/pAH48 | 2 | 0.095 ± 0.015 |
| RJF10/pAH48 | 3 | 0.021 ± 0.011 |

As is seen by the data in Table 2, the rate of glycerol consumption decreases about 4–5 fold where endogenous glycerol kinase activity is eliminated.

Environmental Conditions to Evaluate Glycerol Dehydrogenase (GldA) Activity

The temperature was controlled at 30° C. and the air flow rate controlled at 6 standard liters per minute. Back pressure was controlled at 0.5 bar. Dissolved oxygen tension was controlled at 10% by stirring. Aqueous ammonia was used to control pH at 6.7. In the first fermentation, glucose was kept in excess for the duration of the fermentation. The second fermentation was operated with no residual glucose after the first 25 hours. Samples over time from the two fermentations were taken for evaluation of GlpK and GldA activities. Table 3 summarizes RJF10/pAH48 fermentations that show the effects of GldA on selectivity for glycerol.

TABLE 3

GldA and GlpK activitities from two RJF10/pAH48 fermentations

| Fermentation | Time (hrs) | GldA | GlpK | Overall selectivity (g/g) |
|---|---|---|---|---|
| 1 | 25 | − | − | 42% |
|   | 46 | − | − | 49% |
|   | 61 | + | − | 54% |
| 2 | 25 | + | − | 41% |
|   | 46 | ++ | − | 14% |
|   | 61 | ++ | − | 12% |

As is seen by the data in Table 3, the presence of glycerol dehydrogenase (GldA) activity is linked to the conversion of glycerol under glucose-limited conditions; thus, it is anticipated that eliminating glycerol dehydrogenase activity will reduce glycerol conversion.

The invention claimed is:

1. A transformed host cell comprising:
    (a) an exogenous gene encoding a protein having a glycerol-3-phosphate dehydrogenase activity;
    (b) an exogenous gene encoding a protein having glycerol-3-phosphate phosphatase activity;
    (c) a disruption in a gene encoding an endogenous glycerol kinase, wherein the disruption prevents the expression of the active gene product; and
    (d) a disruption in a gene encoding an endogenous glycerol dehydrogenase, wherein the disruption prevents the expression of the active gene product.

2. A transformed host cell comprising:
    (a) an exogenous gene encoding a protein having a glycerol-3-phosphate dehydrogenase activity;
    (b) an exogenous gene encoding a protein having glycerol-3-phosphate phosphatase activity; and
    (c) disruption in a gene encoding an endogenous glycerol dehydrogenase, wherein the disruption prevents the expression of the active gene product.

3. A transformed host cell comprising:
    (a) an exogenous gene encoding a protein having a glycerol-3-phosphate dehydrogenase activity;
    (b) an exogenous gene encoding a protein having glycerol-3-phosphate phosphatase activity; and
    (c) a disruption in a gene encoding an endogenous glycerol kinase, wherein the disruption prevents the expression of the active gene product.

4. *Escherichia coli* pAH21/DH5α designated ATCC 98187.

5. *Escherichia coli* pDAR1A/AA200, designated ATCC 98248.

6. *Escherichia coli* RJF 10m, designated ATCC 98597.

7. *Escherichia coli* mSP33.6, designated ATCC 98598.

* * * * *

SEQUENCE LISTING (1) GENERAL INFORMATION:

(iii) NUMBER OF SEQUENCES: 407

(2) INFORMATION FOR SEQ ID NO: 1:

(i) SEQUENCE CHARACTERISTICS:
       (A) LENGTH: 44 amino acids
       (B) TYPE: amino acid
       (C) STRANDEDNESS: <Unknown>
       (D) TOPOLOGY: unknown (ii) MOLECULE TYPE: peptide (xi) SEQUENCE DESCRIPTION: SEQ ID NO: 1:

Arg Ser Gly Ala Tyr Glu Ser Pro Asp Gly Arg Gly Arg Ser Tyr
1               5                   10                  15

Val Gly Gly Gly Gly Cys Gly Asn Ile Gly Arg Lys His Asn Leu
                20                  25                  30

Trp Gly Leu Arg Thr Ala Ser Pro Ala Cys Trp Asp
            35                  40

(2) INFORMATION FOR SEQ ID NO: 2:

(i) SEQUENCE CHARACTERISTICS:
       (A) LENGTH: 44 amino acids
       (B) TYPE: amino acid
       (C) STRANDEDNESS: <Unknown>
       (D) TOPOLOGY: unknown (ii) MOLECULE TYPE: peptide (xi) SEQUENCE DESCRIPTION: SEQ ID NO: 2:

Ser Pro Arg Ser Phe Trp Pro Val Val Ser Arg His Glu Ser Phe Gly
1               5                   10                  15

Ile Ser Asn Tyr Leu Gly Cys Gly Tyr Arg Thr Cys Ile Ser Gly Thr
                20                  25                  30

Met Thr Lys Ser Ser Pro Ile Tyr Pro Arg His Ser
            35                  40

(2) INFORMATION FOR SEQ ID NO: 3:

(i) SEQUENCE CHARACTERISTICS:
       (A) LENGTH: 44 amino acids
       (B) TYPE: amino acid
       (C) STRANDEDNESS: <Unknown>
       (D) TOPOLOGY: unknown (ii) MOLECULE TYPE: peptide (xi) SEQUENCE DESCRIPTION: SEQ ID NO: 3:

Ser Ser Ser Ser Asp Trp Gly Gly Val Pro Gly Lys Val Val Arg Glu
1               5                   10                  15

Arg Phe Lys Gly Arg Gly Cys Gly Ile Ser Ile Thr Ser Val Leu Thr
                20                  25                  30

Gly Lys Pro Asn Pro Cys Pro Glu Pro Lys Ala Ala
            35                  40

(2) INFORMATION FOR SEQ ID NO: 4:

(i) SEQUENCE CHARACTERISTICS:
       (A) LENGTH: 44 amino acids
       (B) TYPE: amino acid

```
        (C) STRANDEDNESS: <Unknown>
        (D) TOPOLOGY: unknown (ii) MOLECULE TYPE: peptide (xi) SEQUENCE DESCRIPTION: SEQ ID NO: 4:

Arg Val Gly Gln Cys Thr Asp Ser Asp Val Arg Arg Pro Trp Ala Arg
1               5                   10                  15

Ser Cys Ala His Gln Gly Cys Gly Ala Gly Thr Arg Asn Ser His Gly
            20                  25                  30

Cys Ile Thr Arg Pro Leu Arg Gln Ala Ser Ala His
        35                  40

(2) INFORMATION FOR SEQ ID NO: 5:

(i) SEQUENCE CHARACTERISTICS:
        (A) LENGTH: 39 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 5:

Ser His Ser Gly Gly Met Asn Arg Ala Tyr Gly Asp Val Phe Arg Glu
1               5                   10                  15

Leu Arg Asp Arg Trp Asn Ala Thr Ser His His Thr Arg Pro Thr Pro
            20                  25                  30

Gln Leu Pro Arg Gly Pro Asn
        35

(2) INFORMATION FOR SEQ ID NO: 6:

(i) SEQUENCE CHARACTERISTICS:
        (A) LENGTH: 41 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 6:

Ser Pro Cys Gly Gly Ser Trp Gly Arg Phe Met Gln Gly Gly Leu Phe
1               5                   10                  15

Gly Gly Arg Thr Asp Gly Cys Gly Ala His Arg Asn Arg Thr Ser Ala
            20                  25                  30

Ser Leu Glu Pro Pro Ser Ser Asp Tyr
        35                  40

(2) INFORMATION FOR SEQ ID NO: 7:

(i) SEQUENCE CHARACTERISTICS:
        (A) LENGTH: 39 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 7:

Arg Gly Ala Ala Asp Gln Arg Arg Gly Trp Ser Glu Asn Leu Gly Leu
1               5                   10                  15
```

```
Pro Arg Val Gly Trp Asp Ala Ile Ala His Asn Ser Tyr Thr Phe Thr
            20                  25                  30

Ser Arg Arg Pro Arg Pro Pro
            35
```

(2) INFORMATION FOR SEQ ID NO: 8:

(i) SEQUENCE CHARACTERISTICS:
        (A) LENGTH: 44 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 8:

```
Ser Gly Gly Glu Val Ser Ser Trp Gly Arg Val Asn Asp Leu Cys Ala
 1               5                  10                  15

Arg Val Ser Trp Thr Gly Cys Gly Thr Ala Arg Ser Ala Arg Thr Asp
            20                  25                  30

Asn Lys Gly Phe Leu Pro Lys His Ser Ser Leu Arg
            35                  40
```

(2) INFORMATION FOR SEQ ID NO: 9:

(i) SEQUENCE CHARACTERISTICS:
        (A) LENGTH: 44 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 9:

```
Ser Asp Ser Asp Gly Asp His Tyr Gly Leu Arg Gly Val Arg Cys
 1               5                  10                  15

Ser Leu Arg Asp Arg Gly Cys Gly Leu Ala Leu Ser Thr Val His Ala
            20                  25                  30

Gly Pro Pro Ser Phe Tyr Pro Lys Leu Ser Ser Pro
            35                  40
```

(2) INFORMATION FOR SEQ ID NO: 10:

(i) SEQUENCE CHARACTERISTICS:
        (A) LENGTH: 39 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 10:

```
Arg Ser Leu Gly Asn Tyr Gly Val Thr Gly Thr Val Asp Val Thr Val
 1               5                  10                  15

Leu Pro Met Pro Gly His Ala Asn His Leu Gly Val Ser Ser Ala Ser
            20                  25                  30

Ser Ser Asp Pro Pro Arg Arg
            35
```

(2) INFORMATION FOR SEQ ID NO: 11:

(i) SEQUENCE CHARACTERISTICS:
        (A) LENGTH: 38 amino acids
        (B) TYPE: amino acid

```
           (C) STRANDEDNESS: <Unknown>
           (D) TOPOLOGY: unknown (ii) MOLECULE TYPE: peptide (xi) SEQUENCE DESCRIPTION: SEQ ID NO: 11:

Arg Thr Thr Thr Ala Lys Gly Cys Leu Leu Gly Ser Phe Gly Val Leu
1               5                  10                  15

Ser Gly Cys Ser Phe Thr Pro Thr Ser Pro Pro Pro His Leu Gly Tyr
            20                  25                  30

Pro Pro His Ser Val Asn
        35

(2) INFORMATION FOR SEQ ID NO: 12:

(i) SEQUENCE CHARACTERISTICS:
           (A) LENGTH: 39 amino acids
           (B) TYPE: amino acid
           (C) STRANDEDNESS: <Unknown>
           (D) TOPOLOGY: unknown (ii) MOLECULE TYPE: peptide (xi) SEQUENCE DESCRIPTION: SEQ ID NO: 12:

Ser Pro Lys Leu Ser Ser Val Gly Val Met Thr Lys Val Thr Glu Leu
1               5                  10                  15

Pro Thr Glu Gly Pro Asn Ala Ile Ser Ile Pro Ile Ser Ala Thr Leu
            20                  25                  30

Gly Pro Arg Asn Pro Leu Arg
        35

(2) INFORMATION FOR SEQ ID NO: 13:

(i) SEQUENCE CHARACTERISTICS:
           (A) LENGTH: 39 amino acids
           (B) TYPE: amino acid
           (C) STRANDEDNESS: <Unknown>
           (D) TOPOLOGY: unknown (ii) MOLECULE TYPE: peptide (xi) SEQUENCE DESCRIPTION: SEQ ID NO: 13:

Arg Trp Cys Gly Ala Glu Leu Cys Asn Ser Val Thr Lys Lys Phe Arg
1               5                  10                  15

Pro Gly Trp Arg Asp His Ala Asn Pro Ser Thr His His Arg Thr Pro
            20                  25                  30

Pro Pro Ser Gln Ser Ser Pro
        35

(2) INFORMATION FOR SEQ ID NO: 14:

(i) SEQUENCE CHARACTERISTICS:
           (A) LENGTH: 44 amino acids
           (B) TYPE: amino acid
           (C) STRANDEDNESS: <Unknown>
           (D) TOPOLOGY: unknown (ii) MOLECULE TYPE: peptide (xi) SEQUENCE DESCRIPTION: SEQ ID NO: 14:

Arg Trp Cys Gly Ala Asp Asp Pro Cys Gly Ala Ser Arg Trp Arg Gly
1               5                  10                  15
```

-continued

Gly Asn Ser Leu Phe Gly Cys Gly Leu Arg Cys Ser Ala Ala Gln Ser
                20                  25                  30

Thr Pro Ser Gly Arg Ile His Ser Thr Ser Thr Ser
        35                  40

(2) INFORMATION FOR SEQ ID NO: 15:

(i) SEQUENCE CHARACTERISTICS:
        (A) LENGTH: 39 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 15:

Ser Lys Ser Gly Glu Gly Gly Asp Ser Ser Arg Gly Glu Thr Gly Trp
 1               5                  10                  15

Ala Arg Val Arg Ser His Ala Met Thr Ala Gly Arg Phe Arg Trp Tyr
                20                  25                  30

Asn Gln Leu Pro Ser Asp Arg
        35

(2) INFORMATION FOR SEQ ID NO: 16:

(i) SEQUENCE CHARACTERISTICS:
        (A) LENGTH: 38 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 16:

Arg Ser Ser Ala Asn Asn Cys Glu Trp Lys Ser Asp Trp Met Arg Arg
 1               5                  10                  15

Ala Cys Ile Ala Arg Tyr Ala Asn Ser Ser Gly Pro Ala Arg Ala Val
                20                  25                  30

Asp Thr Lys Ala Ala Pro
        35

(2) INFORMATION FOR SEQ ID NO: 17:

(i) SEQUENCE CHARACTERISTICS:
        (A) LENGTH: 44 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 17:

Ser Lys Trp Ser Trp Ser Ser Arg Trp Gly Ser Pro Gln Asp Lys Val
 1               5                  10                  15

Glu Lys Thr Arg Ala Gly Cys Gly Gly Ser Pro Ser Ser Thr Asn Cys
                20                  25                  30

His Pro Tyr Thr Phe Ala Pro Pro Gln Ala Gly
        35                  40

(2) INFORMATION FOR SEQ ID NO: 18:

(i) SEQUENCE CHARACTERISTICS:
        (A) LENGTH: 44 amino acids
        (B) TYPE: amino acid (C) STRANDEDNESS: <Unknown>
        (D) TOPOLOGY: unknown (ii) MOLECULE TYPE: peptide (xi) SEQUENCE DESCRIPTION: SEQ ID NO: 18:

Ser Gly Phe Trp Glu Phe Ser Arg Gly Leu Trp Asp Gly Glu Asn Arg
 1               5                  10                  15

Lys Ser Val Arg Ser Gly Cys Gly Phe Arg Gly Ser Ser Ala Gln Gly
            20                  25                  30

Pro Cys Pro Val Thr Pro Ala Thr Ile Asp Lys His
        35                  40

(2) INFORMATION FOR SEQ ID NO: 19:

(i) SEQUENCE CHARACTERISTICS:
        (A) LENGTH: 44 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 19:

Ser Glu Ser Gly Arg Cys Arg Ser Val Ser Arg Trp Met Thr Thr Trp
 1               5                  10                  15

Gln Thr Gln Lys Gly Gly Cys Gly Ser Asn Val Ser Arg Gly Ser Pro
            20                  25                  30

Leu Asp Pro Ser His Gln Thr Gly His Ala Thr Thr
        35                  40

(2) INFORMATION FOR SEQ ID NO: 20:

(i) SEQUENCE CHARACTERISTICS:
        (A) LENGTH: 39 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 20:

Arg Glu Trp Arg Phe Ala Gly Pro Pro Leu Asp Leu Trp Ala Gly Pro
 1               5                  10                  15

Ser Leu Pro Ser Phe Asn Ala Ser Ser His Pro Arg Ala Leu Arg Thr
            20                  25                  30

Tyr Trp Ser Gln Arg Pro Arg
        35

(2) INFORMATION FOR SEQ ID NO: 21:

(i) SEQUENCE CHARACTERISTICS:
        (A) LENGTH: 44 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 21:

Arg Met Glu Asp Ile Lys Asn Ser Gly Trp Arg Asp Ser Cys Arg Trp
 1               5                  10                  15

```
Gly Asp Leu Arg Pro Gly Cys Gly Ser Arg Gln Trp Tyr Pro Ser Asn
            20                  25                  30

Met Arg Ser Ser Arg Asp Tyr Pro Ala Gly Gly His
        35                  40

(2) INFORMATION FOR SEQ ID NO: 22:

(i) SEQUENCE CHARACTERISTICS:
        (A) LENGTH: 36 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 22:

Ser His Pro Trp Tyr Arg His Trp Asn His Gly Asp Phe Ser Gly Ser
  1               5                  10                  15

Gly Gln Ser Arg His Thr Pro Pro Glu Ser Pro His Pro Gly Arg Pro
            20                  25                  30

Asn Ala Thr Ile
        35

(2) INFORMATION FOR SEQ ID NO: 23:

(i) SEQUENCE CHARACTERISTICS:
        (A) LENGTH: 44 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 23:

Arg Tyr Lys His Asp Ile Gly Cys Asp Ala Gly Val Asp Lys Lys Ser
  1               5                  10                  15

Ser Ser Val Arg Gly Gly Cys Gly Ala His Ser Ser Pro Pro Arg Ala
            20                  25                  30

Gly Arg Gly Pro Arg Gly Thr Met Val Ser Arg Leu
        35                  40

(2) INFORMATION FOR SEQ ID NO: 24:

(i) SEQUENCE CHARACTERISTICS:
        (A) LENGTH: 44 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 24:

Ser Gln Gly Ser Lys Gln Cys Met Gln Tyr Arg Thr Gly Arg Leu Thr
  1               5                  10                  15

Val Gly Ser Glu Tyr Gly Cys Gly Met Asn Pro Ala Arg His Ala Thr
            20                  25                  30

Pro Ala Tyr Pro Ala Arg Leu Leu Pro Arg Tyr Arg
        35                  40

(2) INFORMATION FOR SEQ ID NO: 25:

(i) SEQUENCE CHARACTERISTICS:
        (A) LENGTH: 44 amino acids
        (B) TYPE: amino acid
```

```
        (C) STRANDEDNESS: <Unknown>
        (D) TOPOLOGY: unknown (ii) MOLECULE TYPE: peptide (xi) SEQUENCE DESCRIPTION: SEQ ID NO: 25:

Ser Gly Arg Thr Thr Ser Glu Ile Ser Gly Leu Trp Gly Trp Gly Asp
1               5                   10                  15

Asp Arg Ser Gly Tyr Gly Trp Gly Asn Thr Leu Arg Pro Asn Tyr Ile
            20                  25                  30

Pro Tyr Arg Gln Ala Thr Asn Arg His Arg Tyr Thr
        35                  40

(2) INFORMATION FOR SEQ ID NO: 26:

(i) SEQUENCE CHARACTERISTICS:
        (A) LENGTH: 39 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 26:

Arg Trp Asn Trp Thr Val Leu Pro Ala Thr Gly Gly His Tyr Trp Thr
1               5                   10                  15

Arg Ser Thr Asp Tyr His Ala Ile Asn Asn His Arg Pro Ser Ile Pro
            20                  25                  30

His Gln His Pro Thr Pro Ile
        35

(2) INFORMATION FOR SEQ ID NO: 27:

(i) SEQUENCE CHARACTERISTICS:
        (A) LENGTH: 44 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 27:

Ser Trp Ser Ser Trp Asn Trp Ser Ser Lys Thr Thr Arg Leu Gly Asp
1               5                   10                  15

Arg Ala Thr Arg Glu Gly Cys Gly Pro Ser Gln Ser Asp Gly Cys Pro
            20                  25                  30

Tyr Asn Gly Arg Leu Thr Thr Val Lys Pro Arg Thr
        35                  40

(2) INFORMATION FOR SEQ ID NO: 28:

(i) SEQUENCE CHARACTERISTICS:
        (A) LENGTH: 37 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 28:

Ser Gly Ser Leu Asn Ala Trp Gln Pro Arg Ser Trp Val Gly Gly Ala
1               5                   10                  15
```

```
Phe Arg Ser His Ala Asn Asn Asn Leu Asn Pro Lys Pro Thr Met Val
            20                  25                  30

Thr Arg His Pro Thr
            35

(2) INFORMATION FOR SEQ ID NO: 29:

(i) SEQUENCE CHARACTERISTICS:
        (A) LENGTH: 44 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 29:

Arg Tyr Ser Gly Leu Ser Pro Arg Asp Asn Gly Pro Ala Cys Ser Gln
  1               5                  10                  15

Glu Ala Thr Leu Glu Gly Cys Gly Ala Gln Arg Leu Met Ser Thr Arg
            20                  25                  30

Arg Lys Gly Arg Asn Ser Arg Pro Gly Trp Thr Leu
            35                  40

(2) INFORMATION FOR SEQ ID NO: 30:

(i) SEQUENCE CHARACTERISTICS:
        (A) LENGTH: 39 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 30:

Ser Val Gly Asn Asp Lys Thr Ser Arg Pro Val Ser Phe Tyr Gly Arg
  1               5                  10                  15

Val Ser Asp Leu Trp Asn Ala Ser Leu Met Pro Lys Arg Thr Pro Ser
            20                  25                  30

Ser Lys Arg His Asp Asp Gly
            35

(2) INFORMATION FOR SEQ ID NO: 31:

(i) SEQUENCE CHARACTERISTICS:
        (A) LENGTH: 38 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 31:

Arg Trp Pro Ser Val Gly Tyr Lys Gly Asn Gly Ser Asp Thr Ile Asp
  1               5                  10                  15

Val His Ser Asn Asp Ala Ser Thr Lys Arg Ser Leu Ile Tyr Asn His
            20                  25                  30

Arg Arg Pro Leu Phe Pro
            35

(2) INFORMATION FOR SEQ ID NO: 32:

(i) SEQUENCE CHARACTERISTICS:
        (A) LENGTH: 39 amino acids
        (B) TYPE: amino acid
```

```
        (C) STRANDEDNESS: <Unknown>
        (D) TOPOLOGY: unknown (ii) MOLECULE TYPE: peptide (xi) SEQUENCE DESCRIPTION: SEQ ID NO: 32:

Arg Thr Phe Glu Asn Asp Gly Leu Gly Val Gly Arg Ser Ile Gln Lys
1               5                  10                  15

Lys Ser Asp Arg Trp Tyr Ala Ser His Asn Ile Arg Ser His Phe Ala
            20                  25                  30

Ser Met Ser Pro Ala Gly Lys
        35

(2) INFORMATION FOR SEQ ID NO: 33:

(i) SEQUENCE CHARACTERISTICS:
        (A) LENGTH: 44 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 33:

Ser Tyr Cys Arg Val Lys Gly Gly Glu Gly Gly His Thr Asp Ser
1               5                  10                  15

Asn Leu Ala Arg Ser Gly Cys Gly Lys Val Ala Arg Thr Ser Arg Leu
            20                  25                  30

Gln His Ile Asn Pro Arg Ala Thr Pro Pro Ser Arg
        35                  40

(2) INFORMATION FOR SEQ ID NO: 34:

(i) SEQUENCE CHARACTERISTICS:
        (A) LENGTH: 39 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 34:

Ser Trp Thr Arg Trp Gly Lys His Thr His Gly Gly Phe Val Asn Lys
1               5                  10                  15

Ser Pro Pro Gly Lys Asn Ala Thr Ser Pro Tyr Thr Asp Ala Gln Leu
            20                  25                  30

Pro Ser Asp Gln Gly Pro Pro
        35

(2) INFORMATION FOR SEQ ID NO: 35:

(i) SEQUENCE CHARACTERISTICS:
        (A) LENGTH: 44 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 35:

Ser Gln Val Asp Ser Phe Arg Asn Ser Phe Arg Trp Tyr Glu Pro Ser
1               5                  10                  15
```

```
Arg Ala Leu Cys His Gly Cys Gly Lys Arg Asp Thr Ser Thr Thr Arg
            20                  25                  30

Ile His Asn Ser Pro Ser Asp Ser Tyr Pro Thr Arg
            35                  40
```

(2) INFORMATION FOR SEQ ID NO: 36:

(i) SEQUENCE CHARACTERISTICS:
        (A) LENGTH: 39 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 36:

```
Ser Phe Leu Arg Phe Gln Ser Pro Arg Phe Glu Asp Tyr Ser Arg Thr
 1               5                  10                  15

Ile Ser Arg Leu Arg Asn Ala Thr Asn Pro Ser Asn Val Ser Asp Ala
            20                  25                  30

His Asn Asn Arg Ala Leu Ala
            35
```

(2) INFORMATION FOR SEQ ID NO: 37:

(i) SEQUENCE CHARACTERISTICS:
        (A) LENGTH: 39 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 37:

```
Arg Ser Ile Thr Asp Gly Gly Ile Asn Glu Val Asp Leu Ser Ser Val
 1               5                  10                  15

Ser Asn Val Leu Glu Asn Ala Asn Ser His Arg Ala Tyr Arg Lys His
            20                  25                  30

Arg Pro Thr Leu Lys Arg Pro
            35
```

(2) INFORMATION FOR SEQ ID NO: 38:

(i) SEQUENCE CHARACTERISTICS:
        (A) LENGTH: 44 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 38:

```
Ser Ser Lys Val Ser Ser Pro Arg Asp Pro Thr Val Pro Arg Lys Gly
 1               5                  10                  15

Gly Asn Val Asp Tyr Gly Cys Gly His Arg Ser Ser Ala Arg Met Pro
            20                  25                  30

Thr Ser Ala Leu Ser Ser Ile Thr Lys Cys Tyr Thr
            35                  40
```

(2) INFORMATION FOR SEQ ID NO: 39:

(i) SEQUENCE CHARACTERISTICS:
        (A) LENGTH: 44 amino acids
        (B) TYPE: amino acid

```
        (C) STRANDEDNESS: <Unknown>
        (D) TOPOLOGY: unknown (ii) MOLECULE TYPE: peptide (xi) SEQUENCE DESCRIPTION: SEQ ID NO: 39:

Arg Ala Ser Thr Gln Gly Gly Arg Gly Val Ala Pro Glu Phe Gly Ala
1               5                   10                  15

Ser Val Leu Gly Arg Gly Cys Gly Ser Ala Thr Tyr Tyr Thr Asn Ser
            20                  25                  30

Thr Ser Cys Lys Asp Ala Met Gly His Asn Tyr Ser
        35                  40

(2) INFORMATION FOR SEQ ID NO: 40:

(i) SEQUENCE CHARACTERISTICS:
        (A) LENGTH: 39 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 40:

Arg Trp Cys Glu Lys His Lys Phe Thr Ala Ala Arg Cys Ser Ala Gly
1               5                   10                  15

Ala Gly Phe Glu Arg Asp Ala Ser Arg Pro Pro Gln Pro Ala His Arg
            20                  25                  30

Asp Asn Thr Asn Arg Asn Ala
        35

(2) INFORMATION FOR SEQ ID NO: 41:

(i) SEQUENCE CHARACTERISTICS:
        (A) LENGTH: 39 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 41:

Ser Phe Gln Val Tyr Pro Asp His Gly Leu Glu Arg His Ala Leu Asp
1               5                   10                  15

Gly Thr Gly Pro Leu Tyr Ala Met Pro Gly Arg Trp Ile Arg Ala Arg
            20                  25                  30

Pro Gln Asn Arg Asp Arg Gln
        35

(2) INFORMATION FOR SEQ ID NO: 42:

(i) SEQUENCE CHARACTERISTICS:
        (A) LENGTH: 38 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 42:

Ser Arg Cys Thr Asp Asn Glu Gln Cys Pro Asp Thr Gly Thr Arg Ser
1               5                   10                  15
```

```
Arg Ser Val Ser Asn Ala Arg Tyr Phe Ser Ser Arg Leu Leu Lys Thr
            20                  25                  30

His Ala Pro His Arg Pro
        35

(2) INFORMATION FOR SEQ ID NO: 43:

(i) SEQUENCE CHARACTERISTICS:
        (A) LENGTH: 39 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 43:

Ser Ala Arg Asp Ser Gly Pro Ala Glu Asp Gly Ser Arg Ala Val Arg
1               5                   10                  15

Leu Asn Gly Val Glu Asn Ala Asn Thr Arg Lys Ser Ser Arg Ser Asn
            20                  25                  30

Pro Arg Gly Arg Arg His Pro
        35

(2) INFORMATION FOR SEQ ID NO: 44:

(i) SEQUENCE CHARACTERISTICS:
        (A) LENGTH: 44 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 44:

Ser Ser Ala Asp Ala Glu Lys Cys Ala Gly Ser Leu Leu Trp Trp Gly
1               5                   10                  15

Arg Gln Asn Asn Ser Gly Cys Gly Ser Pro Thr Lys Lys His Leu Lys
            20                  25                  30

His Arg Asn Arg Ser Gln Thr Ser Ser Ser Ser His
        35                  40

(2) INFORMATION FOR SEQ ID NO: 45:

(i) SEQUENCE CHARACTERISTICS:
        (A) LENGTH: 39 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 45:

Arg Pro Lys Asn Val Ala Asp Ala Tyr Ser Ser Gln Asp Gly Ala Ala
1               5                   10                  15

Ala Glu Glu Thr Ser His Ala Ser Asn Ala Ala Arg Lys Ser Pro Lys
            20                  25                  30

His Lys Pro Leu Arg Arg Pro
        35

(2) INFORMATION FOR SEQ ID NO: 46:

(i) SEQUENCE CHARACTERISTICS:
        (A) LENGTH: 39 amino acids
        (B) TYPE: amino acid
```

```
            (C) STRANDEDNESS: <Unknown>
            (D) TOPOLOGY: unknown (ii) MOLECULE TYPE: peptide (xi) SEQUENCE DESCRIPTION: SEQ ID NO: 46:

Arg Gly Ser Thr Gly Thr Ala Gly Gly Glu Arg Ser Gly Val Leu Asn
 1               5                  10                  15

Leu His Thr Arg Asp Asn Ala Ser Gly Ser Gly Phe Lys Pro Trp Tyr
                20                  25                  30

Pro Ser Asn Arg Gly His Lys
                35

(2) INFORMATION FOR SEQ ID NO: 47:

(i) SEQUENCE CHARACTERISTICS:
            (A) LENGTH: 39 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 47:

Arg Trp Gly Trp Glu Arg Ser Pro Ser Asp Tyr Asp Ser Asp Met Asp
 1               5                  10                  15

Leu Gly Ala Arg Arg Tyr Ala Thr Arg Thr His Arg Ala Pro Pro Arg
                20                  25                  30

Val Leu Lys Ala Pro Leu Pro
                35

(2) INFORMATION FOR SEQ ID NO: 48:

(i) SEQUENCE CHARACTERISTICS:
            (A) LENGTH: 44 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 48:

Arg Gly Trp Lys Cys Glu Gly Ser Gln Ala Ala Tyr Gly Asp Lys Asp
 1               5                  10                  15

Ile Gly Arg Ser Arg Gly Cys Gly Ser Ile Thr Lys Asn Asn Thr Asn
                20                  25                  30

His Ala His Pro Ser His Gly Ala Val Ala Lys Ile
                35                  40

(2) INFORMATION FOR SEQ ID NO: 49:

(i) SEQUENCE CHARACTERISTICS:
            (A) LENGTH: 39 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 49:

Ser Arg Glu Glu Ala Asn Trp Asp Gly Tyr Lys Arg Glu Met Ser His
 1               5                  10                  15
```

-continued

```
Arg Ser Arg Phe Trp Asp Ala Thr His Leu Ser Arg Pro Arg Arg Pro
            20                  25                  30
Ala Asn Ser Gly Asp Pro Asn
        35
```

(2) INFORMATION FOR SEQ ID NO: 50:

(i) SEQUENCE CHARACTERISTICS:
        (A) LENGTH: 44 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 50:

```
Glu Trp Tyr Ser Trp Lys Arg Ser Ser Lys Ser Thr Gly Leu Gly Asp
1               5                   10                  15
Thr Ala Thr Arg Glu Gly Cys Gly Pro Ser Gln Ser Asp Gly Cys Pro
            20                  25                  30
Tyr Asn Gly Arg Leu Thr Thr Val Lys Pro Arg Lys
        35                  40
```

(2) INFORMATION FOR SEQ ID NO: 51:

(i) SEQUENCE CHARACTERISTICS:
        (A) LENGTH: 44 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 51:

```
Arg Glu Phe Ala Glu Arg Arg Leu Trp Gly Cys Asp Asp Leu Ser Trp
1               5                   10                  15
Arg Leu Asp Ala Glu Gly Cys Gly Pro Thr Pro Ser Asn Arg Ala Val
            20                  25                  30
Lys His Arg Lys Pro Arg Pro Arg Ser Pro Ala Leu
        35                  40
```

(2) INFORMATION FOR SEQ ID NO: 52:

(i) SEQUENCE CHARACTERISTICS:
        (A) LENGTH: 44 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 52:

```
Ser Asp His Ala Leu Gly Thr Asn Leu Arg Ser Asp Asn Ala Lys Glu
1               5                   10                  15
Pro Gly Asp Tyr Asn Cys Cys Gly Asn Gly Asn Ser Thr Gly Arg Lys
            20                  25                  30
Val Phe Asn Arg Arg Arg Pro Ser Ala Ile Pro Thr
        35                  40
```

(2) INFORMATION FOR SEQ ID NO: 53:

(i) SEQUENCE CHARACTERISTICS:
        (A) LENGTH: 44 amino acids
        (B) TYPE: amino acid (C) STRANDEDNESS: <Unknown>
        (D) TOPOLOGY: unknown (ii) MOLECULE TYPE: peptide (xi) SEQUENCE DESCRIPTION: SEQ ID NO: 53:

Arg His Ile Ser Glu Tyr Ser Phe Ala Asn Ser His Leu Met Gly Gly
1               5                   10                  15

Glu Ser Lys Arg Lys Gly Cys Gly Ile Asn Gly Ser Phe Ser Pro Thr
            20                  25                  30

Cys Pro Arg Ser Pro Thr Pro Ala Phe Arg Arg Thr
        35                  40

(2) INFORMATION FOR SEQ ID NO: 54:

(i) SEQUENCE CHARACTERISTICS:
        (A) LENGTH: 38 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 54:

Ser Arg Glu Ser Gly Met Trp Gly Ser Trp Trp Arg Gly His Arg Leu
1               5                   10                  15

Asn Ser Thr Gly Gly Asn Ala Asn Met Asn Ala Ser Leu Pro Pro Asp
            20                  25                  30

Pro Pro Val Ser Thr Pro
        35

(2) INFORMATION FOR SEQ ID NO: 55:

(i) SEQUENCE CHARACTERISTICS:
        (A) LENGTH: 39 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 55:

Ser Thr Pro Pro Ser Arg Glu Ala Tyr Ser Arg Pro Tyr Ser Val Asp
1               5                   10                  15

Ser Asp Ser Asp Thr Asn Ala Lys His Ser Ser His Asn Arg Arg Leu
            20                  25                  30

Arg Thr Arg Ser Arg Pro Asn
        35

(2) INFORMATION FOR SEQ ID NO: 56:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 56:

TCTCACTCCT CGAGATCCGG CGCTTATGAG AGTCCGGATG GTCGGGGGGG TCGGAGCTAT      60

GTGGGGGGCG GGGGTGGNTG TGGTAACATT GGTCGGAAGC ATAACCTGTG GGGGCTGCGT     120

ACCGCGTCGC CGGCCTGCTG GGACTCTAGA ATCGAAGGTC GCGCTAGACC TTCGAGA       177

(2) INFORMATION FOR SEQ ID NO: 57:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 57:

```
TCTCACTCCT CGAGTCCTCG CTCTTTCTGG CCCGTTGTGT CCCGGCATGA GTCGTTTGGG      60

ATCTCTAACT ATTTGGGNTG TGGTTATCGT ACATGTATCT CCGGCACGAT GACTAAGTCT     120

AGCCCGATTT ACCCTCGGCA TTCGTCTAGA ATCGAAGGTC GCGCTAGACC TTCGAGA       177
```

(2) INFORMATION FOR SEQ ID NO: 58:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 58:

```
TCTCACTCCT CGAGTAGTAG CTCCGATTGG GGTGGTGTGC CTGGGAAGGT GGTTAGGGAG      60

CGCTTTAAGG GGCGCGGTTG TGGTATTTCC ATCACCTCCG TGCTCACTGG GAAGCCCAAT     120

CCGTGTCCGG AGCCTAAGGC GGCCTCTAGA ATCGAAGGTC GCGCTAGACC TTCGAGA       177
```

(2) INFORMATION FOR SEQ ID NO: 59:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 59:

```
TCTCACTCCT CGAGAGTTGG CCAGTGCACG GATTCTGATG TGCGGCGTCC TTGGGCCAGG      60

TCTTGCGCTC ATCAGGGTTG TGGTGCGGGC ACTCGCAACT CGCACGGCTG CATCACCCGT     120

CCTCTCCGCC AGGCTAGCGC TCATTCTAGA ATCGAAGGTC GCGCTAGACC TTCGAGA       177
```

(2) INFORMATION FOR SEQ ID NO: 60:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 60:

```
TCTCACTCCT CGAGCCACTC CGGTGGTATG AATAGGGCCT ACGGGATGT GTTTAGGGAG       60

CTTCGTGATC GGTGGAACGC CACTTCCCAC CACACTCGCC CCACCCCTCA GCTCCCCCGT     120

GGGCCTAATT CTAGAATCGA AGGTCGCGCT AGACCTTCGA GA                         162
```

(2) INFORMATION FOR SEQ ID NO: 61:

(i) SEQUENCE CHARACTERISTICS:
        (A) LENGTH: 168 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 61:

```
TCTCACTCCT CGAGTCCGTG CGGGGGGTCG TGGGGGCGTT TTATGCAGGG TGGCCTTTTC      60

GGCGGTAGGA CTGATGGTTG TGGTGCCCAT AGAAACCGCA CTTCTGCGTC GTTAGAGCCC     120

CCGAGCAGCG ACTACTCTAG AATCGAAGGT CGCGCTAGAC CTTCGAGA                  168
```

(2) INFORMATION FOR SEQ ID NO: 62:

(i) SEQUENCE CHARACTERISTICS:
        (A) LENGTH: 135 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 62:

```
TCTCACTCCT CGAGGGGCGC CGCCGATCAG CGGCGGGGGT GGTCCGAGAA CTTGGGGTTG      60

CCTAGGGTGG GGTGGGACGC CATCGCTCAC AATAGCTATA CGTTCACCTC GCGCCGCCCG     120

CGCCCCCCCT CTAGA                                                     135
```

(2) INFORMATION FOR SEQ ID NO: 63:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 63:

```
TCTCACTCCT CGAGCGGTGG GGAGGTCAGC TCCTGGGGCC GCGTGAATGA CCTCTGCGCT      60

AGGGTGAGTT GGACTGGTTG TGGTACTGCT CGTTCCGCGC GTACCGACAA CAAAGGCTTT     120

CTTCCTAAGC ACTCGTCACT CCGCTCTAGA ATCGAAGGTC GCGCTAGACC TTCGAGA        177
```

(2) INFORMATION FOR SEQ ID NO: 64:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 64:

```
TCTCACTCCT CGAGTGATAG TGACGGGGAT CATTATGGGC TTCGGGGGGG GGTGCGTTGT      60

TCGCTTCGTG ATAGGGGTTG TGGTCTGGCC CTGTCCACCG TCCATGCTGG TCCCCCCTCT     120

TTTTACCCCA AGCTCTCCAG CCCCTCTAGA ATCGAAGGTC GCGCTAGACC TTCGAGA        177
```

(2) INFORMATION FOR SEQ ID NO: 65:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 65:

```
TCTCACTCCT CGAGGAGCTT GGGTAATTAT GGCGTCACCG GGACTGTGGA CGTGACGGTT      60

TTGCCCATGC CTGGCCACGC CAACCACCTT GGTGTCTCCT CCGCCTCTAG CTCTGATCCT     120

CCGCGGCGCT CTAGAATCGA AGGTCGCGCT AGACCTTCGA GA                       162
```

(2) INFORMATION FOR SEQ ID NO: 66:

(i) SEQUENCE CHARACTERISTICS:
        (A) LENGTH: 159 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 66:

```
TCTCACTCCT CGAGAACTAC GACGGCTAAG GGGTGTCTTC TCGGAAGCTT CGGCGTTCTT      60

AGTGGGTGCT CATTTACGCC AACCTCTCCA CCGCCCCACC TAGGATACCC CCCCCACTCC     120

GTCAATTCTA GAATCGAAGG TCGCGCTAGA CCTTCGAGA                            159
```

(2) INFORMATION FOR SEQ ID NO: 67:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 67:

```
TCTCACTCCT CGAGCCCGAA GTTGTCCAGC GTGGGTGTTA TGACTAAGGT CACGGAGCTG      60

CCCACGGAGG GGCCTAACGC CATTAGTATT CCGATCTCCG CGACCCTCGG CCCGCGCAAC     120

CCGCTCCGCT CTAGAATCGA AGGTCGCGCT AGACCTTCGA GA                       162
```

(2) INFORMATION FOR SEQ ID NO: 68:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 68:

```
TCTCACTCCT CGAGGTGGTG CGGCGCTGAG CTGTGCAACT CGGTGACTAA GAAGTTTCGC      60

CCGGGCTGGC GGGATCACGC CAATCCCTCC ACCCATCATC GTACTCCCCC GCCCAGCCAG     120

TCCAGCCCTT CTAGAATCGA AGGTCGCGCT AGACCTTCGA GA                       162
```

(2) INFORMATION FOR SEQ ID NO: 69:

(i) SEQUENCE CHARACTERISTICS:
        (A) LENGTH: 176 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 69:

```
TCTCACTCCT CGAGGTGGTG CGGCGCTGAT GACCCGTGTG GTGCCAGTCG TTGGCGGGGG      60

GGCAACAGCT TGTTTGGTTG TGGTCTTCGT TGTAGTGCGG CGCAGAGCAC CCCGAGTGGC     120

AGGATCCATT CCACTTCGAC CAGCTCTAGA ATCGAAGGTG CGCTAGACCT TCGAGA         176
```

(2) INFORMATION FOR SEQ ID NO: 70:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 70:

```
TCTCACTCCT CGAGTAAGTC CGGGGAGGGG GGTGACAGTA GCAGGGGCGA GACGGGCTGG      60

GCGAGGGTTC GGTCTCACGC CATGACTGCT GGCCGCTTTC GGTGGTACAA CCAGTTGCCC     120

TCTGATCGGT CTAGAATCGA AGGTCGCGCT AGACCTTCGA GA                        162
```

(2) INFORMATION FOR SEQ ID NO: 71:

(i) SEQUENCE CHARACTERISTICS:
        (A) LENGTH: 159 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 71:

```
TCTCACTCCT CGAGGTCGAG CGCCAATAAT TGCGAGTGGA AGTCTGATTG GATGCGCAGG      60

GCCTGTATTG CTCGTTACGC CAACAGTTCG GGCCCCGCCC GCGCCGTCGA CACTAAGGCC     120

GCGCCCTCTA GAATCGAAGG TCGCGCTAGA CCTTCGAGA                            159
```

(2) INFORMATION FOR SEQ ID NO: 72:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 72:

```
TCTCACTCCT CGAGTAAGTG GTCGTGGAGT TCGAGGTGGG GCTCCCCGCA GGATAAGGTT      60

GAGAAGACCA GGGCGGGTTG TGGTGGTAGT CCCAGCAGCA CCAATTGTCA CCCCTACACC     120

TTTGCCCCCC CCCCGCAAGC CGGCTCTAGA ATCGAAGGTC GCGCTAGACC TTCGAGA        177
```

(2) INFORMATION FOR SEQ ID NO: 73:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 73:

```
TCTCACTCCT CGAGTGGGTT CTGGGAGTTT AGCAGGGGGC TTTGGGATGG GGAGAACCGT      60
AAGAGTGTCC GGTCGGGTTG TGGTTTTCGT GGCTCCTCTG CTCAGGGCCC GTGTCCGGTC     120
ACGCCTGCCA CCATTGACAA ACACTCTAGA ATCGAAGGTC GCGCTAGACC TTCGAGA       177
```

(2) INFORMATION FOR SEQ ID NO: 74:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 74:

```
TCTCACTCCT CGAGTGAGAG CGGGCGGTGC CGTAGCGTGA GCCGGTGGAT GACGACGTGG      60
CAGACGCAGA AGGGCGGTTG TGGTTCCAAT GTTTCCCGCG GTTCGCCCCT CGACCCCTCT     120
CACCAGACCG GGCATGCCAC TACTTCTAGA ATCGAAGGTC GCGCTAGACC TTCGAGA       177
```

(2) INFORMATION FOR SEQ ID NO: 75:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 75:

```
TCTCACTCCT CGAGGGAGTG GAGGTTTGCC GGGCCGCCGT TGGACCTGTG GGCGGGTCCG      60
AGCTTGCCCT CTTTTAACGC CAGTTCCCAC CCTCGCGCCC TGCGCACCTA TTGGTCCCAG     120
CGGCCCCGCT CTAGAATCGA AGGTCGCGCT AGACCTTCGA GA                       162
```

(2) INFORMATION FOR SEQ ID NO: 76:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 76:

```
TCTCACTCCT CGAGGATGGA GGACATCAAG AACTCGGGGT GGAGGGACTC TTGTAGGTGG      60
GGTGACCTGA GGCCTGGTTG TGGTAGCCGC CAGTGGTACC CCTCGAATAT GCGTTCTAGC     120
AGAGATTACC CCGCGGGGGG CCACTCTAGA ATCGAAGGTC GCGCTAGACC TTCGAGA       177
```

(2) INFORMATION FOR SEQ ID NO: 77:

(i) SEQUENCE CHARACTERISTICS:
        (A) LENGTH: 152 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 77:

```
TCTCACTCCT CGAGTCATCC GTGGTACAGG CATTGGAACC ATGGTGACTT CTCTGGTTCG      60

GGCCAGTCAC GCCACACCCC GCCGGAGAGC CCCCACCCCG GCCGCCCTAA TGCCACCATT     120

TCTAGAATCG AAGGTCGCGC TAGACCTTCG AG                                   152
```

(2) INFORMATION FOR SEQ ID NO: 78:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 78:

```
TCTCACTCCT CGAGATATAA GCACGATATC GGTTGCGATG CTGGGGTTGA CAAGAAGTCG      60

TCGTCTGTGC GTGGTGGTTG TGGTGCTCAT TNGTCGCCAC CCCGCGCCGG CCGTGGTCCT     120

CGCGGCACGA TGGTTAGCAG GCTTTCTAGA ATCGAAGGTC GCGCTAGACC TTCGAGA       177
```

(2) INFORMATION FOR SEQ ID NO: 79:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 79:

```
TCTCACTCCT CGAGTCAGGG CTCCAAGCAG TGTATGCAGT ACCGCACCGG TCGTTTGACG      60

GTGGGGTCTG AGTATGGTTG TGGTATGAAC CCCGCCCGCC ATGCCACGCC CGCTTATCCG     120

GCGCGCCTGC TGCCACGCTA TCGCTCTAGA ATCGAAGGTC GCGCTAGACC TTCGAGA       177
```

(2) INFORMATION FOR SEQ ID NO: 80:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 80:

```
TCTCACTCCT CGAGTGGGCG GACTACTAGT GAGATTTCTG GGCTCTGGGG TTGGGGTGAC      60

GACCGGAGCG GTTATGGTTG GGGTAACACG CTCCGCCCCA ACTACATCCC TTATAGGCAG     120

GCGACGAACA GGCATCGTTA TACGTCTAGA ATCGAAGGTC GCGCTAGACC TTCGAGA       177
```

(2) INFORMATION FOR SEQ ID NO: 81:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 81:

```
TCTCACTCCT CGAGGTGGAA TTGGACTGTC TTGCCCGCCA CTGGCGGCCA TTACTGGACG        60

CGTTCGACGG ACTATCACGC CATTAACAAT CACAGGCCGA GCATCCCCCA CCAGCATCCG       120

ACCCCTATCT CTAGAATCGA AGGTCGCGCT AGACCTTCGA GA                          162
```

(2) INFORMATION FOR SEQ ID NO: 82:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 82:

```
TCTCACTCCT CGAGTTGGTC GTCGTGGAAT TGGAGCTCTA AGACTACTCG TCTGGGCGAC        60

AGGGCGACTC GGGAGGGTTG TGGTCCCAGC CAGTCTGATG GCTGTCCTTA TAACGGCCGC       120

CTTACGACCG TCAAGCCTCG CACGTCTAGA ATCGAAGGTC GCGCTAGACC TTCGAGA          177
```

(2) INFORMATION FOR SEQ ID NO: 83:

(i) SEQUENCE CHARACTERISTICS:
        (A) LENGTH: 156 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 83:

```
TCTCACTCCT CGAGTGGTAG TTTGAACGCA TGGCAACCGC GGTCATGGGT GGGGGGCGCG        60

TTCCGGTCAC ACGCCAACAA TAACTTGAAC CCCAAGCCCA CCATGGTTAC TNGTCACCCT       120

ACCTCTAGAA TCGAAGGTCG CGCTAGACCT TCGAGA                                 156
```

(2) INFORMATION FOR SEQ ID NO: 84:

(i) SEQUENCE CHARACTERISTICS:
        (A) LENGTH: 178 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 84:

```
TCTCACTCCT CGAGGTATTC GGGTTTGTCC CCGCGGGACA ACGGTCCCGC TTGTAGTCAG        60

GAGGCTACCT TGGAGGGTTG TGGTGCGCAG AGGCTGATGT CCACCCGTCG CAAGGGCCGC       120

AACTCCCGCC CCGGGTGGAC GCTCTCTAGA ATCGAAGGTC GCGCTAGACC CTTCGAGA         178
```

(2) INFORMATION FOR SEQ ID NO: 85:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 85:

```
TCTCACTCCT CGAGCGTGGG GAATGATAAG ACTAGCAGGC CGGTTTCCTT CTACGGGCGC    60

GTTAGTGATC TGTGGAACGC CAGCTTGATG CCGAAGCGTA CTCCCAGCTC GAAGCGCCAC   120

GATGATGGCT CTAGAATCGA AGGTCGCGCT AGACCTTCGA GA                     162
```

(2) INFORMATION FOR SEQ ID NO: 86:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 86:

```
TCTCACTCCT CGAGTACTCC CCCCAGTAGG GAGGCGTATA GTAGGCCCTA TAGTGTCGAT    60

AGCGATTCGG ATACGAACGC CAAGCACAGC TCCCACAACC GCCGTNTGCG GACGCGCAGC   120

CGCCCGAACT CTAGAATCGA AGGTCGCGCT AGACCTTCGA GA                     162
```

(2) INFORMATION FOR SEQ ID NO: 87:

(i) SEQUENCE CHARACTERISTICS:
        (A) LENGTH: 159 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 87:

```
TCTCACTCCT CGAGATGGCC TAGTGTGGGT TACAAGGGTA ATGGCAGTGA CACTATTGAT    60

GTTCACAGCA ATGACGCCAG TACTAAGAGG TCCCTCATCT ATAACCACCG CCGCCCCNTC   120

TTTCCCTCTA GAATCGAAGG TCGCGCTAGA CCTTCGAGA                         159
```

(2) INFORMATION FOR SEQ ID NO: 88:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 88:

```
TCTCACTCCT CGAGAACGTT TGAGAACGAC GGGCTGGGCG TCGGCCGGTC TATTCAGAAG    60

AAGTCGGATA GGTGGTACGC CAGCCACAAC ATTCGTAGCC ATTTCGCGTC CATGTCTCCC   120

GCTGGTAAGT CTAGAATCGA AGGTCGCGCT AGACCTTCGA GA                     162
```

(2) INFORMATION FOR SEQ ID NO: 89:

(i) SEQUENCE CHARACTERISTICS:
        (A) LENGTH: 160 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 89:

```
TCTCACTCCT CGAGCTATTG TCGGGTTAAG GGTGGTGGGG AGGGGGGGCA TACGGATTCC      60

AATCTGGCTA GGTCGGGTTG TGGTAAGGTG GCCAGGACCA GCAGGCTTCA GCATATCAAC     120

CCGCGCGCTA CCCCCCCCTC CCGGTCTAGA ATCGAAGGTC                           160
```

(2) INFORMATION FOR SEQ ID NO: 90:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 90:

```
TCTCACTCCT CGAGTTGGAC TCGGTGGGGC AAGCACANTC ATGGGGGGTT TGTGAACAAG      60

TCTCCCCCTG GGAAGAACGC CACGAGCCCC TACACCGACG CCCAGCTGCC CAGTGATCAG     120

GGTCCTCCCT CTAGAATCGA AGGTCGCGCT AGACCTTCGA GA                        162
```

(2) INFORMATION FOR SEQ ID NO: 91:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 91:

```
TCTCACTCCT CGAGTCAGGT TGATTCGTTT CGTAATAGCT TTCGGTGGTA TGAGCCGAGC      60

AGGGCTCTGT GCCATGGTTG TGGTAAGCGC GACACCTCCA CCACTCGTAT CCACAATAGC     120

CCCAGCGACT CCTATCCTAC ACGCTCTAGA ATCGAAGGTC GCGCTAGACC TTCGAGA        177
```

(2) INFORMATION FOR SEQ ID NO: 92:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 92:

```
TCTCACTCCT CGAGCTTTTT GCGGTTCCAG AGTCCGAGGT TCGAGGATTA CAGTAGGACG      60

ATCTNTCGGT TGCGCAACGC CACGAACCCG AGTAATGTCT CCGATGCGCA CAATAACCGG     120

GCCTTGGCCT CTAGAATCGA AGGTCGCGCT AGACCTTCGA GA                        162
```

(2) INFORMATION FOR SEQ ID NO: 93:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 93:

```
TCTCACTCCT CGAGGAGCAT CACCGACGGG GGCATCAATG AGGTGGACCT GAGTAGTGTG      60

TCGAACGTTC TTGAGAACGC CAACTCGCAT AGGGCCTACA GGAAGCATCG CCCGACCTTG     120

AAGCGTCCTT CTAGAATCGA AGGTCGCGCT AGACCTTCGA GA                        162
```

(2) INFORMATION FOR SEQ ID NO: 94:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 94:

```
TCTCACTCCT CGAGTTCGAA GGTGAGCAGC CCGAGGGATC CGACGGTCCC GCGGAAGGGC      60

GGCAATGTTG ATTATGGTTG TGGTCACAGG TCTTCCGCCC GGATGCCTAC CTCCGCTCTG     120

TCGTCGATCA CGAAGTGCTA CACTTCTAGA ATCGAAGGTC GCGCTAGACC TTCGAGA        177
```

(2) INFORMATION FOR SEQ ID NO: 95:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 95:

```
TCTCACTCCT CGAGAGCCAG TANGCAGGGC GGCCGGGGTG TTGCCCCTGA GTTTGGGGCG      60

AGCGTTTTGG GTNGTGGTTG TGGTAGCGCC ACTTATTACA CGAACTCCAC CAGCTGCAAG     120

GATGCTATGG GCCACAACTA CTCGTCTAGA ATCGAAGGTC GCGNTAGACC TTCGAGA        177
```

(2) INFORMATION FOR SEQ ID NO: 96:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 96:

```
TCTCACTCCT CGAGATGGTG CGAGAAGCAC AAGTTTACGG CTGCGCGTTG CAGCGCGGGG      60

GCGGGTTTTG AGAGGGANGC CAGCCGTCCG CCCCAGCCTG CCCACCGGGA TAATACCAAC     120

CGTAATGCNT NTAGAATCGA AGGTCGCGCT AGACCTTCGA GA                        162
```

(2) INFORMATION FOR SEQ ID NO: 97:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 97:

```
TCTCACTCCT CGAGTTTTCA GGTGTACCCG GACCATGGTC TGGAGAGGCA TGCTTTGGAC        60

GGGACGGGTC CGCTTTACGC CATGCCCGGC CGCTGGATTA GGGCGCGTCC GCAGAACAGG       120

GACCGCCAGT CTAGAATCGA AGGTCGCGCT AGACCTTCGA GA                         162
```

(2) INFORMATION FOR SEQ ID NO: 98:

(i) SEQUENCE CHARACTERISTICS:
        (A) LENGTH: 159 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 98:

```
TCTCACTCCT CGAGCAGGTG TACGGACAAC GAGCAGTGCC CCGATACCGG GANTAGGTCT        60

CGTTCCGTTA GTAACGCCAG GTACTTTTCG AGCAGGTTGC TCAAGACTCA CGCCCCCCAT       120

CGCCCTTCTA GAATCGAAGG TCGCGCTAGA CCTTCGAGA                             159
```

(2) INFORMATION FOR SEQ ID NO: 99:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 99:

```
TCTCACTCCT CGAGTGCCAG GGATAGCGGG CCTGCGGAGG ATGGGTCCCG CGCCGTCCGG        60

TTGAACGGGG TTGAGAACGC CAACACTAGG AAGTCCTCCC GCAGTAACCC GCGGGGTAGG       120

CGCCATCCCT CTAGAATCGA AGGTCGCGCT AGACCTTCGA GA                         162
```

(2) INFORMATION FOR SEQ ID NO: 100:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 100:

```
TCTCACTCCT CGAGTTCCGC CGATGCGGAG AAGTGTGCGG GCAGTCTGTT GTGGTGGGGT        60

AGGCAGAACA ACTCCGGTTG TGGTTCGCCC ACGAAGAAGC ATCTGAAGCA CCGCAATCGC       120

AGTCAGACCT CCTCTTCGTC CCACTCTAGA ATCGAAGGTC GCGCTAGACC TTCGAGA         177
```

(2) INFORMATION FOR SEQ ID NO: 101:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 101:

```
TCTCACTCCT CGAGACCGAA GAACGTGGCC GATGCTTATT CGTCTCAGGA CGGGGCGGCG      60

GCCGAGGAGA CGTCTCACGC CAGTAATGCC GCGCGGAAGT CCCCTAAGCA CAAGCCCTTG     120

AGGCGGCCTT CTAGAATCGA AGGTCGCGCT AGACCTTCGA GA                       162
```

(2) INFORMATION FOR SEQ ID NO: 102:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 102:

```
TCTCACTCCT CGAGAGGCAG TACGGGGACG GCCGGCGGCG AGCGTTCCGG GGTGCTCAAC      60

CTGCACACCA GGGATAACGC CAGCGGCAGC GGTTTCAAAC CGTGGTACCC TTCGAATCGG     120

GGTCACAAGT CTAGAATCGA AGGTCGCGCT AGACCTTCGA GA                       162
```

(2) INFORMATION FOR SEQ ID NO: 103:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 103:

```
TCTCACTCCT CGAGGTGGGG GTGGGAGAGG AGTCCGTCCG ACTACGATTC TGATATGGAC      60

TTGGGGGCGA GGAGGTACGC CACCCGCACC CACCGCGCGC CCCCTCGCGT CTTGAAGGCT     120

CCCCTGCCCT CTAGAATCGA AGGTCGCGCT AGACCTTCGA GA                       162
```

(2) INFORMATION FOR SEQ ID NO: 104:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 104:

```
TCTCACTCCT CGAGGCACTG GAAGTGCGAG GGCTCTCAGG CTGCCTACGG GGACAAGGAT      60

ATCGGGAGGT CCAGGGGTTG TGGTTCCATT ACAAAGAATA ACACTAATCA CGCCCATCCT     120

AGCCACGGCG CCGTTGCTAA GATCTCTAGA ATCGAAGGTC GCGCTAGACC TTCGAGA       177
```

(2) INFORMATION FOR SEQ ID NO: 105:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 105:

```
TCTCACTCCT CGAGCCGCGA GGAGGCGAAC TGGGACGGCT ATAAGAGGGA GATGAGCCAC      60

CGGAGTCGCT TTTGGGACGC CACCCACCTG TCCCGCCCTC GCCGCCCCGC TAACTCTGGT     120

GACCCTAACT CTAGAATCGA AGGTCGCGCT AGACCTTCGA GA                        162
```

(2) INFORMATION FOR SEQ ID NO: 106:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 106:

```
TCTCACTCNT CGAGAGAGTT CGCGGAGAGG AGGTTGTGGG GGTGTGATGA CCTGAGTTGG      60

CGTCTCGACG CGGAGGGTTG TGGTCCCACT CCGAGCAATC GGGCCGTCAA GCATCGCAAG     120

CCCCGCCCAC GCTCCCCCGC ACTCTCTAGA ATCGAAGGTC GCGCTAGACC TTCGAGA        177
```

(2) INFORMATION FOR SEQ ID NO: 107:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 107:

```
TCTCACTCNT NGAGTGATCA CGCGTTGGGG ACGAATCTGA GGTCTGACAA TGCCAAGGAG      60

CCGGGTGATT ACAACTGTTG TGGTAACGGG AACTCTACCG GGCGAAAGGT TTTTAACCGT     120

AGGCGCCCCT CCGCCATCCC CANTTCTAGA ATCGAAGGTC GCGCTAGACC TTCGAGA        177
```

(2) INFORMATION FOR SEQ ID NO: 108:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 108:

```
TCTCACTCCT CGAGGCATAT TTCTGAGTAT AGCTTTGCGA ATTCCCACTT GATGGGTGGC      60

GAGTCCAAGC GGAAGGGTTG TGGTATTAAC GGCTCCTTTT CTCCCACTTG TCCCCGCTCC     120

CCCACCCCAG CCTTCCGCCG CACCTCTAGA ATCGAAGGTC GCGCTAGACC TTCGAGA        177
```

(2) INFORMATION FOR SEQ ID NO: 109:

(i) SEQUENCE CHARACTERISTICS:
        (A) LENGTH: 158 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 109:

```
TCTCACTCCT CGAGCCGGGA GAGCGGGATG TGGGGTAGTT GGTGGCGTGG TCACAGGTTG      60

AATTCCACGG GGGGTAACGC CAACATGAAT GCTAGTCTGC CCCCCGACCC CCCTGTTTCC     120

ACTCCGTCTA GAATCGAAGG TCGCGCTAGA CCTTCGAG                             158
```

(2) INFORMATION FOR SEQ ID NO: 110:

(i) SEQUENCE CHARACTERISTICS:
        (A) LENGTH: 708 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 110:

```
Met Gly Met Ser Lys Ser His Ser Phe Phe Gly Tyr Pro Leu Ser Ile
 1               5                  10                  15

Phe Phe Ile Val Val Asn Glu Phe Cys Glu Arg Phe Ser Tyr Tyr Gly
            20                  25                  30

Met Arg Ala Ile Leu Ile Leu Tyr Phe Thr Asn Phe Ile Ser Trp Asp
        35                  40                  45

Asp Asn Leu Ser Thr Ala Ile Tyr His Thr Phe Val Ala Leu Cys Tyr
    50                  55                  60

Leu Thr Pro Ile Leu Gly Ala Leu Ile Ala Asp Ser Trp Leu Gly Lys
65                  70                  75                  80

Phe Lys Thr Ile Val Ser Leu Ser Ile Val Tyr Thr Ile Gly Gln Ala
                85                  90                  95

Val Thr Ser Val Ser Ser Ile Asn Asp Leu Thr Asp His Asn His Asp
            100                 105                 110

Gly Thr Pro Asp Ser Leu Pro Val His Val Val Leu Ser Leu Ile Gly
        115                 120                 125

Leu Ala Leu Ile Ala Leu Gly Thr Gly Gly Ile Lys Pro Cys Val Ser
    130                 135                 140

Ala Phe Gly Gly Asp Gln Phe Glu Glu Gly Gln Glu Lys Gln Arg Asn
145                 150                 155                 160

Arg Phe Phe Ser Ile Phe Tyr Leu Ala Ile Asn Ala Gly Ser Leu Leu
                165                 170                 175

Ser Thr Ile Ile Thr Pro Met Leu Arg Val Gln Gln Cys Gly Ile His
            180                 185                 190

Ser Lys Gln Ala Cys Tyr Pro Leu Ala Phe Gly Val Pro Ala Ala Leu
        195                 200                 205

Met Ala Val Ala Leu Ile Val Phe Val Leu Gly Ser Gly Met Tyr Lys
    210                 215                 220

Lys Phe Lys Pro Gln Gly Asn Ile Met Gly Lys Val Ala Lys Cys Ile
225                 230                 235                 240

Gly Phe Ala Ile Lys Asn Arg Phe Arg His Arg Ser Lys Ala Phe Pro
                245                 250                 255
```

-continued

```
Lys Arg Glu His Trp Leu Asp Trp Ala Lys Glu Lys Tyr Asp Glu Arg
            260                 265                 270
Leu Ile Ser Gln Ile Lys Met Val Thr Arg Val Met Phe Leu Tyr Ile
            275                 280                 285
Pro Leu Pro Met Phe Trp Ala Leu Phe Asp Gln Gly Ser Arg Trp
            290                 295                 300
Thr Leu Gln Ala Thr Thr Met Ser Gly Lys Ile Gly Ala Leu Glu Ile
305                 310                 315                 320
Gln Pro Asp Gln Met Gln Thr Val Asn Ala Ile Leu Ile Val Ile Met
                325                 330                 335
Val Pro Ile Phe Asp Ala Val Leu Tyr Pro Leu Ile Ala Lys Cys Gly
            340                 345                 350
Phe Asn Phe Thr Ser Leu Lys Lys Met Ala Val Gly Met Val Leu Ala
            355                 360                 365
Ser Met Ala Phe Val Val Ala Ala Ile Val Gln Val Glu Ile Asp Lys
    370                 375                 380
Thr Leu Pro Val Phe Pro Lys Gly Asn Glu Val Gln Ile Lys Val Leu
385                 390                 395                 400
Asn Ile Gly Asn Asn Thr Met Asn Ile Ser Leu Pro Gly Glu Met Val
                405                 410                 415
Thr Leu Gly Pro Met Ser Gln Thr Asn Ala Phe Met Thr Phe Asp Val
            420                 425                 430
Asn Lys Leu Thr Arg Ile Asn Ile Ser Ser Pro Gly Ser Pro Val Thr
            435                 440                 445
Ala Val Thr Asp Asp Phe Lys Gln Gly Gln Arg His Thr Leu Leu Val
    450                 455                 460
Trp Ala Pro Asn His Tyr Gln Val Val Lys Asp Gly Leu Asn Gln Lys
465                 470                 475                 480
Pro Glu Lys Gly Glu Asn Gly Ile Arg Phe Val Asn Thr Phe Asn Glu
                485                 490                 495
Leu Ile Thr Ile Thr Met Ser Gly Lys Val Tyr Ala Asn Ile Ser Ser
            500                 505                 510
Tyr Asn Ala Ser Thr Tyr Gln Phe Phe Pro Ser Gly Ile Lys Gly Phe
    515                 520                 525
Thr Ile Ser Ser Thr Glu Ile Pro Pro Gln Cys Gln Pro Asn Phe Asn
    530                 535                 540
Thr Phe Tyr Leu Glu Phe Gly Ser Ala Tyr Thr Tyr Ile Val Gln Arg
545                 550                 555                 560
Lys Asn Asp Ser Cys Pro Glu Val Lys Val Phe Glu Asp Ile Ser Ala
                565                 570                 575
Asn Thr Val Asn Met Ala Leu Gln Ile Pro Gln Tyr Phe Leu Leu Thr
            580                 585                 590
Cys Gly Glu Val Val Phe Ser Val Thr Gly Leu Glu Phe Ser Tyr Ser
            595                 600                 605
Gln Ala Pro Ser Asn Met Lys Ser Val Leu Gln Ala Gly Trp Leu Leu
    610                 615                 620
Thr Val Ala Val Gly Asn Ile Ile Val Leu Ile Val Ala Gly Ala Gly
625                 630                 635                 640
Gln Phe Ser Lys Gln Trp Ala Glu Tyr Ile Leu Phe Ala Ala Leu Leu
                645                 650                 655
Leu Val Val Cys Val Val Phe Ala Ile Met Ala Arg Phe Tyr Thr Tyr
            660                 665                 670
```

```
Ile Asn Pro Ala Glu Ile Glu Ala Gln Phe Asp Glu Asp Glu Lys Lys
        675                 680                 685

Asn Arg Leu Glu Lys Ser Asn Pro Tyr Phe Met Ser Gly Ala Asn Ser
        690                 695                 700

Gln Lys Gln Met
705
```

(2) INFORMATION FOR SEQ ID NO: 111:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 111:

TCCGGACTCT CATAAGCGCC GG                                  22

(2) INFORMATION FOR SEQ ID NO: 112:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 112:

ACAACGGGCC AGAAAGAGCG AG                                  22

(2) INFORMATION FOR SEQ ID NO: 113:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 113:

ACACCACCCC AATCGGAGCT AC                                  22

(2) INFORMATION FOR SEQ ID NO: 114:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 114:

TCAGAATCCG TGCACTGGCC AA                                  22

(2) INFORMATION FOR SEQ ID NO: 115:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 115:

GCCCTATTCA TACCACCGGA GT                                                    22

(2) INFORMATION FOR SEQ ID NO: 116:

(i) SEQUENCE CHARACTERISTICS:
                (A) LENGTH: 22 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO: 116:

CATCAGTCCT ACCGCCGAAA AG                                                    22

(2) INFORMATION FOR SEQ ID NO: 117:

(i) SEQUENCE CHARACTERISTICS:
                (A) LENGTH: 22 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO: 117:

CGTATAGCTA TTGTGAGCGA TG                                                    22

(2) INFORMATION FOR SEQ ID NO: 118:

(i) SEQUENCE CHARACTERISTICS:
                (A) LENGTH: 22 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO: 118:

ACGCGCGGAA CGAGCAGTAC CA                                                    22

(2) INFORMATION FOR SEQ ID NO: 119:

(i) SEQUENCE CHARACTERISTICS:
                (A) LENGTH: 22 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO: 119:

CCATAATGAT CCCCGTCACT AT                                                    22

(2) INFORMATION FOR SEQ ID NO: 120:

(i) SEQUENCE CHARACTERISTICS:
                (A) LENGTH: 22 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO: 120:

AGACACCCCT TAGCCGTCGT AG                                                    22

(2) INFORMATION FOR SEQ ID NO: 121:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 121:

AGCTCCGTGA CCTTAGTCAT AA                                                    22

(2) INFORMATION FOR SEQ ID NO: 122:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 122:

TGCACAGCTC AGCGCCGCAC CA                                                    22

(2) INFORMATION FOR SEQ ID NO: 123:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 123:

ACGGGTCATC AGCGCCGCAC CA                                                    22

(2) INFORMATION FOR SEQ ID NO: 124:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 124:

TGTCACCCCC CTCCCCGGAC TT                                                    22

(2) INFORMATION FOR SEQ ID NO: 125:

(i) SEQUENCE CHARACTERISTICS:
            (A) LENGTH: 22 base pairs
            (B) TYPE: nucleic acid
            (C) STRANDEDNESS: single
            (D) TOPOLOGY: linear

```
         (ii) MOLECULE TYPE: DNA (xi) SEQUENCE DESCRIPTION: SEQ ID NO: 125:

ACTCGCAATT ATTGGCGCTC GA                                             22

(2) INFORMATION FOR SEQ ID NO: 126:

(i) SEQUENCE CHARACTERISTICS:
              (A) LENGTH: 22 base pairs
              (B) TYPE: nucleic acid
              (C) STRANDEDNESS: single
              (D) TOPOLOGY: linear (ii) MOLECULE TYPE: DNA (xi) SEQUENCE DESCRIPTION: SEQ ID NO: 126:

GTCTTCTCAA CCTTATCCTG CG                                             22

(2) INFORMATION FOR SEQ ID NO: 127:

(i) SEQUENCE CHARACTERISTICS:
              (A) LENGTH: 22 base pairs
              (B) TYPE: nucleic acid
              (C) STRANDEDNESS: single
              (D) TOPOLOGY: linear (ii) MOLECULE TYPE: DNA (xi) SEQUENCE DESCRIPTION: SEQ ID NO: 127:

AAAGCCCCCT GCTAAACTCC CA                                             22

(2) INFORMATION FOR SEQ ID NO: 128:

(i) SEQUENCE CHARACTERISTICS:
              (A) LENGTH: 22 base pairs
              (B) TYPE: nucleic acid
              (C) STRANDEDNESS: single
              (D) TOPOLOGY: linear (ii) MOLECULE TYPE: DNA (xi) SEQUENCE DESCRIPTION: SEQ ID NO: 128:

CTGCGTCTGC CACGTCGTCA TC                                             22

(2) INFORMATION FOR SEQ ID NO: 129:

(i) SEQUENCE CHARACTERISTICS:
              (A) LENGTH: 22 base pairs
              (B) TYPE: nucleic acid
              (C) STRANDEDNESS: single
              (D) TOPOLOGY: linear (ii) MOLECULE TYPE: DNA (xi) SEQUENCE DESCRIPTION: SEQ ID NO: 129:

GTTAAAAGAG GGCAAGCTCG GA                                             22

(2) INFORMATION FOR SEQ ID NO: 130:

(i) SEQUENCE CHARACTERISTICS:
              (A) LENGTH: 22 base pairs
              (B) TYPE: nucleic acid
              (C) STRANDEDNESS: single
              (D) TOPOLOGY: linear
```

(ii) MOLECULE TYPE: DNA (xi) SEQUENCE DESCRIPTION: SEQ ID NO: 130:

CCGAGTTCTT GATGTCCTCC AT                                              22

(2) INFORMATION FOR SEQ ID NO: 131:

(i) SEQUENCE CHARACTERISTICS:
          (A) LENGTH: 22 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO: 131:

TCCAATGCCT GTACCACGGA TG                                              22

(2) INFORMATION FOR SEQ ID NO: 132:

(i) SEQUENCE CHARACTERISTICS:
          (A) LENGTH: 22 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO: 132:

TCGCAACCGA TATCGTGCTT AT                                              22

(2) INFORMATION FOR SEQ ID NO: 133:

(i) SEQUENCE CHARACTERISTICS:
          (A) LENGTH: 22 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO: 133:

TGCATACACT GCTTGGAGCC CT                                              22

(2) INFORMATION FOR SEQ ID NO: 134:

(i) SEQUENCE CHARACTERISTICS:
          (A) LENGTH: 22 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO: 134:

GAAATCTCAC TAGTAGTCCG CC                                              22

(2) INFORMATION FOR SEQ ID NO: 135:

(i) SEQUENCE CHARACTERISTICS:
          (A) LENGTH: 22 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO: 135:

GCGGGCAAGA CAGTCCAATT CC                                            22

(2) INFORMATION FOR SEQ ID NO: 136:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 136:

GAGCTCCAAT TCCACGACGA CC                                            22

(2) INFORMATION FOR SEQ ID NO: 137:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 137:

GGTTGCCATG CGTTCAAACT AC                                            22

(2) INFORMATION FOR SEQ ID NO: 138:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 138:

TCCCGCGGGG ACAAACCCGA AT                                            22

(2) INFORMATION FOR SEQ ID NO: 139:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 139:

CTGCTAGTCT TATCATTCCC CA                                            22

(2) INFORMATION FOR SEQ ID NO: 140:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 140:

CTATCGACAC TATAGGGCCT AC                                                    22

(2) INFORMATION FOR SEQ ID NO: 141:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 141:

TACCCTTGTA ACCCACACTA GG                                                    22

(2) INFORMATION FOR SEQ ID NO: 142:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 142:

TTCTTCTGAA TAGACCGGCC GA                                                    22

(2) INFORMATION FOR SEQ ID NO: 143:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 143:

CCACCACCCT TAACCCGACA AT                                                    22

(2) INFORMATION FOR SEQ ID NO: 144:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 144:

AGGGGGAGAC TTGTTCACAA AC                                                    22

(2) INFORMATION FOR SEQ ID NO: 145:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 145:

CGGCTCATAC CACCGAAAGC TA                                            22

(2) INFORMATION FOR SEQ ID NO: 146:

(i) SEQUENCE CHARACTERISTICS:
             (A) LENGTH: 22 base pairs
             (B) TYPE: nucleic acid
             (C) STRANDEDNESS: single
             (D) TOPOLOGY: linear (ii) MOLECULE TYPE: DNA (xi) SEQUENCE DESCRIPTION: SEQ ID NO: 146:

ATCGTCCTAC TGTAATCCTC GA                                            22

(2) INFORMATION FOR SEQ ID NO: 147:

(i) SEQUENCE CHARACTERISTICS:
             (A) LENGTH: 22 base pairs
             (B) TYPE: nucleic acid
             (C) STRANDEDNESS: single
             (D) TOPOLOGY: linear (ii) MOLECULE TYPE: DNA (xi) SEQUENCE DESCRIPTION: SEQ ID NO: 147:

GACACACTAC TCAGGTCCAC CT                                            22

(2) INFORMATION FOR SEQ ID NO: 148:

(i) SEQUENCE CHARACTERISTICS:
             (A) LENGTH: 22 base pairs
             (B) TYPE: nucleic acid
             (C) STRANDEDNESS: single
             (D) TOPOLOGY: linear (ii) MOLECULE TYPE: DNA (xi) SEQUENCE DESCRIPTION: SEQ ID NO: 148:

CCATAATCAA CATTGCCGCC CT                                            22

(2) INFORMATION FOR SEQ ID NO: 149:

(i) SEQUENCE CHARACTERISTICS:
             (A) LENGTH: 22 base pairs
             (B) TYPE: nucleic acid
             (C) STRANDEDNESS: single
             (D) TOPOLOGY: linear (ii) MOLECULE TYPE: DNA (xi) SEQUENCE DESCRIPTION: SEQ ID NO: 149:

CAAAACGCTC GCCCCAAACT CA                                            22

(2) INFORMATION FOR SEQ ID NO: 150:

(i) SEQUENCE CHARACTERISTICS:
             (A) LENGTH: 22 base pairs
             (B) TYPE: nucleic acid
             (C) STRANDEDNESS: single
             (D) TOPOLOGY: linear -continued (ii) MOLECULE TYPE: DNA (xi) SEQUENCE DESCRIPTION: SEQ ID NO: 150:

GTAAACTTGT GCTTCTCGCA CC					22

(2) INFORMATION FOR SEQ ID NO: 151:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 151:

CCATGGTCCG GGTACACCTG AA					22

(2) INFORMATION FOR SEQ ID NO: 152:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 152:

GTTACTAACG GAACGAGACC TA					22

(2) INFORMATION FOR SEQ ID NO: 153:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 153:

TGTTGGCGTT CTCAACCCCG TT					22

(2) INFORMATION FOR SEQ ID NO: 154:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 154:

ACAACCGGAG TTGTTCTGCC TA					22

(2) INFORMATION FOR SEQ ID NO: 155:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 155:

TAAGCATCGG CCACGTTCTT CG                                                    22

(2) INFORMATION FOR SEQ ID NO: 156:

(i) SEQUENCE CHARACTERISTICS:
          (A) LENGTH: 22 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO: 156:

TTATCCCTGG TGTGCAGGTT GA                                                    22

(2) INFORMATION FOR SEQ ID NO: 157:

(i) SEQUENCE CHARACTERISTICS:
          (A) LENGTH: 22 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO: 157:

TATCAGAATC GTAGTCGGAC GG                                                    22

(2) INFORMATION FOR SEQ ID NO: 158:

(i) SEQUENCE CHARACTERISTICS:
          (A) LENGTH: 22 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO: 158:

CTTTGTAATG GAACCACAAC CC                                                    22

(2) INFORMATION FOR SEQ ID NO: 159:

(i) SEQUENCE CHARACTERISTICS:
          (A) LENGTH: 22 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO: 159:

CGGTGGCTCA TCTCCCTCTT AT                                                    22

(2) INFORMATION FOR SEQ ID NO: 160:

(i) SEQUENCE CHARACTERISTICS:
          (A) LENGTH: 22 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO: 160:

ATCAGACTGG CTGGGACCAC AA                                                22

(2) INFORMATION FOR SEQ ID NO: 161:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 161:

CACAACCTCC TCTCCGCGAA CT                                                22

(2) INFORMATION FOR SEQ ID NO: 162:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 162:

AGATTCGTCC CCAACGCGTG AT                                                22

(2) INFORMATION FOR SEQ ID NO: 163:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 163:

GGGAATTCGC AAAGCTATAC TC                                                22

(2) INFORMATION FOR SEQ ID NO: 164:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 164:

CCCCGTGGAA TTCAACCTGT GA                                                22

(2) INFORMATION FOR SEQ ID NO: 165:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 165:

GTCGTCTTTC CAGACGT                                                                                17

(2) INFORMATION FOR SEQ ID NO: 166:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 166:

CTTGCATGCC TGCAGGTCGA C                                                                            21

(2) INFORMATION FOR SEQ ID NO: 167:

(i) SEQUENCE CHARACTERISTICS:
        (A) LENGTH: 37 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 167:

Arg Ile Ala Gly Leu Pro Trp Tyr Arg Cys Arg Thr Val Ala Phe Glu
 1               5                  10                  15

Thr Gly Met Gln Asn Thr Gln Leu Cys Ser Thr Ile Val Gln Leu Ser
            20                  25                  30

Phe Thr Pro Glu Glu
        35

(2) INFORMATION FOR SEQ ID NO: 168:

(i) SEQUENCE CHARACTERISTICS:
        (A) LENGTH: 44 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 168:

Arg Glu Phe Ala Glu Arg Arg Leu Trp Gly Cys Asp Asp Leu Ser Trp
 1               5                  10                  15

Arg Leu Asp Ala Glu Gly Cys Gly Pro Thr Pro Ser Asn Arg Ala Val
            20                  25                  30

Lys His Arg Lys Pro Arg Pro Arg Ser Pro Ala Leu
        35                  40

(2) INFORMATION FOR SEQ ID NO: 169:

(i) SEQUENCE CHARACTERISTICS:
        (A) LENGTH: 41 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 169:

Ser Gly Ser His Ser Gly Gly Met Asn Arg Ala Tyr Gly Asp Val Phe
1               5                   10                  15

Arg Glu Leu Arg Asp Arg Trp Tyr Ala Thr Ser His His Thr Arg Pro
            20                  25                  30

Thr Pro Gln Leu Pro Arg Gly Pro Asn
        35                  40

(2) INFORMATION FOR SEQ ID NO: 170:

(i) SEQUENCE CHARACTERISTICS:
        (A) LENGTH: 20 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 170:

Ser Thr Pro Pro Ser Arg Glu Ala Tyr Ser Arg Pro Tyr Ser Val Asp
1               5                   10                  15

Ser Asp Ser Asp
            20

(2) INFORMATION FOR SEQ ID NO: 171:

(i) SEQUENCE CHARACTERISTICS:
        (A) LENGTH: 29 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 171:

Ser Thr Pro Pro Ser Arg Glu Ala Tyr Ser Arg Pro Tyr Ser Val Asp
1               5                   10                  15

Ser Asp Ser Asp Thr Asn Ala Lys His Ser Ser His Asn
            20                  25

(2) INFORMATION FOR SEQ ID NO: 172:

(i) SEQUENCE CHARACTERISTICS:
        (A) LENGTH: 19 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 172:

Thr Asn Ala Lys His Ser Ser His Asn Arg Arg Leu Arg Thr Arg Ser
1               5                   10                  15

Arg Pro Asn (2) INFORMATION FOR SEQ ID NO: 173:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 173:

Thr Asn Ala Lys His Ser Ser His Asn
1               5

(2) INFORMATION FOR SEQ ID NO: 174:

(i) SEQUENCE CHARACTERISTICS:
              (A) LENGTH: 14 amino acids
              (B) TYPE: amino acid
              (C) STRANDEDNESS: <Unknown>
              (D) TOPOLOGY: unknown (ii) MOLECULE TYPE: peptide (xi) SEQUENCE DESCRIPTION: SEQ ID NO: 174:

Ser Ser His Asn Arg Arg Leu Arg Thr Arg Ser Arg Pro Asn
1               5                   10

(2) INFORMATION FOR SEQ ID NO: 175:

(i) SEQUENCE CHARACTERISTICS:
              (A) LENGTH: 10 amino acids
              (B) TYPE: amino acid
              (C) STRANDEDNESS: <Unknown>
              (D) TOPOLOGY: unknown (ii) MOLECULE TYPE: peptide (xi) SEQUENCE DESCRIPTION: SEQ ID NO: 175:

Arg Arg Leu Arg Thr Arg Ser Arg Pro Asn
1               5                   10

(2) INFORMATION FOR SEQ ID NO: 176:

(i) SEQUENCE CHARACTERISTICS:
              (A) LENGTH: 708 amino acids
              (B) TYPE: amino acid
              (C) STRANDEDNESS: <Unknown>
              (D) TOPOLOGY: unknown (ii) MOLECULE TYPE: peptide (xi) SEQUENCE DESCRIPTION: SEQ ID NO: 176:

Met Gly Met Ser Lys Ser His Ser Phe Phe Gly Tyr Pro Leu Ser Ile
1               5                   10                  15

Phe Phe Ile Val Val Asn Glu Phe Cys Glu Arg Phe Ser Tyr Tyr Gly
                20                  25                  30

Met Arg Ala Ile Leu Ile Leu Tyr Phe Thr Asn Phe Ile Ser Trp Asp
            35                  40                  45

Asp Asn Leu Ser Thr Ala Ile Tyr His Thr Phe Val Ala Leu Cys Tyr
        50                  55                  60

Leu Thr Pro Ile Leu Gly Ala Leu Ile Ala Asp Ser Trp Leu Gly Lys
65                  70                  75                  80

Phe Lys Thr Ile Val Ser Leu Ser Ile Val Tyr Thr Ile Gly Gln Ala
                85                  90                  95

Val Thr Ser Val Ser Ser Ile Asn Asp Leu Thr Asp His Asn His Asp
                100                 105                 110

Gly Thr Pro Asp Ser Leu Pro Val His Val Val Leu Ser Leu Ile Gly
            115                 120                 125

Leu Ala Leu Ile Ala Leu Gly Thr Gly Gly Ile Lys Pro Cys Val Ser
        130                 135                 140

-continued

```
Ala Phe Gly Gly Asp Gln Phe Glu Gly Gln Glu Lys Gln Arg Asn
145                 150                 155                 160

Arg Phe Phe Ser Ile Phe Tyr Leu Ala Ile Asn Ala Gly Ser Leu Leu
                165                 170                 175

Ser Thr Ile Ile Thr Pro Met Leu Arg Val Gln Gln Cys Gly Ile His
                180                 185                 190

Ser Lys Gln Ala Cys Tyr Pro Leu Ala Phe Gly Val Pro Ala Ala Leu
                195                 200                 205

Met Ala Val Ala Leu Ile Val Phe Val Leu Gly Ser Gly Met Tyr Lys
210                 215                 220

Lys Phe Lys Pro Gln Gly Asn Ile Met Gly Lys Val Ala Lys Cys Ile
225                 230                 235                 240

Gly Phe Ala Ile Lys Asn Arg Phe Arg His Arg Ser Lys Ala Phe Pro
                245                 250                 255

Lys Arg Glu His Trp Leu Asp Trp Ala Lys Glu Lys Tyr Asp Glu Arg
                260                 265                 270

Leu Ile Ser Gln Ile Lys Met Val Thr Arg Val Met Phe Leu Tyr Ile
                275                 280                 285

Pro Leu Pro Met Phe Trp Ala Leu Phe Asp Gln Gln Gly Ser Arg Trp
290                 295                 300

Thr Leu Gln Ala Thr Thr Met Ser Gly Lys Ile Gly Ala Leu Glu Ile
305                 310                 315                 320

Gln Pro Asp Gln Met Gln Thr Val Asn Ala Ile Leu Ile Val Ile Met
                325                 330                 335

Val Pro Ile Phe Asp Ala Val Leu Tyr Pro Leu Ile Ala Lys Cys Gly
                340                 345                 350

Phe Asn Phe Thr Ser Leu Lys Lys Met Ala Val Gly Met Val Leu Ala
                355                 360                 365

Ser Met Ala Phe Val Val Ala Ala Ile Val Gln Val Glu Ile Asp Lys
370                 375                 380

Thr Leu Pro Val Phe Pro Lys Gly Asn Glu Val Gln Ile Lys Val Leu
385                 390                 395                 400

Asn Ile Gly Asn Asn Thr Met Asn Ile Ser Leu Pro Gly Glu Met Val
                405                 410                 415

Thr Leu Gly Pro Met Ser Gln Thr Asn Ala Phe Met Thr Phe Asp Val
                420                 425                 430

Asn Lys Leu Thr Arg Ile Asn Ile Ser Ser Pro Gly Ser Pro Val Thr
                435                 440                 445

Ala Val Thr Asp Asp Phe Lys Gln Gly Gln Arg His Thr Leu Leu Val
450                 455                 460

Trp Ala Pro Asn His Tyr Gln Val Val Lys Asp Gly Leu Asn Gln Lys
465                 470                 475                 480

Pro Glu Lys Gly Glu Asn Gly Ile Arg Phe Val Asn Thr Phe Asn Glu
                485                 490                 495

Leu Ile Thr Ile Thr Met Ser Gly Lys Val Tyr Ala Asn Ile Ser Ser
                500                 505                 510

Tyr Asn Ala Ser Thr Tyr Gln Phe Phe Pro Ser Gly Ile Lys Gly Phe
                515                 520                 525

Thr Ile Ser Ser Thr Glu Ile Pro Pro Gln Cys Gln Pro Asn Phe Asn
                530                 535                 540

Thr Phe Tyr Leu Glu Phe Gly Ser Ala Tyr Thr Tyr Ile Val Gln Arg
545                 550                 555                 560
```

```
          Lys Asn Asp Ser Cys Pro Glu Val Lys Val Phe Glu Asp Ile Ser Ala
                      565                 570                 575

Asn Thr Val Asn Met Ala Leu Gln Ile Pro Gln Tyr Phe Leu Leu Thr
                      580                 585                 590

Cys Gly Glu Val Val Phe Ser Val Thr Gly Leu Glu Phe Ser Tyr Ser
                      595                 600                 605

Gln Ala Pro Ser Asn Met Lys Ser Val Leu Gln Ala Gly Trp Leu Leu
                      610                 615                 620

Thr Val Ala Val Gly Asn Ile Ile Val Leu Ile Val Ala Gly Ala Gly
          625                 630                 635                 640

Gln Phe Ser Lys Gln Trp Ala Glu Tyr Ile Leu Phe Ala Ala Leu Leu
                      645                 650                 655

Leu Val Val Cys Val Val Phe Ala Ile Met Ala Arg Phe Tyr Thr Tyr
                      660                 665                 670

Ile Asn Pro Ala Glu Ile Glu Ala Gln Phe Asp Glu Asp Glu Lys Lys
                      675                 680                 685

Asn Arg Leu Glu Lys Ser Asn Pro Tyr Phe Met Ser Gly Ala Asn Ser
                      690                 695                 700

Gln Lys Gln Met
          705

(2) INFORMATION FOR SEQ ID NO: 177:

(i) SEQUENCE CHARACTERISTICS:
        (A) LENGTH: 3345 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: Coding Sequence
        (B) LOCATION: 88...2583
        (D) OTHER INFORMATION:

(xi) SEQUENCE DESCRIPTION: SEQ ID NO: 177:

GAATTCCGTC TCGACCACTG AATGGAAGAA AAGGACTTTT AACCACCATT TTGTGACTTA          60

CAGAAAGGAA TTTGAATAAA GAAAACT ATG ATA CTT CAG GCC CAT CTT CAC TCC         114
                              Met Ile Leu Gln Ala His Leu His Ser
                               1               5

CTG TGT CTT CTT ATG CTT TAT TTG GCA ACT GGA TAT GGC CAA GAG GGG           162
Leu Cys Leu Leu Met Leu Tyr Leu Ala Thr Gly Tyr Gly Gln Glu Gly
 10              15                  20                  25

AAG TTT AGT GGA CCC CTG AAA CCC ATG ACA TTT TCT ATT TAT GAA GGC           210
Lys Phe Ser Gly Pro Leu Lys Pro Met Thr Phe Ser Ile Tyr Glu Gly
                 30                  35                  40

CAA GAA CCG AGT CAA ATT ATA TTC CAG TTT AAG GCC AAT CCT CCT GCT           258
Gln Glu Pro Ser Gln Ile Ile Phe Gln Phe Lys Ala Asn Pro Pro Ala
             45                  50                  55

GTG ACT TTT GAA CTA ACT GGG GAG ACA GAC AAC ATA TTT GTG ATA GAA           306
Val Thr Phe Glu Leu Thr Gly Glu Thr Asp Asn Ile Phe Val Ile Glu
             60                  65                  70

CGG GAG GGA CTT CTG TAT TAC AAC AGA GCC TTG GAC AGG GAA ACA AGA           354
Arg Glu Gly Leu Leu Tyr Tyr Asn Arg Ala Leu Asp Arg Glu Thr Arg
 75                  80                  85

TCT ACT CAC AAT CTC CAG GTT GCA GCC CTG GAC GCT AAT GGA ATT ATA           402
Ser Thr His Asn Leu Gln Val Ala Ala Leu Asp Ala Asn Gly Ile Ile
 90                  95                 100                 105
```

-continued

```
GTG GAG GGT CCA GTC CCT ATC ACC ATA GAA GTG AAG GAC ATC AAC GAC       450
Val Glu Gly Pro Val Pro Ile Thr Ile Glu Val Lys Asp Ile Asn Asp
            110                 115                 120

AAT CGA CCC ACG TTT CTC CAG TCA AAG TAC GAA GGC TCA GTA AGG CAG       498
Asn Arg Pro Thr Phe Leu Gln Ser Lys Tyr Glu Gly Ser Val Arg Gln
            125                 130                 135

AAC TCT CGC CCA GGA AAG CCC TTC TTG TAT GTC AAT GCC ACA GAC CTG       546
Asn Ser Arg Pro Gly Lys Pro Phe Leu Tyr Val Asn Ala Thr Asp Leu
            140                 145                 150

GAT GAT CCG GCC ACT CCC AAT GGC CAG CTT TAT TAC CAG ATT GTC ATC       594
Asp Asp Pro Ala Thr Pro Asn Gly Gln Leu Tyr Tyr Gln Ile Val Ile
            155                 160                 165

CAG CTT CCC ATG ATC AAC AAT GTC ATG TAC TTT CAG ATC AAC AAC AAA       642
Gln Leu Pro Met Ile Asn Asn Val Met Tyr Phe Gln Ile Asn Asn Lys
170                 175                 180                 185

ACG GGA GCC ATC TCT CTT ACC CGA GAG GGA TCT CAG GAA TTG AAT CCT       690
Thr Gly Ala Ile Ser Leu Thr Arg Glu Gly Ser Gln Glu Leu Asn Pro
                190                 195                 200

GCT AAG AAT CCT TCC TAT AAT CTG GTG ATC TCA GTG AAG GAC ATG GGA       738
Ala Lys Asn Pro Ser Tyr Asn Leu Val Ile Ser Val Lys Asp Met Gly
                205                 210                 215

GGC CAG AGT GAG AAT TCC TTC AGT GAT ACC ACA TCT GTG GAT ATC ATA       786
Gly Gln Ser Glu Asn Ser Phe Ser Asp Thr Thr Ser Val Asp Ile Ile
            220                 225                 230

GTG ACA GAG AAT ATT TGG AAA GCA CCA AAA CCT GTG GAG ATG GTG GAA       834
Val Thr Glu Asn Ile Trp Lys Ala Pro Lys Pro Val Glu Met Val Glu
            235                 240                 245

AAC TCA ACT GAT CCT CAC CCC ATC AAA ATC ACT CAG GTG CGG TGG AAT       882
Asn Ser Thr Asp Pro His Pro Ile Lys Ile Thr Gln Val Arg Trp Asn
250                 255                 260                 265

GAT CCC GGT GCA CAA TAT TCC TTA GTT GAC AAA GAG AAG CTG CCA AGA       930
Asp Pro Gly Ala Gln Tyr Ser Leu Val Asp Lys Glu Lys Leu Pro Arg
                270                 275                 280

TTC CCA TTT TCA ATT GAC CAG GAA GGA GAT ATT TAC GTG ACT CAG CCC       978
Phe Pro Phe Ser Ile Asp Gln Glu Gly Asp Ile Tyr Val Thr Gln Pro
                285                 290                 295

TTG GAC CGA GAA GAA AAG GAT GCA TAT GTT TTT TAT GCA GTT GCA AAG      1026
Leu Asp Arg Glu Glu Lys Asp Ala Tyr Val Phe Tyr Ala Val Ala Lys
            300                 305                 310

GAT GAG TAC GGA AAA CCA CTT TCA TAT CCG CTG GAA ATT CAT GTA AAA      1074
Asp Glu Tyr Gly Lys Pro Leu Ser Tyr Pro Leu Glu Ile His Val Lys
            315                 320                 325

GTT AAA GAT ATT AAT GAT AAT CCA CCT ACA TGT CCG TCA CCA GTA ACC      1122
Val Lys Asp Ile Asn Asp Asn Pro Pro Thr Cys Pro Ser Pro Val Thr
330                 335                 340                 345

GTA TTT GAG GTC CAG GAG AAT GAA CGA CTG GGT AAC AGT ATC GGG ACC      1170
Val Phe Glu Val Gln Glu Asn Glu Arg Leu Gly Asn Ser Ile Gly Thr
                350                 355                 360

CTT ACT GCA CAT GAC AGG GAT GAA GAA AAT ACT GCC AAC AGT TTT CTA      1218
Leu Thr Ala His Asp Arg Asp Glu Glu Asn Thr Ala Asn Ser Phe Leu
                365                 370                 375

AAC TAC AGG ATT GTG GAG CAA ACT CCC AAA CTT CCC ATG GAT GGA CTC      1266
Asn Tyr Arg Ile Val Glu Gln Thr Pro Lys Leu Pro Met Asp Gly Leu
            380                 385                 390

TTC CTA ATC CAA ACC TAT GCT GGA ATG TTA CAG TTA GCT AAA CAG TCC      1314
Phe Leu Ile Gln Thr Tyr Ala Gly Met Leu Gln Leu Ala Lys Gln Ser
            395                 400                 405

TTG AAG AAG CAA GAT ACT CCT CAG TAC AAC TTA ACG ATA GAG GTG TCT      1362
Leu Lys Lys Gln Asp Thr Pro Gln Tyr Asn Leu Thr Ile Glu Val Ser
410                 415                 420                 425
```

-continued

```
GAC AAA GAT TTC AAG ACC CTT TGT TTT GTG CAA ATC AAC GTT ATT GAT     1410
Asp Lys Asp Phe Lys Thr Leu Cys Phe Val Gln Ile Asn Val Ile Asp
            430                 435                 440

ATC AAT GAT CAG ATC CCC ATC TTT GAA AAA TCA GAT TAT GGA AAC CTG     1458
Ile Asn Asp Gln Ile Pro Ile Phe Glu Lys Ser Asp Tyr Gly Asn Leu
            445                 450                 455

ACT CTT GCT GAA GAC ACA AAC ATT GGG TCC ACC ATC TTA ACC ATC CAG     1506
Thr Leu Ala Glu Asp Thr Asn Ile Gly Ser Thr Ile Leu Thr Ile Gln
            460                 465                 470

GCC ACT GAT GCT GAT GAG CCA TTT ACT GGG AGT TCT AAA ATT CTG TAT     1554
Ala Thr Asp Ala Asp Glu Pro Phe Thr Gly Ser Ser Lys Ile Leu Tyr
    475                 480                 485

CAT ATC ATA AAG GGA GAC AGT GAG GGA CGC CTG GGG GTT GAC ACA GAT     1602
His Ile Ile Lys Gly Asp Ser Glu Gly Arg Leu Gly Val Asp Thr Asp
490                 495                 500                 505

CCC CAT ACC AAC ACC GGA TAT GTC ATA ATT AAA AAG CCT CTT GAT TTT     1650
Pro His Thr Asn Thr Gly Tyr Val Ile Ile Lys Lys Pro Leu Asp Phe
                510                 515                 520

GAA ACA GCA GCT GTT TCC AAC ATT GTG TTC AAA GCA GAA AAT CCT GAG     1698
Glu Thr Ala Ala Val Ser Asn Ile Val Phe Lys Ala Glu Asn Pro Glu
            525                 530                 535

CCT CTA GTG TTT GGT GTG AAG TAC AAT GCA AGT TCT TTT GCC AAG TTC     1746
Pro Leu Val Phe Gly Val Lys Tyr Asn Ala Ser Ser Phe Ala Lys Phe
            540                 545                 550

ACG CTT ATT GTG ACA GAT GTG AAT GAA GCA CCT CAA TTT TCC CAA CAC     1794
Thr Leu Ile Val Thr Asp Val Asn Glu Ala Pro Gln Phe Ser Gln His
    555                 560                 565

GTA TTC CAA GCG AAA GTC AGT GAG GAT GTA GCT ATA GGC ACT AAA GTG     1842
Val Phe Gln Ala Lys Val Ser Glu Asp Val Ala Ile Gly Thr Lys Val
570                 575                 580                 585

GGC AAT GTG ACT GCC AAG GAT CCA GAA GGT CTG GAC ATA AGC TAT TCA     1890
Gly Asn Val Thr Ala Lys Asp Pro Glu Gly Leu Asp Ile Ser Tyr Ser
                590                 595                 600

CTG AGG GGA GAC ACA AGA GGT TGG CTT AAA ATT GAC CAC GTG ACT GGT     1938
Leu Arg Gly Asp Thr Arg Gly Trp Leu Lys Ile Asp His Val Thr Gly
            605                 610                 615

GAG ATC TTT AGT GTG GCT CCA TTG GAC AGA GAA GCC GGA AGT CCA TAT     1986
Glu Ile Phe Ser Val Ala Pro Leu Asp Arg Glu Ala Gly Ser Pro Tyr
            620                 625                 630

CGG GTA CAA GTG GTG GCC ACA GAA GTA GGG GGG TCT TCC TTA AGC TCT     2034
Arg Val Gln Val Val Ala Thr Glu Val Gly Gly Ser Ser Leu Ser Ser
    635                 640                 645

GTG TCA GAG TTC CAC CTG ATC CTT ATG GAT GTG AAT GAC AAC CCT CCC     2082
Val Ser Glu Phe His Leu Ile Leu Met Asp Val Asn Asp Asn Pro Pro
650                 655                 660                 665

AGG CTA GCC AAG GAC TAC ACG GGC TTG TTC TTC TGC CAT CCC CTC AGT     2130
Arg Leu Ala Lys Asp Tyr Thr Gly Leu Phe Phe Cys His Pro Leu Ser
                670                 675                 680

GCA CCT GGA AGT CTC ATT TTC GAG GCT ACT GAT GAT GAT CAG CAC TTA     2178
Ala Pro Gly Ser Leu Ile Phe Glu Ala Thr Asp Asp Asp Gln His Leu
            685                 690                 695

TTT CGG GGT CCC CAT TTT ACA TTT TCC CTC GGC AGT GGA AGC TTA CAA     2226
Phe Arg Gly Pro His Phe Thr Phe Ser Leu Gly Ser Gly Ser Leu Gln
            700                 705                 710

AAC GAC TGG GAA GTT TCC AAA ATC AAT GGT ACT CAT GCC CGA CTG TCT     2274
Asn Asp Trp Glu Val Ser Lys Ile Asn Gly Thr His Ala Arg Leu Ser
            715                 720                 725

ACC AGG CAC ACA GAC TTT GAG GAG AGG GCG TAT GTC GTC TTG ATC CGC     2322
Thr Arg His Thr Asp Phe Glu Glu Arg Ala Tyr Val Val Leu Ile Arg
730                 735                 740                 745
```

```
ATC AAT GAT GGG GGT CGG CCA CCC TTG GAA GGC ATT GTT TCT TTA CCA    2370
Ile Asn Asp Gly Gly Arg Pro Pro Leu Glu Gly Ile Val Ser Leu Pro
                750                 755                 760

GTT ACA TTC TGC AGT TGT GTG GAA GGA AGT TGT TTC CGG CCA GCA GGT    2418
Val Thr Phe Cys Ser Cys Val Glu Gly Ser Cys Phe Arg Pro Ala Gly
            765                 770                 775

CAC CAG ACT GGG ATA CCC ACT GTG GGC ATG GCA GTT GGT ATA CTG CTG    2466
His Gln Thr Gly Ile Pro Thr Val Gly Met Ala Val Gly Ile Leu Leu
                780                 785                 790

ACC ACC CTT CTG GTG ATT GGT ATA ATT TTA GCA GTT GTG TTT ATC CGC    2514
Thr Thr Leu Leu Val Ile Gly Ile Ile Leu Ala Val Val Phe Ile Arg
        795                 800                 805

ATA AAG AAG GAT AAA GGC AAA GAT AAT GTT GAA AGT GCT CAA GCA TCT    2562
Ile Lys Lys Asp Lys Gly Lys Asp Asn Val Glu Ser Ala Gln Ala Ser
810                 815                 820                 825

GAA GTC AAA CCT CTG AGA AGC TGAATTTGAA AAGGAATGTT TGAATTTATA TAGC   2617
Glu Val Lys Pro Leu Arg Ser
                830

AAGTGCTATT TCAGCAACAA CCATCTCATC CTATTACTTT TCATCTAACG TGCATTATAA   2677

TTTTTTAAAC AGATATTCCC TCTTGTCCTT TAATATTTGC TAAATATTTC TTTTTTGAGG   2737

TGGAGTCTTG CTCTGTCGCC CAGGCTGGAG TACAGTGGTG TGATCCCAGC TCACTGCAAC   2797

CTCCGCCTCC TGGGTTCACA TGATTCTCCT GCCTCAGCTT CCTAAGTAGC TGGGTTTACA   2857

GGCACCCACC ACCATGCCCA GCTAATTTTT GTATTTTTAA TAGAGACGGG GTTTCGCCAT   2917

TTGGCCAGGC TGGTCTTGAA CTCCTGACGT CAAGTGATCT GCCTGCCTTG GTCTCCCAAT   2977

ACAGGCATGA ACCACTGCAC CCACCTACTT AGATATTTCA TGTGCTATAG ACATTAGAGA   3037

GATTTTTCAT TTTTCCATGA CATTTTTCCT CTCTGCAAAT GGCTTAGCTA CTTGTGTTTT   3097

TCCCTTTTGG GGCAAGACAG ACTCATTAAA TATTCTGTAC ATTTTTTCTT TATCAAGGAG   3157

ATATATCAGT GTTGTCTCAT AGAACTGCCT GGATTCCATT TATGTTTTTT CTGATTCCAT   3217

CCTGTGTCCC CTTCATCCTT GACTCCTTTG GTATTTCACT GAATTTCAAA CATTTGTCAG   3277

AGAAGAAAAA AGTGAGGACT CAGGAAAAAT AAATAAATAA AAGAACAGCC TTTTGCGGCC   3337

GCGAATTC                                                            3345

(2) INFORMATION FOR SEQ ID NO: 178:

(i) SEQUENCE CHARACTERISTICS:
        (A) LENGTH: 832 amino acids
        (B) TYPE: amino acid
        (C) STRANDEDNESS: <Unknown>
        (D) TOPOLOGY: unknown (ii) MOLECULE TYPE: protein (xi) SEQUENCE DESCRIPTION: SEQ ID NO: 178:

Met Ile Leu Gln Ala His Leu His Ser Leu Cys Leu Leu Met Leu Tyr
  1               5                  10                  15

Leu Ala Thr Gly Tyr Gly Gln Glu Gly Lys Phe Ser Gly Pro Leu Lys
               20                  25                  30

Pro Met Thr Phe Ser Ile Tyr Glu Gly Gln Glu Pro Ser Gln Ile Ile
           35                  40                  45

Phe Gln Phe Lys Ala Asn Pro Pro Ala Val Thr Phe Glu Leu Thr Gly
       50                  55                  60

Glu Thr Asp Asn Ile Phe Val Ile Glu Arg Gly Leu Leu Tyr Tyr
 65                  70                  75                  80
```

-continued

```
Asn Arg Ala Leu Asp Arg Glu Thr Arg Ser Thr His Asn Leu Gln Val
                 85                  90                  95

Ala Ala Leu Asp Ala Asn Gly Ile Ile Val Glu Gly Pro Val Pro Ile
                100                 105                 110

Thr Ile Glu Val Lys Asp Ile Asn Asp Asn Arg Pro Thr Phe Leu Gln
                115                 120                 125

Ser Lys Tyr Glu Gly Ser Val Arg Gln Asn Ser Arg Pro Gly Lys Pro
        130                 135                 140

Phe Leu Tyr Val Asn Ala Thr Asp Leu Asp Asp Pro Ala Thr Pro Asn
145                 150                 155                 160

Gly Gln Leu Tyr Tyr Gln Ile Val Ile Gln Leu Pro Met Ile Asn Asn
                    165                 170                 175

Val Met Tyr Phe Gln Ile Asn Asn Lys Thr Gly Ala Ile Ser Leu Thr
                180                 185                 190

Arg Glu Gly Ser Gln Glu Leu Asn Pro Ala Lys Asn Pro Ser Tyr Asn
                195                 200                 205

Leu Val Ile Ser Val Lys Asp Met Gly Gly Gln Ser Glu Asn Ser Phe
            210                 215                 220

Ser Asp Thr Thr Ser Val Asp Ile Ile Val Thr Glu Asn Ile Trp Lys
225                 230                 235                 240

Ala Pro Lys Pro Val Glu Met Val Glu Asn Ser Thr Asp Pro His Pro
                245                 250                 255

Ile Lys Ile Thr Gln Val Arg Trp Asn Asp Pro Gly Ala Gln Tyr Ser
                260                 265                 270

Leu Val Asp Lys Glu Lys Leu Pro Arg Phe Pro Phe Ser Ile Asp Gln
            275                 280                 285

Glu Gly Asp Ile Tyr Val Thr Gln Pro Leu Asp Arg Glu Glu Lys Asp
            290                 295                 300

Ala Tyr Val Phe Tyr Ala Val Ala Lys Asp Glu Tyr Gly Lys Pro Leu
305                 310                 315                 320

Ser Tyr Pro Leu Glu Ile His Val Lys Val Lys Asp Ile Asn Asp Asn
                325                 330                 335

Pro Pro Thr Cys Pro Ser Pro Val Thr Val Phe Glu Val Gln Glu Asn
                340                 345                 350

Glu Arg Leu Gly Asn Ser Ile Gly Thr Leu Thr Ala His Asp Arg Asp
            355                 360                 365

Glu Glu Asn Thr Ala Asn Ser Phe Leu Asn Tyr Arg Ile Val Glu Gln
            370                 375                 380

Thr Pro Lys Leu Pro Met Asp Gly Leu Phe Leu Ile Gln Thr Tyr Ala
385                 390                 395                 400

Gly Met Leu Gln Leu Ala Lys Gln Ser Leu Lys Lys Gln Asp Thr Pro
                405                 410                 415

Gln Tyr Asn Leu Thr Ile Glu Val Ser Asp Lys Asp Phe Lys Thr Leu
            420                 425                 430

Cys Phe Val Gln Ile Asn Val Ile Asp Ile Asn Asp Gln Ile Pro Ile
            435                 440                 445

Phe Glu Lys Ser Asp Tyr Gly Asn Leu Thr Leu Ala Glu Asp Thr Asn
        450                 455                 460

Ile Gly Ser Thr Ile Leu Thr Ile Gln Ala Thr Asp Ala Asp Glu Pro
465                 470                 475                 480

Phe Thr Gly Ser Ser Lys Ile Leu Tyr His Ile Ile Lys Gly Asp Ser
                485                 490                 495
```

-continued

```
Glu Gly Arg Leu Gly Val Asp Thr Asp Pro His Thr Asn Thr Gly Tyr
            500                 505                 510

Val Ile Ile Lys Lys Pro Leu Asp Phe Glu Thr Ala Ala Val Ser Asn
            515                 520                 525

Ile Val Phe Lys Ala Glu Asn Pro Glu Pro Leu Val Phe Gly Val Lys
        530                 535                 540

Tyr Asn Ala Ser Ser Phe Ala Lys Phe Thr Leu Ile Val Thr Asp Val
545                 550                 555                 560

Asn Glu Ala Pro Gln Phe Ser Gln His Val Phe Gln Ala Lys Val Ser
            565                 570                 575

Glu Asp Val Ala Ile Gly Thr Lys Val Gly Asn Val Thr Ala Lys Asp
            580                 585                 590

Pro Glu Gly Leu Asp Ile Ser Tyr Ser Leu Arg Gly Asp Thr Arg Gly
        595                 600                 605

Trp Leu Lys Ile Asp His Val Thr Gly Glu Ile Phe Ser Val Ala Pro
    610                 615                 620

Leu Asp Arg Glu Ala Gly Ser Pro Tyr Arg Val Gln Val Val Ala Thr
625                 630                 635                 640

Glu Val Gly Gly Ser Ser Leu Ser Ser Val Ser Glu Phe His Leu Ile
            645                 650                 655

Leu Met Asp Val Asn Asp Asn Pro Pro Arg Leu Ala Lys Asp Tyr Thr
            660                 665                 670

Gly Leu Phe Phe Cys His Pro Leu Ser Ala Pro Gly Ser Leu Ile Phe
        675                 680                 685

Glu Ala Thr Asp Asp Gln His Leu Phe Arg Gly Pro His Phe Thr
        690                 695                 700

Phe Ser Leu Gly Ser Gly Ser Leu Gln Asn Asp Trp Glu Val Ser Lys
705                 710                 715                 720

Ile Asn Gly Thr His Ala Arg Leu Ser Thr Arg His Thr Asp Phe Glu
            725                 730                 735

Glu Arg Ala Tyr Val Val Leu Ile Arg Ile Asn Asp Gly Gly Arg Pro
            740                 745                 750

Pro Leu Glu Gly Ile Val Ser Leu Pro Val Thr Phe Cys Ser Cys Val
        755                 760                 765

Glu Gly Ser Cys Phe Arg Pro Ala Gly His Gln Thr Gly Ile Pro Thr
770                 775                 780

Val Gly Met Ala Val Gly Ile Leu Leu Thr Thr Leu Val Ile Gly
785                 790                 795                 800

Ile Ile Leu Ala Val Val Phe Ile Arg Ile Lys Lys Asp Lys Gly Lys
            805                 810                 815

Asp Asn Val Glu Ser Ala Gln Ala Ser Glu Val Lys Pro Leu Arg Ser
            820                 825                 830
```

(2) INFORMATION FOR SEQ ID NO: 179:

(i) SEQUENCE CHARACTERISTICS:
        (A) LENGTH: 1827 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 179:

```
Met Ala Arg Lys Lys Phe Ser Gly Leu Glu Ile Ser Leu Ile Val Leu
1               5                   10                  15
```

-continued

```
Phe Val Ile Val Thr Ile Ile Ala Ile Ala Leu Ile Val Val Leu Ala
             20                  25                  30
Thr Lys Thr Pro Ala Val Asp Glu Ile Ser Asp Ser Thr Ser Thr Pro
         35                  40                  45
Ala Thr Thr Arg Val Thr Thr Asn Pro Ser Asp Ser Gly Lys Cys Pro
     50                  55                  60
Asn Val Leu Asn Asp Pro Val Asn Val Arg Ile Asn Cys Ile Pro Glu
 65                  70                  75                  80
Gln Phe Pro Thr Glu Gly Ile Cys Ala Gln Arg Gly Cys Cys Trp Arg
                 85                  90                  95
Pro Trp Asn Asp Ser Leu Ile Pro Trp Cys Phe Phe Val Asp Asn His
             100                 105                 110
Gly Tyr Asn Val Gln Asp Met Thr Thr Thr Ser Ile Gly Val Glu Ala
         115                 120                 125
Lys Leu Asn Arg Ile Pro Ser Pro Thr Leu Phe Gly Asn Asp Ile Asn
     130                 135                 140
Ser Val Leu Phe Thr Thr Gln Asn Gln Thr Pro Asn Arg Phe Arg Phe
145                 150                 155                 160
Lys Ile Thr Asp Pro Asn Asn Arg Arg Tyr Glu Val Pro His Gln Tyr
                 165                 170                 175
Val Lys Glu Phe Thr Gly Pro Thr Val Ser Asp Thr Leu Tyr Asp Val
             180                 185                 190
Lys Val Ala Gln Asn Pro Phe Ser Ile Gln Val Ile Arg Lys Ser Asn
         195                 200                 205
Gly Lys Thr Leu Phe Asp Thr Ser Ile Gly Pro Leu Val Tyr Ser Asp
     210                 215                 220
Gln Tyr Leu Gln Ile Ser Ala Arg Leu Pro Ser Asp Tyr Ile Tyr Gly
225                 230                 235                 240
Ile Gly Glu Gln Val His Lys Arg Phe Arg His Asp Leu Ser Trp Lys
                 245                 250                 255
Thr Trp Pro Ile Phe Thr Arg Asp Gln Leu Pro Gly Asp Asn Asn Asn
             260                 265                 270
Asn Leu Tyr Gly His Gln Thr Phe Phe Met Cys Ile Glu Asp Thr Ser
         275                 280                 285
Gly Lys Ser Phe Gly Val Phe Leu Met Asn Ser Asn Ala Met Glu Ile
     290                 295                 300
Phe Ile Gln Pro Thr Pro Ile Val Thr Tyr Arg Val Thr Gly Gly Ile
305                 310                 315                 320
Leu Asp Phe Tyr Ile Leu Leu Gly Asp Thr Pro Glu Gln Val Val Gln
                 325                 330                 335
Gln Tyr Gln Gln Leu Val Gly Leu Pro Ala Met Pro Ala Tyr Trp Asn
             340                 345                 350
Leu Gly Phe Gln Leu Ser Arg Trp Asn Tyr Lys Ser Leu Asp Val Val
         355                 360                 365
Lys Glu Val Val Arg Arg Asn Arg Glu Ala Gly Ile Pro Phe Asp Thr
     370                 375                 380
Gln Val Thr Asp Ile Asp Tyr Met Glu Asp Lys Lys Asp Phe Thr Tyr
385                 390                 395                 400
Asp Gln Val Ala Phe Asn Gly Leu Pro Gln Phe Val Gln Asp Leu His
                 405                 410                 415
Asp His Gly Gln Lys Tyr Val Ile Ile Leu Asp Pro Ala Ile Ser Ile
             420                 425                 430
```

```
Gly Arg Arg Ala Asn Gly Thr Thr Tyr Ala Thr Tyr Glu Arg Gly Asn
        435                 440                 445

Thr Gln His Val Trp Ile Asn Glu Ser Asp Gly Ser Thr Pro Ile Ile
    450                 455                 460

Gly Glu Val Trp Pro Gly Leu Thr Val Tyr Pro Asp Phe Thr Asn Pro
465                 470                 475                 480

Asn Cys Ile Asp Trp Trp Ala Asn Glu Cys Ser Ile Phe His Gln Glu
                485                 490                 495

Val Gln Tyr Asp Gly Leu Trp Ile Asp Met Asn Glu Val Ser Ser Phe
            500                 505                 510

Ile Gln Gly Ser Thr Lys Gly Cys Asn Val Asn Lys Leu Asn Tyr Pro
        515                 520                 525

Pro Phe Thr Pro Asp Ile Leu Asp Lys Leu Met Tyr Ser Lys Thr Ile
    530                 535                 540

Cys Met Asp Ala Val Gln Asn Trp Gly Lys Gln Tyr Asp Val His Ser
545                 550                 555                 560

Leu Tyr Gly Tyr Ser Met Ala Ile Ala Thr Glu Gln Ala Val Gln Lys
                565                 570                 575

Val Phe Pro Asn Lys Arg Ser Phe Ile Leu Thr Arg Ser Thr Phe Ala
            580                 585                 590

Gly Ser Gly Arg His Ala Ala His Trp Leu Gly Asp Asn Thr Ala Ser
        595                 600                 605

Trp Glu Gln Met Glu Trp Ser Ile Thr Gly Met Leu Glu Phe Ser Leu
    610                 615                 620

Phe Gly Ile Pro Leu Val Gly Ala Asp Ile Cys Gly Phe Val Ala Glu
625                 630                 635                 640

Thr Thr Glu Glu Leu Cys Arg Arg Trp Met Gln Leu Gly Ala Phe Tyr
                645                 650                 655

Pro Phe Ser Arg Asn His Asn Ser Asp Gly Tyr Glu His Gln Asp Pro
            660                 665                 670

Ala Phe Phe Gly Gln Asn Ser Leu Leu Val Lys Ser Ser Arg Gln Tyr
        675                 680                 685

Leu Thr Ile Arg Tyr Thr Leu Leu Pro Phe Leu Tyr Thr Leu Phe Tyr
    690                 695                 700

Lys Ala His Val Phe Gly Glu Thr Val Ala Arg Pro Val Leu His Glu
705                 710                 715                 720

Phe Tyr Glu Asp Thr Asn Ser Trp Ile Glu Asp Thr Glu Phe Leu Trp
                725                 730                 735

Gly Pro Ala Leu Leu Ile Thr Pro Val Leu Lys Gln Gly Ala Asp Thr
            740                 745                 750

Val Ser Ala Tyr Ile Pro Asp Ala Ile Trp Tyr Asp Tyr Glu Ser Gly
        755                 760                 765

Ala Lys Arg Pro Trp Arg Lys Gln Arg Val Asp Met Tyr Leu Pro Ala
    770                 775                 780

Asp Lys Ile Gly Leu His Leu Arg Gly Gly Tyr Ile Ile Pro Ile Gln
785                 790                 795                 800

Glu Pro Asp Val Thr Thr Thr Ala Ser Arg Lys Asn Pro Leu Gly Leu
                805                 810                 815

Ile Val Ala Leu Gly Glu Asn Asn Thr Ala Lys Gly Asp Phe Phe Trp
            820                 825                 830

Asp Asp Gly Glu Thr Lys Asp Thr Ile Gln Asn Gly Asn Tyr Ile Leu
        835                 840                 845
```

```
Tyr Thr Phe Ser Val Ser Asn Asn Thr Leu Asp Ile Val Cys Thr His
850                 855                 860

Ser Ser Tyr Gln Glu Gly Thr Thr Leu Ala Phe Gln Thr Val Lys Ile
865                 870                 875                 880

Leu Gly Leu Thr Asp Ser Val Thr Glu Val Arg Val Ala Glu Asn Asn
                885                 890                 895

Gln Pro Met Asn Ala His Ser Asn Phe Thr Tyr Asp Ala Ser Asn Gln
            900                 905                 910

Val Leu Leu Ile Ala Asp Leu Lys Leu Asn Leu Gly Arg Asn Phe Ser
        915                 920                 925

Val Gln Trp Asn Gln Ile Phe Ser Glu Asn Glu Arg Phe Asn Cys Tyr
    930                 935                 940

Pro Asp Ala Asp Leu Ala Thr Glu Gln Lys Cys Thr Gln Arg Gly Cys
945                 950                 955                 960

Val Trp Arg Thr Gly Ser Ser Leu Ser Lys Ala Pro Glu Cys Tyr Phe
                965                 970                 975

Pro Arg Gln Asp Asn Ser Tyr Ser Val Asn Ser Ala Arg Tyr Ser Ser
                980                 985                 990

Met Gly Ile Thr Ala Asp Leu Gln Leu Asn Thr Ala Asn Ala Arg Ile
            995                 1000                1005

Lys Leu Pro Ser Asp Pro Ile Ser Thr Leu Arg Val Glu Val Lys Tyr
    1010                1015                1020

His Lys Asn Asp Met Leu Gln Phe Lys Ile Tyr Asp Pro Gln Lys Lys
1025                1030                1035                1040

Arg Tyr Glu Val Pro Val Pro Leu Asn Ile Pro Thr Thr Pro Ile Ser
                1045                1050                1055

Thr Tyr Glu Asp Arg Leu Tyr Asp Val Glu Ile Lys Gly Asn Pro Phe
            1060                1065                1070

Gly Ile Gln Ile Arg Arg Arg Ser Ser Gly Arg Val Ile Trp Asp Ser
        1075                1080                1085

Trp Leu Pro Gly Phe Ala Phe Asn Asp Gln Phe Ile Gln Ile Ser Thr
    1090                1095                1100

Arg Leu Pro Ser Glu Tyr Ile Tyr Gly Phe Gly Glu Val Glu His Thr
1105                1110                1115                1120

Ala Phe Lys Arg Asp Leu Asn Trp Asn Thr Trp Gly Met Phe Thr Arg
                1125                1130                1135

Asp Gln Pro Pro Gly Tyr Lys Leu Asn Ser Tyr Gly Phe His Pro Tyr
            1140                1145                1150

Tyr Met Ala Leu Glu Glu Glu Gly Asn Ala His Gly Val Phe Leu Leu
        1155                1160                1165

Asn Ser Asn Ala Met Asp Val Thr Phe Gln Pro Thr Pro Ala Leu Thr
    1170                1175                1180

Tyr Arg Thr Val Gly Gly Ile Leu Asp Phe Tyr Met Phe Leu Gly Pro
1185                1190                1195                1200

Thr Pro Gln Val Ala Thr Lys Gln Tyr His Glu Val Ile Gly His Pro
                1205                1210                1215

Val Met Pro Ala Tyr Trp Ala Leu Gly Phe Gln Leu Cys Arg Tyr Gly
            1220                1225                1230

Tyr Ala Asn Thr Ser Glu Val Arg Glu Leu Tyr Asp Ala Met Val Ala
        1235                1240                1245

Ala Asn Ile Pro Tyr Asp Val Gln Tyr Thr Asp Ile Asp Tyr Met Glu
    1250                1255                1260
```

-continued

```
Arg Gln Leu Asp Phe Thr Ile Gly Glu Ala Phe Gln Asp Leu Pro Gln
1265                1270                1275                1280

Phe Val Asp Lys Ile Arg Gly Glu Gly Met Arg Tyr Ile Ile Ile Leu
            1285                1290                1295

Asp Pro Ala Ile Ser Gly Asn Glu Thr Lys Thr Tyr Pro Ala Phe Glu
        1300                1305                1310

Arg Gly Gln Gln Asn Asp Val Phe Val Lys Trp Pro Asn Thr Asn Asp
    1315                1320                1325

Ile Cys Trp Ala Lys Val Trp Pro Asp Leu Pro Asn Ile Thr Ile Asp
1330                1335                1340

Lys Thr Leu Thr Glu Asp Glu Ala Val Asn Ala Ser Arg Ala His Val
1345                1350                1355                1360

Ala Phe Pro Asp Phe Phe Arg Thr Ser Thr Ala Glu Trp Trp Ala Arg
            1365                1370                1375

Glu Ile Val Asp Phe Tyr Asn Glu Lys Met Lys Phe Asp Gly Leu Trp
        1380                1385                1390

Ile Asp Met Asn Glu Pro Ser Ser Phe Val Asn Gly Thr Thr Thr Asn
    1395                1400                1405

Gln Cys Arg Asn Asp Glu Leu Asn Tyr Pro Pro Tyr Phe Pro Glu Leu
1410                1415                1420

Thr Lys Arg Thr Asp Gly Leu His Phe Arg Thr Ile Cys Met Glu Ala
1425                1430                1435                1440

Glu Gln Ile Leu Ser Asp Gly Thr Ser Val Leu His Tyr Asp Val His
            1445                1450                1455

Asn Leu Tyr Gly Trp Ser Gln Met Lys Pro Thr His Asp Ala Leu Gln
        1460                1465                1470

Lys Thr Thr Gly Lys Arg Gly Ile Val Ile Ser Arg Ser Thr Tyr Pro
    1475                1480                1485

Thr Ser Gly Arg Trp Gly Gly His Trp Leu Gly Asp Asn Tyr Ala Arg
1490                1495                1500

Trp Asp Asn Met Asp Lys Ser Ile Ile Gly Met Met Glu Phe Ser Leu
1505                1510                1515                1520

Phe Gly Ile Ser Tyr Thr Gly Ala Asp Ile Cys Gly Phe Phe Asn Asn
            1525                1530                1535

Ser Glu Tyr His Leu Cys Thr Arg Trp Met Gln Leu Gly Ala Phe Tyr
        1540                1545                1550

Pro Tyr Ser Arg Asn His Asn Ile Ala Asn Thr Arg Arg Gln Asp Pro
    1555                1560                1565

Ala Ser Trp Asn Glu Thr Phe Ala Glu Met Ser Arg Asn Ile Leu Asn
1570                1575                1580

Ile Arg Tyr Thr Leu Leu Pro Tyr Phe Tyr Thr Gln Met His Glu Ile
1585                1590                1595                1600

His Ala Asn Gly Gly Thr Val Ile Arg Pro Leu Leu His Glu Phe Phe
            1605                1610                1615

Asp Glu Lys Pro Thr Trp Asp Ile Phe Lys Gln Phe Leu Trp Gly Pro
        1620                1625                1630

Ala Phe Met Val Thr Pro Val Leu Glu Pro Tyr Val Gln Thr Val Asn
    1635                1640                1645

Ala Tyr Val Pro Asn Ala Arg Trp Phe Asp Tyr His Thr Gly Lys Asp
1650                1655                1660

Ile Gly Val Arg Gly Gln Phe Gln Thr Phe Asn Ala Ser Tyr Asp Thr
1665                1670                1675                1680
```

-continued

```
Ile Asn Leu His Val Arg Gly Gly His Ile Leu Pro Cys Gln Glu Pro
            1685                1690                1695

Ala Gln Asn Thr Phe Tyr Ser Arg Gln Lys His Met Lys Leu Ile Val
        1700                1705                1710

Ala Ala Asp Asp Asn Gln Met Ala Gln Gly Ser Leu Phe Trp Asp Asp
    1715                1720                1725

Gly Glu Ser Ile Asp Thr Tyr Glu Arg Asp Leu Tyr Leu Ser Val Gln
    1730                1735                1740

Phe Asn Leu Asn Gln Thr Thr Leu Thr Ser Thr Ile Leu Lys Arg Gly
1745                1750                1755                1760

Tyr Ile Asn Lys Ser Glu Thr Arg Leu Gly Ser Leu His Val Trp Gly
            1765                1770                1775

Lys Gly Thr Thr Pro Val Asn Ala Val Thr Leu Thr Tyr Asn Gly Asn
            1780                1785                1790

Lys Asn Ser Leu Pro Phe Asn Glu Asp Thr Thr Asn Met Ile Leu Arg
        1795                1800                1805

Ile Asp Leu Thr Thr His Asn Val Thr Leu Glu Glu Pro Ile Glu Ile
    1810                1815                1820

Asn Trp Ser
1825
```

(2) INFORMATION FOR SEQ ID NO: 180:

(i) SEQUENCE CHARACTERISTICS:
        (A) LENGTH: 2284 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: Coding Sequence
        (B) LOCATION: 45...2099
        (D) OTHER INFORMATION:

(xi) SEQUENCE DESCRIPTION: SEQ ID NO: 180:

```
GCCTTACTGC AGGAAGGCAC TCCGAAGACA TAAGTCGGTG AGAC ATG GCT GAA GAT        56
                                               Met Ala Glu Asp
                                                 1

AAA AGC AAG AGA GAC TCC ATC GAG ATG AGT ATG AAG GGA TGC CAG ACA        104
Lys Ser Lys Arg Asp Ser Ile Glu Met Ser Met Lys Gly Cys Gln Thr
 5              10                  15                  20

AAC AAC GGG TTT GTC CAT AAT GAA GAC ATT CTG GAG CAG ACC CCG GAT        152
Asn Asn Gly Phe Val His Asn Glu Asp Ile Leu Glu Gln Thr Pro Asp
                25                  30                  35

CCA GGC AGC TCA ACA GAC AAC CTG AAG CAC AGC ACC AGG GGC ATC CTT        200
Pro Gly Ser Ser Thr Asp Asn Leu Lys His Ser Thr Arg Gly Ile Leu
        40                  45                  50

GGC TCC CAG GAG CCC GAC TTC AAG GGC GTC CAG CCC TAT GCG GGG ATG        248
Gly Ser Gln Glu Pro Asp Phe Lys Gly Val Gln Pro Tyr Ala Gly Met
    55                  60                  65

CCC AAG GAG GTG CTG TTC CAG TTC TCT GGC CAG GCC CGC TAC CGC ATA        296
Pro Lys Glu Val Leu Phe Gln Phe Ser Gly Gln Ala Arg Tyr Arg Ile
70                  75                  80

CCT CGG GAG ATC CTC TTC TGG CTC ACA GTG GCT TCT GTG CTG GTG CTC        344
Pro Arg Glu Ile Leu Phe Trp Leu Thr Val Ala Ser Val Leu Val Leu
85                  90                  95                  100

ATC GCG GCC ACC ATA GCC ATC ATT GCC CTC TCT CCA AAG TGC CTA GAC        392
Ile Ala Ala Thr Ile Ala Ile Ile Ala Leu Ser Pro Lys Cys Leu Asp
                105                 110                 115
```

-continued

| | | |
|---|---|---|
| TGG TGG CAG GAG GGG CCC ATG TAC CAG ATC TAC CCA AGG TCT TTC AAG<br>Trp Trp Gln Glu Gly Pro Met Tyr Gln Ile Tyr Pro Arg Ser Phe Lys<br>120                         125                         130 | | 440 |
| GAC AGT AAC AAG GAT GGG AAC GGA GAT CTG AAA GGT ATT CAA GAT AAA<br>Asp Ser Asn Lys Asp Gly Asn Gly Asp Leu Lys Gly Ile Gln Asp Lys<br>         135                       140                       145 | | 488 |
| CTG GAC TAC ATC ACA GCT TTA AAT ATA AAA ACT GTT TGG ATT ACT TCA<br>Leu Asp Tyr Ile Thr Ala Leu Asn Ile Lys Thr Val Trp Ile Thr Ser<br>150                         155                         160 | | 536 |
| TTT TAT AAA TCG TCC CTT AAA GAT TTC AGA TAT GGT GTT GAA GAT TTC<br>Phe Tyr Lys Ser Ser Leu Lys Asp Phe Arg Tyr Gly Val Glu Asp Phe<br>165                       170                       175                 180 | | 584 |
| CGG GAA GTT GAT CCC ATT TTT GGA ACG ATG GAA GAT TTT GAG AAT CTG<br>Arg Glu Val Asp Pro Ile Phe Gly Thr Met Glu Asp Phe Glu Asn Leu<br>                   185                       190                     195 | | 632 |
| GTT GCA GCC ATA CAT GAT AAA GGT TTA AAA TTA ATC ATC GAT TTC ATA<br>Val Ala Ala Ile His Asp Lys Gly Leu Lys Leu Ile Ile Asp Phe Ile<br>                    200                       205                     210 | | 680 |
| CCA AAC CAC ACG AGT GAT AAA CAT ATT TGG TTT CAA TTG AGT CGG ACA<br>Pro Asn His Thr Ser Asp Lys His Ile Trp Phe Gln Leu Ser Arg Thr<br>              215                       220                     225 | | 728 |
| CGG ACA GGA AAA TAT ACT GAT TAT TAT ATC TGG CAT GAC TGT ACC CAT<br>Arg Thr Gly Lys Tyr Thr Asp Tyr Tyr Ile Trp His Asp Cys Thr His<br>230                         235                       240 | | 776 |
| GAA AAT GGC AAA ACC ATT CCA CCC AAC AAC TGG TTA AGT GTG TAT GGA<br>Glu Asn Gly Lys Thr Ile Pro Pro Asn Asn Trp Leu Ser Val Tyr Gly<br>245                       250                       255                 260 | | 824 |
| AAC TCC AGT TGG CAC TTT GAC GAA GTG CGA AAC CAA TGT TAT TTT CAT<br>Asn Ser Ser Trp His Phe Asp Glu Val Arg Asn Gln Cys Tyr Phe His<br>                   265                       270                     275 | | 872 |
| CAG TTT ATG AAA GAG CAA CCT GAT TTA AAT TTC CGC AAT CCT GAT GTT<br>Gln Phe Met Lys Glu Gln Pro Asp Leu Asn Phe Arg Asn Pro Asp Val<br>                   280                       285                     290 | | 920 |
| CAA GAA GAA ATA AAA GAA ATT TTA CGG TTC TGG CTC ACA AAG GGT GTT<br>Gln Glu Glu Ile Lys Glu Ile Leu Arg Phe Trp Leu Thr Lys Gly Val<br>              295                       300                     305 | | 968 |
| GAT GGT TTT AGT TTG GAT GCT GTT AAA TTC CTC CTA GAA GCA AAG CAC<br>Asp Gly Phe Ser Leu Asp Ala Val Lys Phe Leu Leu Glu Ala Lys His<br>310                         315                         320 | | 1016 |
| CTG AGA GAT GAG ATC CAA GTA AAT AAG ACC CAA ATC CCG GAC ACG GTC<br>Leu Arg Asp Glu Ile Gln Val Asn Lys Thr Gln Ile Pro Asp Thr Val<br>325                         330                       335                 340 | | 1064 |
| ACA CAA TAC TCG GAG CTG TAC CAT GAC TTC ACC ACC ACG CAG GTG GGA<br>Thr Gln Tyr Ser Glu Leu Tyr His Asp Phe Thr Thr Thr Gln Val Gly<br>                   345                       350                     355 | | 1112 |
| ATG CAC GAC ATT GTC CGC AGC TTC CGG CAG ACC ATG GAC CAA TAC AGC<br>Met His Asp Ile Val Arg Ser Phe Arg Gln Thr Met Asp Gln Tyr Ser<br>                   360                       365                     370 | | 1160 |
| ACG GAG CCC GGC AGA TAC AGG TTC ATG GGG ACT GAA GCC TAT GCA GAG<br>Thr Glu Pro Gly Arg Tyr Arg Phe Met Gly Thr Glu Ala Tyr Ala Glu<br>              375                       380                     385 | | 1208 |
| AGT ATT GAC AGG ACC GTG ATG TAC TAT GGA TTG CCA TTT ATC CAA GAA<br>Ser Ile Asp Arg Thr Val Met Tyr Tyr Gly Leu Pro Phe Ile Gln Glu<br>390                         395                       400 | | 1256 |
| GCT GAT TTT CCC TTC AAC AAT TAC CTC AGC ATG CTA GAC ACT GTT TCT<br>Ala Asp Phe Pro Phe Asn Asn Tyr Leu Ser Met Leu Asp Thr Val Ser<br>405                         410                       415                 420 | | 1304 |
| GGG AAC AGC GTG TAT GAG GTT ATC ACA TCC TGG ATG GAA AAC ATG CCA<br>Gly Asn Ser Val Tyr Glu Val Ile Thr Ser Trp Met Glu Asn Met Pro<br>                   425                       430                     435 | | 1352 |

```
GAA GGA AAA TGG CCT AAC TGG ATG ATT GGT GGA CCA GAC AGT TCA CGG      1400
Glu Gly Lys Trp Pro Asn Trp Met Ile Gly Gly Pro Asp Ser Ser Arg
            440                 445                 450

CTG ACT TCG CGT TTG GGG AAT CAG TAT GTC AAC GTG ATG AAC ATG CTT      1448
Leu Thr Ser Arg Leu Gly Asn Gln Tyr Val Asn Val Met Asn Met Leu
            455                 460                 465

CTT TTC ACA CTC CCT GGA ACT CCT ATA ACT TAC TAT GGA GAA GAA ATT      1496
Leu Phe Thr Leu Pro Gly Thr Pro Ile Thr Tyr Tyr Gly Glu Glu Ile
470                 475                 480

GGA ATG GGA AAT ATT GTA GCC GCA AAT CTC AAT GAA AGC TAT GAT ATT      1544
Gly Met Gly Asn Ile Val Ala Ala Asn Leu Asn Glu Ser Tyr Asp Ile
485                 490                 495                 500

AAT ACC CTT CGC TCA AAG TCA CCA ATG CAG TGG GAC AAT AGT TCA AAT      1592
Asn Thr Leu Arg Ser Lys Ser Pro Met Gln Trp Asp Asn Ser Ser Asn
            505                 510                 515

GCT GGT TTT TCT GAA GCT AGT AAC ACC TGG TTA CCT ACC AAT TCA GAT      1640
Ala Gly Phe Ser Glu Ala Ser Asn Thr Trp Leu Pro Thr Asn Ser Asp
            520                 525                 530

TAC CAC ACT GTG AAT GTT GAT GTC CAA AAG ACT CAG CCC AGA TCG GCT      1688
Tyr His Thr Val Asn Val Asp Val Gln Lys Thr Gln Pro Arg Ser Ala
            535                 540                 545

TTG AAG TTA TAT CAA GAT TTA AGT CTA CTT CAT GCC AAT GAG CTA CTC      1736
Leu Lys Leu Tyr Gln Asp Leu Ser Leu Leu His Ala Asn Glu Leu Leu
550                 555                 560

CTC AAC AGG GGC TGG TTT TGC CAT TTG AGG AAT GAC AGC CAC TAT GTT      1784
Leu Asn Arg Gly Trp Phe Cys His Leu Arg Asn Asp Ser His Tyr Val
565                 570                 575                 580

GTG TAC ACA AGA GAG CTG GAT GGC ATC GAC AGA ATC TTT ATC GTG GTT      1832
Val Tyr Thr Arg Glu Leu Asp Gly Ile Asp Arg Ile Phe Ile Val Val
            585                 590                 595

CTG AAT TTT GGA GAA TCA ACA CTG TTA AAT CTA CAT AAT ATG ATT TCG      1880
Leu Asn Phe Gly Glu Ser Thr Leu Leu Asn Leu His Asn Met Ile Ser
            600                 605                 610

GGC CTT CCC GCT AAA ATA AGA ATA AGG TTA AGT ACC AAT TCT GCC GAC      1928
Gly Leu Pro Ala Lys Ile Arg Ile Arg Leu Ser Thr Asn Ser Ala Asp
            615                 620                 625

AAA GGC AGT AAA GTT GAT ACA AGT GGC ATT TTT CTG GAC AAG GGA GAG      1976
Lys Gly Ser Lys Val Asp Thr Ser Gly Ile Phe Leu Asp Lys Gly Glu
630                 635                 640

GGA CTC ATC TTT GAA CAC AAC ACG AAG AAT CTC CTT CAT CGC CAA ACA      2024
Gly Leu Ile Phe Glu His Asn Thr Lys Asn Leu Leu His Arg Gln Thr
645                 650                 655                 660

GCT TTC AGA GAT AGA TGC TTT GTT TCC AAT CGA GCA TGC TAT TCC AGT      2072
Ala Phe Arg Asp Arg Cys Phe Val Ser Asn Arg Ala Cys Tyr Ser Ser
            665                 670                 675

GTA CTG AAC ATA CTG TAT ACC TCG TGT TAGGCACCTT TATGAAGAGA TGAAGAC    2126
Val Leu Asn Ile Leu Tyr Thr Ser Cys
            680                 685

ACTGGCATTT CAGTGGGATT GTAAGCATTT GTAATAGCTT CATGTACAGC ATGCTGCTTG    2186

GTGAACAATC ATTAATTCTT CGATATTTCT GTAGCTTGAA TGTAACCGCT TTAAGAAAGG    2246

TTCTCAAATG TTTTGAAAAA AATAAAATGT TTAAAAGT                            2284

(2) INFORMATION FOR SEQ ID NO: 181:

(i) SEQUENCE CHARACTERISTICS:
        (A) LENGTH: 685 amino acids
        (B) TYPE: amino acid
        (C) STRANDEDNESS: <Unknown>
        (D) TOPOLOGY: unknown
```

(ii) MOLECULE TYPE: protein (xi) SEQUENCE DESCRIPTION: SEQ ID NO: 181:

```
Met Ala Glu Asp Lys Ser Lys Arg Asp Ser Ile Glu Met Ser Met Lys
 1               5                  10                  15

Gly Cys Gln Thr Asn Asn Gly Phe Val His Asn Glu Asp Ile Leu Glu
                20                  25                  30

Gln Thr Pro Asp Pro Gly Ser Ser Thr Asp Asn Leu Lys His Ser Thr
            35                  40                  45

Arg Gly Ile Leu Gly Ser Gln Glu Pro Asp Phe Lys Gly Val Gln Pro
        50                  55                  60

Tyr Ala Gly Met Pro Lys Glu Val Leu Phe Gln Phe Ser Gly Gln Ala
 65                  70                  75                  80

Arg Tyr Arg Ile Pro Arg Glu Ile Leu Phe Trp Leu Thr Val Ala Ser
                85                  90                  95

Val Leu Val Leu Ile Ala Ala Thr Ile Ala Ile Ile Ala Leu Ser Pro
                100                 105                 110

Lys Cys Leu Asp Trp Trp Gln Glu Gly Pro Met Tyr Gln Ile Tyr Pro
                115                 120                 125

Arg Ser Phe Lys Asp Ser Asn Lys Asp Gly Asn Gly Asp Leu Lys Gly
            130                 135                 140

Ile Gln Asp Lys Leu Asp Tyr Ile Thr Ala Leu Asn Ile Lys Thr Val
145                 150                 155                 160

Trp Ile Thr Ser Phe Tyr Lys Ser Ser Leu Lys Asp Phe Arg Tyr Gly
                165                 170                 175

Val Glu Asp Phe Arg Glu Val Asp Pro Ile Phe Gly Thr Met Glu Asp
                180                 185                 190

Phe Glu Asn Leu Val Ala Ala Ile His Asp Lys Gly Leu Lys Leu Ile
            195                 200                 205

Ile Asp Phe Ile Pro Asn His Thr Ser Asp Lys His Ile Trp Phe Gln
210                 215                 220

Leu Ser Arg Thr Arg Thr Gly Lys Tyr Thr Asp Tyr Tyr Ile Trp His
225                 230                 235                 240

Asp Cys Thr His Glu Asn Gly Lys Thr Ile Pro Pro Asn Asn Trp Leu
                245                 250                 255

Ser Val Tyr Gly Asn Ser Ser Trp His Phe Asp Glu Val Arg Asn Gln
                260                 265                 270

Cys Tyr Phe His Gln Phe Met Lys Glu Gln Pro Asp Leu Asn Phe Arg
            275                 280                 285

Asn Pro Asp Val Gln Glu Glu Ile Lys Glu Ile Leu Arg Phe Trp Leu
290                 295                 300

Thr Lys Gly Val Asp Gly Phe Ser Leu Asp Ala Val Lys Phe Leu Leu
305                 310                 315                 320

Glu Ala Lys His Leu Arg Asp Glu Ile Gln Val Asn Lys Thr Gln Ile
                325                 330                 335

Pro Asp Thr Val Thr Gln Tyr Ser Glu Leu Tyr His Asp Phe Thr Thr
            340                 345                 350

Thr Gln Val Gly Met His Asp Ile Val Arg Ser Phe Arg Gln Thr Met
            355                 360                 365

Asp Gln Tyr Ser Thr Glu Pro Gly Arg Tyr Arg Phe Met Gly Thr Glu
370                 375                 380

Ala Tyr Ala Glu Ser Ile Asp Arg Thr Val Met Tyr Tyr Gly Leu Pro
385                 390                 395                 400
```

```
Phe Ile Gln Glu Ala Asp Phe Pro Phe Asn Asn Tyr Leu Ser Met Leu
                405                 410                 415

Asp Thr Val Ser Gly Asn Ser Val Tyr Glu Val Ile Thr Ser Trp Met
                420                 425                 430

Glu Asn Met Pro Glu Gly Lys Trp Pro Asn Trp Met Ile Gly Gly Pro
                435                 440                 445

Asp Ser Ser Arg Leu Thr Ser Arg Leu Gly Asn Gln Tyr Val Asn Val
450                 455                 460

Met Asn Met Leu Leu Phe Thr Leu Pro Gly Thr Pro Ile Thr Tyr Tyr
465                 470                 475                 480

Gly Glu Glu Ile Gly Met Gly Asn Ile Val Ala Ala Asn Leu Asn Glu
                485                 490                 495

Ser Tyr Asp Ile Asn Thr Leu Arg Ser Lys Ser Pro Met Gln Trp Asp
                500                 505                 510

Asn Ser Ser Asn Ala Gly Phe Ser Glu Ala Ser Asn Thr Trp Leu Pro
                515                 520                 525

Thr Asn Ser Asp Tyr His Thr Val Asn Val Asp Val Gln Lys Thr Gln
530                 535                 540

Pro Arg Ser Ala Leu Lys Leu Tyr Gln Asp Leu Ser Leu Leu His Ala
545                 550                 555                 560

Asn Glu Leu Leu Leu Asn Arg Gly Trp Phe Cys His Leu Arg Asn Asp
                565                 570                 575

Ser His Tyr Val Val Tyr Thr Arg Glu Leu Asp Gly Ile Asp Arg Ile
                580                 585                 590

Phe Ile Val Val Leu Asn Phe Gly Glu Ser Thr Leu Leu Asn Leu His
                595                 600                 605

Asn Met Ile Ser Gly Leu Pro Ala Lys Ile Arg Ile Arg Leu Ser Thr
                610                 615                 620

Asn Ser Ala Asp Lys Gly Ser Lys Val Asp Thr Ser Gly Ile Phe Leu
625                 630                 635                 640

Asp Lys Gly Glu Gly Leu Ile Phe Glu His Asn Thr Lys Asn Leu Leu
                645                 650                 655

His Arg Gln Thr Ala Phe Arg Asp Arg Cys Phe Val Ser Asn Arg Ala
                660                 665                 670

Cys Tyr Ser Ser Val Leu Asn Ile Leu Tyr Thr Ser Cys
                675                 680                 685

(2) INFORMATION FOR SEQ ID NO: 182:

(i) SEQUENCE CHARACTERISTICS:
        (A) LENGTH: 54 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 182:

Leu Val Pro Arg Gly Ser Pro Gly Ile Pro Gly Ser Arg Val Gly Gln
1                 5                  10                  15

Cys Thr Asp Ser Asp Val Arg Arg Pro Trp Ala Arg Ser Cys Ala His
                20                  25                  30

Gln Gly Cys Gly Ala Gly Thr Arg Asn Ser His Gly Cys Ile Thr Arg
                35                  40                  45

Pro Leu Arg Gln Ala Ser
50
```

(2) INFORMATION FOR SEQ ID NO: 183:

(i) SEQUENCE CHARACTERISTICS:
        (A) LENGTH: 19 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 183:

```
Ser Ala Arg Asp Ser Gly Pro Ala Glu Asp Gly Ser Arg Ala Val Arg
1               5                   10                  15

Leu Asn Gly
```

(2) INFORMATION FOR SEQ ID NO: 184:

(i) SEQUENCE CHARACTERISTICS:
        (A) LENGTH: 21 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 184:

```
Asp Gly Ser Arg Ala Val Arg Leu Asn Gly Val Glu Asn Ala Asn Thr
1               5                   10                  15

Arg Lys Ser Ser Arg
            20
```

(2) INFORMATION FOR SEQ ID NO: 185:

(i) SEQUENCE CHARACTERISTICS:
        (A) LENGTH: 19 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 185:

```
Glu Asn Ala Asn Thr Arg Lys Ser Ser Arg Ser Asn Pro Arg Gly Arg
1               5                   10                  15

Arg His Pro
```

(2) INFORMATION FOR SEQ ID NO: 186:

(i) SEQUENCE CHARACTERISTICS:
        (A) LENGTH: 11 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 186:

```
Thr Arg Lys Ser Ser Arg Ser Asn Pro Arg Gly
1               5                   10
```

(2) INFORMATION FOR SEQ ID NO: 187:

(i) SEQUENCE CHARACTERISTICS:
        (A) LENGTH: 21 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 187:

Ser Arg Pro Tyr Ser Val Asp Ser Asp Ser Asp Thr Asn Ala Lys His
1               5                   10                  15

Ser Ser His Asn Arg
            20

(2) INFORMATION FOR SEQ ID NO: 188:

(i) SEQUENCE CHARACTERISTICS:
          (A) LENGTH: 19 amino acids
          (B) TYPE: amino acid
          (C) STRANDEDNESS: <Unknown>
          (D) TOPOLOGY: unknown (ii) MOLECULE TYPE: peptide (xi) SEQUENCE DESCRIPTION: SEQ ID NO: 188:

Thr Asn Ala Lys His Ser Ser His Asn Arg Arg Leu Arg Thr Arg Ser
1               5                   10                  15

Arg Pro Asn (2) INFORMATION FOR SEQ ID NO: 189:

(i) SEQUENCE CHARACTERISTICS:
          (A) LENGTH: 24 amino acids
          (B) TYPE: amino acid
          (C) STRANDEDNESS: <Unknown>
          (D) TOPOLOGY: unknown (ii) MOLECULE TYPE: peptide (xi) SEQUENCE DESCRIPTION: SEQ ID NO: 189:

Arg Tyr Lys His Asp Ile Gly Cys Asp Ala Gly Val Asp Lys Lys Ser
1               5                   10                  15

Ser Ser Val Arg Gly Gly Cys Gly
            20

(2) INFORMATION FOR SEQ ID NO: 190:

(i) SEQUENCE CHARACTERISTICS:
          (A) LENGTH: 26 amino acids
          (B) TYPE: amino acid
          (C) STRANDEDNESS: <Unknown>
          (D) TOPOLOGY: linear (ii) MOLECULE TYPE: peptide (xi) SEQUENCE DESCRIPTION: SEQ ID NO: 190:

Gly Cys Asp Ala Gly Val Asp Lys Lys Ser Ser Ser Val Arg Gly Gly
1               5                   10                  15

Cys Gly Ala His Ser Ser Pro Pro Arg Ala
            20                  25

(2) INFORMATION FOR SEQ ID NO: 191:

(i) SEQUENCE CHARACTERISTICS:
          (A) LENGTH: 21 amino acids
          (B) TYPE: amino acid
          (C) STRANDEDNESS: <Unknown>
          (D) TOPOLOGY: unknown (ii) MOLECULE TYPE: peptide (xi) SEQUENCE DESCRIPTION: SEQ ID NO: 191:

Gly Ala His Ser Ser Pro Pro Arg Ala Gly Arg Gly Pro Arg Gly Thr
 1               5                  10                  15

Met Val Ser Arg Leu
            20

(2) INFORMATION FOR SEQ ID NO: 192:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 192:

Glu Asn Ala Asn Thr Arg Lys Ser Ser Arg
 1               5                  10

(2) INFORMATION FOR SEQ ID NO: 193:

(i) SEQUENCE CHARACTERISTICS:
        (A) LENGTH: 39 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 193:

Lys Lys Arg Ile Ala Gly Leu Pro Trp Tyr Arg Cys Arg Thr Val Ala
 1               5                  10                  15

Phe Glu Thr Gly Met Gln Asn Thr Gln Leu Cys Ser Thr Ile Val Gln
            20                  25                  30

Leu Ser Phe Thr Pro Glu Glu
            35

(2) INFORMATION FOR SEQ ID NO: 194:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 194:

Arg Lys Ser Ser Arg Ser Asn Pro Arg Gly
 1               5                  10

(2) INFORMATION FOR SEQ ID NO: 195:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 195:

Ser Asn Pro Arg Gly Arg Arg His Pro
1               5

(2) INFORMATION FOR SEQ ID NO: 196:

(i) SEQUENCE CHARACTERISTICS:
            (A) LENGTH: 9 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 196:

Thr Asn Ala Lys His Ser Ser His Asn
1               5

(2) INFORMATION FOR SEQ ID NO: 197:

(i) SEQUENCE CHARACTERISTICS:
            (A) LENGTH: 10 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 197:

Ser Ser His Asn Arg Arg Leu Arg Thr Arg
1               5                   10

(2) INFORMATION FOR SEQ ID NO: 198:

(i) SEQUENCE CHARACTERISTICS:
            (A) LENGTH: 10 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 198:

Arg Arg Leu Arg Thr Arg Ser Arg Pro Asn
1               5                   10

(2) INFORMATION FOR SEQ ID NO: 199:

(i) SEQUENCE CHARACTERISTICS:
            (A) LENGTH: 19 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 199:

Arg Val Gly Gln Cys Thr Asp Ser Asp Val Arg Arg Pro Trp Ala Arg
1               5                   10                  15

Ser Cys Ala (2) INFORMATION FOR SEQ ID NO: 200:

(i) SEQUENCE CHARACTERISTICS:
            (A) LENGTH: 21 amino acids
            (B) TYPE: amino acid

```
            (C) STRANDEDNESS: <Unknown>
            (D) TOPOLOGY: unknown (ii) MOLECULE TYPE: peptide (xi) SEQUENCE DESCRIPTION: SEQ ID NO: 200:

Val Arg Arg Pro Trp Ala Arg Ser Cys Ala His Gln Gly Cys Gly Ala
1               5                   10                  15

Gly Thr Arg Asn Ser
            20

(2) INFORMATION FOR SEQ ID NO: 201:

(i) SEQUENCE CHARACTERISTICS:
            (A) LENGTH: 19 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 201:

Gly Thr Arg Asn Ser His Gly Cys Ile Thr Arg Pro Leu Arg Gln Ala
1               5                   10                  15

Ser Gln His (2) INFORMATION FOR SEQ ID NO: 202:

(i) SEQUENCE CHARACTERISTICS:
            (A) LENGTH: 40 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 202:

Ser Thr Pro Pro Ser Arg Glu Ala Tyr Ser Arg Pro Tyr Ser Val Asp
1               5                   10                  15

Ser Asp Ser Asp Thr Met Ala Lys His Ser Ser His Asn Arg Arg Leu
            20                  25                  30

Arg Thr Arg Ser Arg Pro Asn Gly
            35                  40

(2) INFORMATION FOR SEQ ID NO: 203:

(i) SEQUENCE CHARACTERISTICS:
            (A) LENGTH: 4 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 203:

Tyr Ser Lys Val
1

(2) INFORMATION FOR SEQ ID NO: 204:

(i) SEQUENCE CHARACTERISTICS:
            (A) LENGTH: 4 amino acids
            (B) TYPE: amino acid
            (C) STRANDEDNESS: <Unknown>
            (D) TOPOLOGY: unknown
```

```
        (ii) MOLECULE TYPE: peptide (xi) SEQUENCE DESCRIPTION: SEQ ID NO: 204:

Phe Pro His Leu
  1

(2) INFORMATION FOR SEQ ID NO: 205:

(i) SEQUENCE CHARACTERISTICS:
             (A) LENGTH: 4 amino acids
             (B) TYPE: amino acid
             (C) STRANDEDNESS: <Unknown>
             (D) TOPOLOGY: unknown (ii) MOLECULE TYPE: peptide (xi) SEQUENCE DESCRIPTION: SEQ ID NO: 205:

Tyr Arg Gly Val
  1

(2) INFORMATION FOR SEQ ID NO: 206:

(i) SEQUENCE CHARACTERISTICS:
             (A) LENGTH: 4 amino acids
             (B) TYPE: amino acid
             (C) STRANDEDNESS: <Unknown>
             (D) TOPOLOGY: unknown (ii) MOLECULE TYPE: peptide (xi) SEQUENCE DESCRIPTION: SEQ ID NO: 206:

Tyr Gln Thr Ile
  1

(2) INFORMATION FOR SEQ ID NO: 207:

(i) SEQUENCE CHARACTERISTICS:
             (A) LENGTH: 4 amino acids
             (B) TYPE: amino acid
             (C) STRANDEDNESS: <Unknown>
             (D) TOPOLOGY: unknown (ii) MOLECULE TYPE: peptide (xi) SEQUENCE DESCRIPTION: SEQ ID NO: 207:

Thr Glu Gln Phe
  1

(2) INFORMATION FOR SEQ ID NO: 208:

(i) SEQUENCE CHARACTERISTICS:
             (A) LENGTH: 4 amino acids
             (B) TYPE: amino acid
             (C) STRANDEDNESS: <Unknown>
             (D) TOPOLOGY: unknown (ii) MOLECULE TYPE: peptide (xi) SEQUENCE DESCRIPTION: SEQ ID NO: 208:

Thr Glu Val Met
  1

(2) INFORMATION FOR SEQ ID NO: 209:

(i) SEQUENCE CHARACTERISTICS:
             (A) LENGTH: 4 amino acids
             (B) TYPE: amino acid
             (C) STRANDEDNESS: <Unknown>
             (D) TOPOLOGY: unknown
```

(ii) MOLECULE TYPE: peptide (xi) SEQUENCE DESCRIPTION: SEQ ID NO: 209:

Thr Ser Ala Phe
1

(2) INFORMATION FOR SEQ ID NO: 210:

(i) SEQUENCE CHARACTERISTICS:
      (A) LENGTH: 4 amino acids
      (B) TYPE: amino acid
      (C) STRANDEDNESS: <Unknown>
      (D) TOPOLOGY: unknown (ii) MOLECULE TYPE: peptide (xi) SEQUENCE DESCRIPTION: SEQ ID NO: 210:

Tyr Thr Arg Phe
1

(2) INFORMATION FOR SEQ ID NO: 211:

(i) SEQUENCE CHARACTERISTICS:
      (A) LENGTH: 717 base pairs
      (B) TYPE: nucleic acid
      (C) STRANDEDNESS: single
      (D) TOPOLOGY: linear (ii) MOLECULE TYPE: DNA (ix) FEATURE:
      (A) NAME/KEY: Coding Sequence
      (B) LOCATION: 1...714
      (D) OTHER INFORMATION:

(xi) SEQUENCE DESCRIPTION: SEQ ID NO: 211:

```
ATG TCC CCT ATA CTA GGT TAT TGG AAA ATT AAG GGC CTT GTG CAA CCC        48
Met Ser Pro Ile Leu Gly Tyr Trp Lys Ile Lys Gly Leu Val Gln Pro
 1               5                  10                  15

ACT CGA CTT CTT TTG GAA TAT CTT GAA GAA AAA TAT GAA GAG CAT TTG        96
Thr Arg Leu Leu Leu Glu Tyr Leu Glu Glu Lys Tyr Glu Glu His Leu
                20                  25                  30

TAT GAG CGC GAT GAA GGT GAT AAA TGG CGA AAC AAA AAG TTT GAA TTG       144
Tyr Glu Arg Asp Glu Gly Asp Lys Trp Arg Asn Lys Lys Phe Glu Leu
            35                  40                  45

GGT TTG GAG TTT CCC AAT CTT CCT TAT TAT ATT GAT GGT GAT GTT AAA       192
Gly Leu Glu Phe Pro Asn Leu Pro Tyr Tyr Ile Asp Gly Asp Val Lys
        50                  55                  60

TTA ACA CAG TCT ATG GCC ATC ATA CGT TAT ATA GCT GAC AAG CAC AAC       240
Leu Thr Gln Ser Met Ala Ile Ile Arg Tyr Ile Ala Asp Lys His Asn
65                  70                  75                  80

ATG TTG GGT GGT TGT CCA AAA GAG CGT GCA GAG ATT TCA ATG CTT GAA       288
Met Leu Gly Gly Cys Pro Lys Glu Arg Ala Glu Ile Ser Met Leu Glu
                85                  90                  95

GGA GCG GTT TTG GAT ATT AGA TAC GGT GTT TCG AGA ATT GCA TAT AGT       336
Gly Ala Val Leu Asp Ile Arg Tyr Gly Val Ser Arg Ile Ala Tyr Ser
            100                 105                 110

AAA GAC TTT GAA ACT CTC AAA GTT GAT TTT CTT AGC AAG CTA CCT GAA       384
Lys Asp Phe Glu Thr Leu Lys Val Asp Phe Leu Ser Lys Leu Pro Glu
        115                 120                 125

ATG CTG AAA ATG TTC GAA GAT CGT TTA TGT CAT AAA ACA TAT TTA AAT       432
Met Leu Lys Met Phe Glu Asp Arg Leu Cys His Lys Thr Tyr Leu Asn
    130                 135                 140
```

```
GGT GAT CAT GTA ACC CAT CCT GAC TTC ATG TTG TAT GAC GCT CTT GAT       480
Gly Asp His Val Thr His Pro Asp Phe Met Leu Tyr Asp Ala Leu Asp
145                 150                 155                 160

GTT GTT TTA TAC ATG GAC CCA ATG TGC CTG GAT GCG TTC CCA AAA TTA       528
Val Val Leu Tyr Met Asp Pro Met Cys Leu Asp Ala Phe Pro Lys Leu
                165                 170                 175

GTT TGT TTT AAA AAA CGT ATT GAA GCT ATC CCA CAA ATT GAT AAG TAC       576
Val Cys Phe Lys Lys Arg Ile Glu Ala Ile Pro Gln Ile Asp Lys Tyr
            180                 185                 190

TTG AAA TCC AGC AAG TAT ATA GCA TGG CCT TTG CAG GGC TGG CAA GCC       624
Leu Lys Ser Ser Lys Tyr Ile Ala Trp Pro Leu Gln Gly Trp Gln Ala
        195                 200                 205

ACG TTT GGT GGT GGC GAC CAT CCT CCA AAA TCG GAT CTG GTT CCG CGT       672
Thr Phe Gly Gly Gly Asp His Pro Pro Lys Ser Asp Leu Val Pro Arg
    210                 215                 220

GGA TCC CCA GGA ATT CCC GGG TCG ACT CGA GCG GCC GCA TCG TGA           717
Gly Ser Pro Gly Ile Pro Gly Ser Thr Arg Ala Ala Ala Ser
225                 230                 235
```

(2) INFORMATION FOR SEQ ID NO: 212:

(i) SEQUENCE CHARACTERISTICS:
        (A) LENGTH: 238 amino acids
        (B) TYPE: amino acid
        (C) STRANDEDNESS: <Unknown>
        (D) TOPOLOGY: unknown (ii) MOLECULE TYPE: protein (xi) SEQUENCE DESCRIPTION: SEQ ID NO: 212:

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205
```

```
Thr Phe Gly Gly Gly Asp His Pro Pro Lys Ser Asp Leu Val Pro Arg
    210                 215                 220

Gly Ser Pro Gly Ile Pro Gly Ser Thr Arg Ala Ala Ala Ser
225                 230                 235
```

(2) INFORMATION FOR SEQ ID NO: 213:

(i) SEQUENCE CHARACTERISTICS:
        (A) LENGTH: 282 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 213:

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
                180                 185                 190

Leu Lys Ser Ser Lys Tyr Ile Ala Trp Pro Leu Gln Gly Trp Gln Ala
            195                 200                 205

Thr Phe Gly Gly Gly Asp His Pro Pro Lys Ser Asp Leu Val Pro Arg
    210                 215                 220

Gly Ser Pro Gly Ile Pro Gly Ser Thr Arg Ala Ala Ala Ser Ser Gln
225                 230                 235                 240

Gly Ser Lys Gln Cys Met Gln Tyr Arg Thr Gly Arg Leu Thr Val Gly
                245                 250                 255

Ser Glu Tyr Gly Cys Gly Met Asn Pro Ala Arg His Ala Thr Pro Ala
                260                 265                 270

Tyr Pro Ala Arg Leu Leu Pro Arg Tyr Arg
    275                 280
```

(2) INFORMATION FOR SEQ ID NO: 214:

(i) SEQUENCE CHARACTERISTICS:
        (A) LENGTH: 282 amino acids
        (B) TYPE: amino acid (C) STRANDEDNESS: <Unknown>
        (D) TOPOLOGY: unknown (ii) MOLECULE TYPE: peptide (xi) SEQUENCE DESCRIPTION: SEQ ID NO: 214:

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Pro Gly Ile Pro Gly Ser Thr Arg Ala Ala Ala Ser Ser Asp
225                 230                 235                 240

His Ala Leu Gly Thr Asn Leu Arg Ser Asp Asn Ala Lys Glu Pro Gly
                245                 250                 255

Asp Tyr Asn Cys Cys Gly Asn Gly Asn Ser Thr Gly Arg Lys Val Phe
            260                 265                 270

Asn Arg Arg Arg Pro Ser Ala Ile Pro Thr
        275                 280

(2) INFORMATION FOR SEQ ID NO: 215:

(i) SEQUENCE CHARACTERISTICS:
        (A) LENGTH: 279 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 215:

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

```
Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
 50                  55                  60

Leu Thr Gln Ser Met Ala Ile Ile Arg Tyr Ile Ala Asp Lys His Asn
 65                  70                  75                  80

Met Leu Gly Gly Cys Pro Lys Glu Arg Ala Glu Ile Ser Met Leu Glu
                 85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
            195                 200                 205

Thr Phe Gly Gly Gly Asp His Pro Pro Lys Ser Asp Leu Val Pro Arg
    210                 215                 220

Gly Ser Pro Gly Ile Pro Gly Ser Thr Arg Ala Ala Ser Ser Pro
225                 230                 235                 240

Cys Gly Gly Ser Trp Gly Arg Phe Met Gln Gly Gly Leu Phe Gly Gly
                245                 250                 255

Arg Thr Asp Gly Cys Gly Ala His Arg Asn Arg Thr Ser Ala Ser Leu
            260                 265                 270

Glu Pro Pro Ser Ser Asp Tyr
            275
```

(2) INFORMATION FOR SEQ ID NO: 216:

(i) SEQUENCE CHARACTERISTICS:
      (A) LENGTH: 277 amino acids
      (B) TYPE: amino acid
      (C) STRANDEDNESS: <Unknown>
      (D) TOPOLOGY: unknown (ii) MOLECULE TYPE: peptide (xi) SEQUENCE DESCRIPTION: SEQ ID NO: 216:

```
Met Ser Pro Ile Leu Gly Tyr Trp Lys Ile Lys Gly Leu Val Gln Pro
 1               5                  10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
 50                  55                  60

Leu Thr Gln Ser Met Ala Ile Ile Arg Tyr Ile Ala Asp Lys His Asn
 65                  70                  75                  80

Met Leu Gly Gly Cys Pro Lys Glu Arg Ala Glu Ile Ser Met Leu Glu
                 85                  90                  95
```

-continued

```
Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
            130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
                180                 185                 190

Leu Lys Ser Ser Lys Tyr Ile Ala Trp Pro Leu Gln Gly Trp Gln Ala
            195                 200                 205

Thr Phe Gly Gly Gly Asp His Pro Pro Lys Ser Asp Leu Val Pro Arg
    210                 215                 220

Gly Ser Pro Gly Ile Pro Gly Ser Thr Arg Ala Ala Ser Arg Gly
225                 230                 235                 240

Ser Thr Gly Thr Ala Gly Gly Glu Arg Ser Gly Val Leu Asn Leu His
                245                 250                 255

Thr Arg Asp Asn Ala Ser Gly Ser Gly Phe Lys Pro Trp Tyr Pro Ser
                260                 265                 270

Asn Arg Gly His Lys
            275
```

(2) INFORMATION FOR SEQ ID NO: 217:

(i) SEQUENCE CHARACTERISTICS:
        (A) LENGTH: 277 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 217:

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
            35                  40                  45

Gly Leu Glu Phe Pro Asn Leu Pro Tyr Tyr Ile Asp Gly Asp Val Lys
50                  55                  60

Leu Thr Gln Ser Met Ala Ile Ile Arg Tyr Ile Ala Asp Lys His Asn
65              70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
            130                 135                 140

Gly Asp His Val Thr His Pro Asp Phe Met Leu Tyr Asp Ala Leu Asp
145                 150                 155                 160
```

```
Val Val Leu Tyr Met Asp Pro Met Cys Leu Asp Ala Phe Pro Lys Leu
            165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
            195                 200                 205

Thr Phe Gly Gly Gly Asp His Pro Pro Lys Ser Asp Leu Val Pro Arg
    210                 215                 220

Gly Ser Pro Gly Ile Pro Gly Ser Thr Arg Ala Ala Ala Ser Ser His
225                 230                 235                 240

Ser Gly Gly Met Asn Arg Ala Tyr Gly Asp Val Phe Arg Glu Leu Arg
                245                 250                 255

Asp Arg Trp Asn Ala Thr Ser His His Thr Arg Pro Thr Pro Gln Leu
            260                 265                 270

Pro Arg Gly Pro Asn
        275

(2) INFORMATION FOR SEQ ID NO: 218:

(i) SEQUENCE CHARACTERISTICS:
        (A) LENGTH: 248 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 218:

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
            165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
            195                 200                 205

Thr Phe Gly Gly Gly Asp His Pro Pro Lys Ser Asp Leu Val Pro Arg
    210                 215                 220
```

```
Gly Ser Pro Gly Ile Pro Gly Ser Thr Arg Ala Ala Ala Ser Ser His
225                 230                 235                 240

Ser Gly Gly Met Asn Arg Ala Tyr
                245
```

(2) INFORMATION FOR SEQ ID NO: 219:

(i) SEQUENCE CHARACTERISTICS:
        (A) LENGTH: 248 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 219:

```
Met Ser Pro Ile Leu Gly Tyr Trp Lys Ile Lys Gly Leu Val Gln Pro
1                   5                   10                  15

Thr Arg Leu Leu Leu Glu Tyr Leu Glu Glu Lys Tyr Glu Glu His Leu
                20                  25                  30

Tyr Glu Arg Asp Glu Gly Asp Lys Trp Arg Asn Lys Lys Phe Glu Leu
                35                  40                  45

Gly Leu Glu Phe Pro Asn Leu Pro Tyr Tyr Ile Asp Gly Asp Val Lys
            50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
                115                 120                 125

Met Leu Lys Met Phe Glu Asp Arg Leu Cys His Lys Thr Tyr Leu Asn
                130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
                180                 185                 190

Leu Lys Ser Ser Lys Tyr Ile Ala Trp Pro Leu Gln Gly Trp Gln Ala
                195                 200                 205

Thr Phe Gly Gly Gly Asp His Pro Pro Lys Ser Asp Leu Val Pro Arg
                210                 215                 220

Gly Ser Pro Gly Ile Pro Gly Ser Thr Arg Ala Ala Ala Ser Gly Asp
225                 230                 235                 240

Val Phe Arg Glu Leu Arg Asp Arg
                245
```

(2) INFORMATION FOR SEQ ID NO: 220:

(i) SEQUENCE CHARACTERISTICS:
        (A) LENGTH: 248 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 220:

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
                20                  25                  30

Tyr Glu Arg Asp Glu Gly Asp Lys Trp Arg Asn Lys Lys Phe Glu Leu
            35                  40                  45

Gly Leu Glu Phe Pro Asn Leu Pro Tyr Tyr Ile Asp Gly Asp Val Lys
        50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Asp His Pro Pro Lys Ser Asp Leu Val Pro Arg
    210                 215                 220

Gly Ser Pro Gly Ile Pro Gly Ser Thr Arg Ala Ala Ala Ser Trp Asn
225                 230                 235                 240

Ala Thr Ser His His Thr Arg Pro
                245

(2) INFORMATION FOR SEQ ID NO: 221:

(i) SEQUENCE CHARACTERISTICS:
        (A) LENGTH: 247 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 221:

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
                20                  25                  30

Tyr Glu Arg Asp Glu Gly Asp Lys Trp Arg Asn Lys Lys Phe Glu Leu
            35                  40                  45

Gly Leu Glu Phe Pro Asn Leu Pro Tyr Tyr Ile Asp Gly Asp Val Lys
        50                  55                  60

Leu Thr Gln Ser Met Ala Ile Ile Arg Tyr Ile Ala Asp Lys His Asn
65                  70                  75                  80

```
Met Leu Gly Gly Cys Pro Lys Glu Arg Ala Glu Ile Ser Met Leu Glu
                85                  90                  95
Gly Ala Val Leu Asp Ile Arg Tyr Gly Val Ser Arg Ile Ala Tyr Ser
                100                 105                 110
Lys Asp Phe Glu Thr Leu Lys Val Asp Phe Leu Ser Lys Leu Pro Glu
                115                 120                 125
Met Leu Lys Met Phe Glu Asp Arg Leu Cys His Lys Thr Tyr Leu Asn
            130                 135                 140
Gly Asp His Val Thr His Pro Asp Phe Met Leu Tyr Asp Ala Leu Asp
145                 150                 155                 160
Val Val Leu Tyr Met Asp Pro Met Cys Leu Asp Ala Phe Pro Lys Leu
                165                 170                 175
Val Cys Phe Lys Lys Arg Ile Glu Ala Ile Pro Gln Ile Asp Lys Tyr
                180                 185                 190
Leu Lys Ser Ser Lys Tyr Ile Ala Trp Pro Leu Gln Gly Trp Gln Ala
                195                 200                 205
Thr Phe Gly Gly Gly Asp His Pro Pro Lys Ser Asp Leu Val Pro Arg
            210                 215                 220
Gly Ser Pro Gly Ile Pro Gly Ser Thr Arg Ala Ala Ser Thr Pro
225                 230                 235                 240
Gln Leu Pro Arg Gly Pro Asn
                245

(2) INFORMATION FOR SEQ ID NO: 222:

(i) SEQUENCE CHARACTERISTICS:
        (A) LENGTH: 258 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 222:

Met Ser Pro Ile Leu Gly Tyr Trp Lys Ile Lys Gly Leu Val Gln Pro
1               5                   10                  15
Thr Arg Leu Leu Leu Glu Tyr Leu Glu Glu Lys Tyr Glu Glu His Leu
                20                  25                  30
Tyr Glu Arg Asp Glu Gly Asp Lys Trp Arg Asn Lys Lys Phe Glu Leu
            35                  40                  45
Gly Leu Glu Phe Pro Asn Leu Pro Tyr Tyr Ile Asp Gly Asp Val Lys
        50                  55                  60
Leu Thr Gln Ser Met Ala Ile Ile Arg Tyr Ile Ala Asp Lys His Asn
65                  70                  75                  80
Met Leu Gly Gly Cys Pro Lys Glu Arg Ala Glu Ile Ser Met Leu Glu
                85                  90                  95
Gly Ala Val Leu Asp Ile Arg Tyr Gly Val Ser Arg Ile Ala Tyr Ser
                100                 105                 110
Lys Asp Phe Glu Thr Leu Lys Val Asp Phe Leu Ser Lys Leu Pro Glu
                115                 120                 125
Met Leu Lys Met Phe Glu Asp Arg Leu Cys His Lys Thr Tyr Leu Asn
            130                 135                 140
Gly Asp His Val Thr His Pro Asp Phe Met Leu Tyr Asp Ala Leu Asp
145                 150                 155                 160
Val Val Leu Tyr Met Asp Pro Met Cys Leu Asp Ala Phe Pro Lys Leu
                165                 170                 175
```

```
Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
            195                 200                 205

Thr Phe Gly Gly Gly Asp His Pro Pro Lys Ser Asp Leu Val Pro Arg
    210                 215                 220

Gly Ser Pro Gly Ile Pro Gly Ser Thr Arg Ala Ala Ala Ser Gly Asp
225                 230                 235                 240

Val Phe Arg Glu Leu Arg Asp Arg Trp Asn Ala Thr Ser His His Thr
                245                 250                 255

Arg Pro (2) INFORMATION FOR SEQ ID NO: 223:

(i) SEQUENCE CHARACTERISTICS:
        (A) LENGTH: 257 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 223:

Met Ser Pro Ile Leu Gly Tyr Trp Lys Ile Lys Gly Leu Val Gln Pro
1                   5                   10                  15

Thr Arg Leu Leu Leu Glu Tyr Leu Glu Glu Lys Tyr Glu Glu His Leu
                20                  25                  30

Tyr Glu Arg Asp Glu Gly Asp Lys Trp Arg Asn Lys Lys Phe Glu Leu
                35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
                115                 120                 125

Met Leu Lys Met Phe Glu Asp Arg Leu Cys His Lys Thr Tyr Leu Asn
130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
            195                 200                 205

Thr Phe Gly Gly Gly Asp His Pro Pro Lys Ser Asp Leu Val Pro Arg
    210                 215                 220

Gly Ser Pro Gly Ile Pro Gly Ser Thr Arg Ala Ala Ala Ser Trp Asn
225                 230                 235                 240

Ala Thr Ser His His Thr Arg Pro Thr Pro Gln Leu Pro Arg Gly Pro
                245                 250                 255

Asn
```

(2) INFORMATION FOR SEQ ID NO: 224:

(i) SEQUENCE CHARACTERISTICS:
        (A) LENGTH: 267 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 224:

```
Met Ser Pro Ile Leu Gly Tyr Trp Lys Ile Lys Gly Leu Val Gln Pro
 1               5                  10                  15

Thr Arg Leu Leu Leu Glu Tyr Leu Glu Glu Lys Tyr Glu Glu His Leu
                20                  25                  30

Tyr Glu Arg Asp Glu Gly Asp Lys Trp Arg Asn Lys Lys Phe Glu Leu
            35                  40                  45

Gly Leu Glu Phe Pro Asn Leu Pro Tyr Tyr Ile Asp Gly Asp Val Lys
        50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Asp His Pro Pro Lys Ser Asp Leu Val Pro Arg
210                 215                 220

Gly Ser Pro Gly Ile Pro Gly Ser Thr Arg Ala Ala Ala Ser Gly Asp
225                 230                 235                 240

Val Phe Arg Glu Leu Arg Asp Arg Trp Asn Ala Thr Ser His His Thr
                245                 250                 255

Arg Pro Thr Pro Gln Leu Pro Arg Gly Pro Asn
            260                 265
```

(2) INFORMATION FOR SEQ ID NO: 225:

(i) SEQUENCE CHARACTERISTICS:
        (A) LENGTH: 277 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 225:

```
Met Ser Pro Ile Leu Gly Tyr Trp Lys Ile Lys Gly Leu Val Gln Pro
 1               5                  10                  15
```

```
Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
            35                  40                  45

Gly Leu Glu Phe Pro Asn Leu Pro Tyr Tyr Ile Asp Gly Asp Val Lys
 50                  55                  60

Leu Thr Gln Ser Met Ala Ile Ile Arg Tyr Ile Ala Asp Lys His Asn
 65                  70                  75                  80

Met Leu Gly Gly Cys Pro Lys Glu Arg Ala Glu Ile Ser Met Leu Glu
                 85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
 130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
            195                 200                 205

Thr Phe Gly Gly Gly Asp His Pro Pro Lys Ser Asp Leu Val Pro Arg
 210                 215                 220

Gly Ser Pro Gly Ile Pro Gly Ser Thr Arg Ala Ala Ser Ser His
225                 230                 235                 240

Ser Gly Gly Met Asn Arg Ala Tyr Gly Asp Val Phe Arg Glu Leu Arg
                245                 250                 255

Asp Arg Trp Asn Ala Thr Ser Ala Ala Thr Arg Pro Thr Pro Gln Leu
            260                 265                 270

Pro Arg Gly Pro Asn
            275
```

(2) INFORMATION FOR SEQ ID NO: 226:

(i) SEQUENCE CHARACTERISTICS:
        (A) LENGTH: 277 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 226:

```
Met Ser Pro Ile Leu Gly Tyr Trp Lys Ile Lys Gly Leu Val Gln Pro
 1                   5                  10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
            35                  40                  45

Gly Leu Glu Phe Pro Asn Leu Pro Tyr Tyr Ile Asp Gly Asp Val Lys
 50                  55                  60

Leu Thr Gln Ser Met Ala Ile Ile Arg Tyr Ile Ala Asp Lys His Asn
 65                  70                  75                  80
```

```
Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Pro Gly Ile Pro Gly Ser Thr Arg Ala Ala Ser Ser Ala
225                 230                 235                 240

Arg Asp Ser Gly Pro Ala Glu Asp Gly Ser Arg Ala Val Arg Leu Asn
                245                 250                 255

Gly Val Glu Asn Ala Asn Thr Arg Lys Ser Ser Arg Ser Asn Pro Arg
            260                 265                 270

Gly Arg Arg His Pro
        275

(2) INFORMATION FOR SEQ ID NO: 227:

(i) SEQUENCE CHARACTERISTICS:
        (A) LENGTH: 257 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 227:

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140
```

```
Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Pro Gly Ile Pro Gly Ser Thr Arg Ala Ala Ser Ser Ala
225             230                 235                 240

Arg Asp Ser Gly Pro Ala Glu Asp Gly Ser Arg Ala Val Arg Leu Asn
                245                 250                 255

Gly
```

(2) INFORMATION FOR SEQ ID NO: 228:

(i) SEQUENCE CHARACTERISTICS:
        (A) LENGTH: 259 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 228:

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
        130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220
```

-continued

```
Gly Ser Pro Gly Ile Pro Gly Ser Thr Arg Ala Ala Ala Ser Asp Gly
225                 230                 235                 240

Ser Arg Ala Val Arg Leu Asn Gly Val Glu Asn Ala Asn Thr Arg Lys
                245                 250                 255

Ser Ser Arg
```

(2) INFORMATION FOR SEQ ID NO: 229:

(i) SEQUENCE CHARACTERISTICS:
        (A) LENGTH: 257 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 229:

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
                20                  25                  30

Tyr Glu Arg Asp Glu Gly Asp Lys Trp Arg Asn Lys Lys Phe Glu Leu
            35                  40                  45

Gly Leu Glu Phe Pro Asn Leu Pro Tyr Tyr Ile Asp Gly Asp Val Lys
50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
                180                 185                 190

Leu Lys Ser Ser Lys Tyr Ile Ala Trp Pro Leu Gln Gly Trp Gln Ala
            195                 200                 205

Thr Phe Gly Gly Asp His Pro Pro Lys Ser Asp Leu Val Pro Arg
        210                 215                 220

Gly Ser Pro Gly Ile Pro Gly Ser Thr Arg Ala Ala Ala Ser Glu Asn
225                 230                 235                 240

Ala Asn Thr Arg Lys Ser Ser Arg Ser Asn Pro Arg Gly Arg Arg His
                245                 250                 255

Pro
```

(2) INFORMATION FOR SEQ ID NO: 230:

(i) SEQUENCE CHARACTERISTICS:
        (A) LENGTH: 248 amino acids
        (B) TYPE: amino acid
        (C) STRANDEDNESS: <Unknown>
        (D) TOPOLOGY: unknown -continued (ii) MOLECULE TYPE: peptide (xi) SEQUENCE DESCRIPTION: SEQ ID NO: 230:

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
            85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Asp His Pro Pro Lys Ser Asp Leu Val Pro Arg
    210                 215                 220

Gly Ser Pro Gly Ile Pro Gly Ser Thr Arg Ala Ala Ala Ser Glu Asn
225                 230                 235                 240

Ala Asn Thr Arg Lys Ser Ser Arg
                245
```

(2) INFORMATION FOR SEQ ID NO: 231:

(i) SEQUENCE CHARACTERISTICS:
    (A) LENGTH: 248 amino acids
    (B) TYPE: amino acid
    (C) STRANDEDNESS: <Unknown>
    (D) TOPOLOGY: unknown (ii) MOLECULE TYPE: peptide (xi) SEQUENCE DESCRIPTION: SEQ ID NO: 231:

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80
```

```
Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
            130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
            195                 200                 205

Thr Phe Gly Gly Asp His Pro Pro Lys Ser Asp Leu Val Pro Arg
            210                 215                 220

Gly Ser Pro Gly Ile Pro Gly Ser Thr Arg Ala Ala Ser Arg Lys
225                 230                 235                 240

Ser Ser Arg Ser Asn Pro Arg Gly
                245
```

(2) INFORMATION FOR SEQ ID NO: 232:

(i) SEQUENCE CHARACTERISTICS:
        (A) LENGTH: 247 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 232:

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
            35                  40                  45

Gly Leu Glu Phe Pro Asn Leu Pro Tyr Tyr Ile Asp Gly Asp Val Lys
        50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
            130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175
```

-continued

```
Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Pro Gly Ile Pro Gly Ser Thr Arg Ala Ala Ala Ser Ser Asn
225                 230                 235                 240

Pro Arg Gly Arg Arg His Pro
                245
```

(2) INFORMATION FOR SEQ ID NO: 233:

(i) SEQUENCE CHARACTERISTICS:
        (A) LENGTH: 249 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 233:

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Pro Gly Ile Pro Gly Ser Thr Arg Ala Ala Ala Ser Thr Arg
225                 230                 235                 240

Lys Ser Ser Arg Ser Asn Pro Arg Gly
                245
```

(2) INFORMATION FOR SEQ ID NO: 234:

(i) SEQUENCE CHARACTERISTICS:
        (A) LENGTH: 277 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 234:

```
Met Ser Pro Ile Leu Gly Tyr Trp Lys Ile Lys Gly Leu Val Gln Pro
 1               5                  10                  15

Thr Arg Leu Leu Leu Glu Tyr Leu Glu Glu Lys Tyr Glu Glu His Leu
             20                  25                  30

Tyr Glu Arg Asp Glu Gly Asp Lys Trp Arg Asn Lys Lys Phe Glu Leu
         35                  40                  45

Gly Leu Glu Phe Pro Asn Leu Pro Tyr Tyr Ile Asp Gly Asp Val Lys
     50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                 85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Pro Gly Ile Pro Gly Ser Thr Arg Ala Ala Ala Ser Ser Thr
225                 230                 235                 240

Pro Pro Ser Arg Glu Ala Tyr Ser Arg Pro Tyr Ser Val Asp Ser Asp
                245                 250                 255

Ser Asp Thr Asn Ala Lys His Ser Ser His Asn Arg Arg Leu Arg Thr
            260                 265                 270

Arg Ser Arg Pro Asn
        275
```

(2) INFORMATION FOR SEQ ID NO: 235:

(i) SEQUENCE CHARACTERISTICS:
        (A) LENGTH: 258 amino acids
        (B) TYPE: amino acid
        (C) STRANDEDNESS: <Unknown>
        (D) TOPOLOGY: unknown

```
        (ii) MOLECULE TYPE: peptide (xi) SEQUENCE DESCRIPTION: SEQ ID NO: 235:

Met Ser Pro Ile Leu Gly Tyr Trp Lys Ile Lys Gly Leu Val Gln Pro
  1               5                  10                  15

Thr Arg Leu Leu Leu Glu Tyr Leu Glu Glu Lys Tyr Glu Glu His Leu
                 20                  25                  30

Tyr Glu Arg Asp Glu Gly Asp Lys Trp Arg Asn Lys Lys Phe Glu Leu
             35                  40                  45

Gly Leu Glu Phe Pro Asn Leu Pro Tyr Tyr Ile Asp Gly Asp Val Lys
         50                  55                  60

Leu Thr Gln Ser Met Ala Ile Ile Arg Tyr Ile Ala Asp Lys His Asn
 65                  70                  75                  80

Met Leu Gly Gly Cys Pro Lys Glu Arg Ala Glu Ile Ser Met Leu Glu
                 85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
        130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
                180                 185                 190

Leu Lys Ser Ser Lys Tyr Ile Ala Trp Pro Leu Gln Gly Trp Gln Ala
            195                 200                 205

Thr Phe Gly Gly Asp His Pro Pro Lys Ser Asp Leu Val Pro Arg
        210                 215                 220

Gly Ser Pro Gly Ile Pro Gly Ser Thr Arg Ala Ala Ala Ser Ser Thr
225                 230                 235                 240

Pro Pro Ser Arg Glu Ala Tyr Ser Arg Pro Tyr Ser Val Asp Ser Asp
                245                 250                 255

Ser Asp (2) INFORMATION FOR SEQ ID NO: 236:

(i) SEQUENCE CHARACTERISTICS:
          (A) LENGTH: 259 amino acids
          (B) TYPE: amino acid
          (C) STRANDEDNESS: <Unknown>
          (D) TOPOLOGY: unknown (ii) MOLECULE TYPE: peptide (xi) SEQUENCE DESCRIPTION: SEQ ID NO: 236:

Met Ser Pro Ile Leu Gly Tyr Trp Lys Ile Lys Gly Leu Val Gln Pro
  1               5                  10                  15

Thr Arg Leu Leu Leu Glu Tyr Leu Glu Glu Lys Tyr Glu Glu His Leu
                 20                  25                  30

Tyr Glu Arg Asp Glu Gly Asp Lys Trp Arg Asn Lys Lys Phe Glu Leu
             35                  40                  45

Gly Leu Glu Phe Pro Asn Leu Pro Tyr Tyr Ile Asp Gly Asp Val Lys
         50                  55                  60
```

```
-continued

Leu Thr Gln Ser Met Ala Ile Ile Arg Tyr Ile Ala Asp Lys His Asn
 65                  70                  75                  80

Met Leu Gly Gly Cys Pro Lys Glu Arg Ala Glu Ile Ser Met Leu Glu
                 85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
                115                 120                 125

Met Leu Lys Met Phe Glu Asp Arg Leu Cys His Lys Thr Tyr Leu Asn
                130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
                180                 185                 190

Leu Lys Ser Ser Lys Tyr Ile Ala Trp Pro Leu Gln Gly Trp Gln Ala
                195                 200                 205

Thr Phe Gly Gly Gly Asp His Pro Pro Lys Ser Asp Leu Val Pro Arg
210                 215                 220

Gly Ser Pro Gly Ile Pro Gly Ser Thr Arg Ala Ala Ser Ser Arg
225                 230                 235                 240

Pro Tyr Ser Val Asp Ser Asp Ser Asp Thr Asn Ala Lys His Ser Ser
                245                 250                 255

His Asn Arg (2) INFORMATION FOR SEQ ID NO: 237:

(i) SEQUENCE CHARACTERISTICS:
        (A) LENGTH: 257 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 237:

Met Ser Pro Ile Leu Gly Tyr Trp Lys Ile Lys Gly Leu Val Gln Pro
  1               5                  10                  15

Thr Arg Leu Leu Leu Glu Tyr Leu Glu Glu Lys Tyr Glu Glu His Leu
                 20                  25                  30

Tyr Glu Arg Asp Glu Gly Asp Lys Trp Arg Asn Lys Lys Phe Glu Leu
                 35                  40                  45

Gly Leu Glu Phe Pro Asn Leu Pro Tyr Tyr Ile Asp Gly Asp Val Lys
                 50                  55                  60

Leu Thr Gln Ser Met Ala Ile Ile Arg Tyr Ile Ala Asp Lys His Asn
 65                  70                  75                  80

Met Leu Gly Gly Cys Pro Lys Glu Arg Ala Glu Ile Ser Met Leu Glu
                 85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
                115                 120                 125

Met Leu Lys Met Phe Glu Asp Arg Leu Cys His Lys Thr Tyr Leu Asn
                130                 135                 140
```

```
Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Pro Gly Ile Pro Gly Ser Thr Arg Ala Ala Ser Thr Asn
225                 230                 235                 240

Ala Lys His Ser Ser His Asn Arg Arg Leu Arg Thr Arg Ser Arg Pro
            245                 250                 255

Asn (2) INFORMATION FOR SEQ ID NO: 238:

(i) SEQUENCE CHARACTERISTICS:
        (A) LENGTH: 247 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 238:

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
            35                  40                  45

Gly Leu Glu Phe Pro Asn Leu Pro Tyr Tyr Ile Asp Gly Asp Val Lys
        50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220
```

-continued

```
Gly Ser Pro Gly Ile Pro Gly Ser Thr Arg Ala Ala Ala Ser Thr Asn
225                 230                 235                 240

Ala Lys His Ser Ser His Asn
                    245
```

(2) INFORMATION FOR SEQ ID NO: 239:

(i) SEQUENCE CHARACTERISTICS:
        (A) LENGTH: 248 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 239:

```
Met Ser Pro Ile Leu Gly Tyr Trp Lys Ile Lys Gly Leu Val Gln Pro
1                   5                   10                  15

Thr Arg Leu Leu Leu Glu Tyr Leu Glu Glu Lys Tyr Glu Glu His Leu
                    20                  25                  30

Tyr Glu Arg Asp Glu Gly Asp Lys Trp Arg Asn Lys Lys Phe Glu Leu
                35                  40                  45

Gly Leu Glu Phe Pro Asn Leu Pro Tyr Tyr Ile Asp Gly Asp Val Lys
        50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
                115                 120                 125

Met Leu Lys Met Phe Glu Asp Arg Leu Cys His Lys Thr Tyr Leu Asn
130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
                180                 185                 190

Leu Lys Ser Ser Lys Tyr Ile Ala Trp Pro Leu Gln Gly Trp Gln Ala
                195                 200                 205

Thr Phe Gly Gly Gly Asp His Pro Pro Lys Ser Asp Leu Val Pro Arg
        210                 215                 220

Gly Ser Pro Gly Ile Pro Gly Ser Thr Arg Ala Ala Ala Ser Ser Ser
225                 230                 235                 240

His Asn Arg Arg Leu Arg Thr Arg
                    245
```

(2) INFORMATION FOR SEQ ID NO: 240:

(i) SEQUENCE CHARACTERISTICS:
        (A) LENGTH: 248 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 240:

```
Met Ser Pro Ile Leu Gly Tyr Trp Lys Ile Lys Gly Leu Val Gln Pro
  1               5                  10                  15
Thr Arg Leu Leu Leu Glu Tyr Leu Glu Glu Lys Tyr Glu Glu His Leu
                 20                  25                  30
Tyr Glu Arg Asp Glu Gly Asp Lys Trp Arg Asn Lys Lys Phe Glu Leu
             35                  40                  45
Gly Leu Glu Phe Pro Asn Leu Pro Tyr Tyr Ile Asp Gly Asp Val Lys
 50                  55                  60
Leu Thr Gln Ser Met Ala Ile Ile Arg Tyr Ile Ala Asp Lys His Asn
 65                  70                  75                  80
Met Leu Gly Gly Cys Pro Lys Glu Arg Ala Glu Ile Ser Met Leu Glu
                 85                  90                  95
Gly Ala Val Leu Asp Ile Arg Tyr Gly Val Ser Arg Ile Ala Tyr Ser
                100                 105                 110
Lys Asp Phe Glu Thr Leu Lys Val Asp Phe Leu Ser Lys Leu Pro Glu
            115                  120                 125
Met Leu Lys Met Phe Glu Asp Arg Leu Cys His Lys Thr Tyr Leu Asn
            130                  135                 140
Gly Asp His Val Thr His Pro Asp Phe Met Leu Tyr Asp Ala Leu Asp
145                 150                  155                 160
Val Val Leu Tyr Met Asp Pro Met Cys Leu Asp Ala Phe Pro Lys Leu
                165                  170                 175
Val Cys Phe Lys Lys Arg Ile Glu Ala Ile Pro Gln Ile Asp Lys Tyr
                180                  185                 190
Leu Lys Ser Ser Lys Tyr Ile Ala Trp Pro Leu Gln Gly Trp Gln Ala
            195                  200                 205
Thr Phe Gly Gly Asp His Pro Pro Lys Ser Asp Leu Val Pro Arg
            210                  215                 220
Gly Ser Pro Gly Ile Pro Gly Ser Thr Arg Ala Ala Ala Ser Arg Arg
225                 230                  235                 240
Leu Arg Thr Arg Ser Arg Pro Asn
            245
```

(2) INFORMATION FOR SEQ ID NO: 241:

(i) SEQUENCE CHARACTERISTICS:
        (A) LENGTH: 282 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 241:

```
Met Ser Pro Ile Leu Gly Tyr Trp Lys Ile Lys Gly Leu Val Gln Pro
  1               5                  10                  15
Thr Arg Leu Leu Leu Glu Tyr Leu Glu Glu Lys Tyr Glu Glu His Leu
                 20                  25                  30
Tyr Glu Arg Asp Glu Gly Asp Lys Trp Arg Asn Lys Lys Phe Glu Leu
             35                  40                  45
Gly Leu Glu Phe Pro Asn Leu Pro Tyr Tyr Ile Asp Gly Asp Val Lys
 50                  55                  60
Leu Thr Gln Ser Met Ala Ile Ile Arg Tyr Ile Ala Asp Lys His Asn
 65                  70                  75                  80
```

```
Met Leu Gly Gly Cys Pro Lys Glu Arg Ala Glu Ile Ser Met Leu Glu
                    85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
                115                 120                 125

Met Leu Lys Met Phe Glu Asp Arg Leu Cys His Lys Thr Tyr Leu Asn
130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
                180                 185                 190

Leu Lys Ser Ser Lys Tyr Ile Ala Trp Pro Leu Gln Gly Trp Gln Ala
                195                 200                 205

Thr Phe Gly Gly Gly Asp His Pro Pro Lys Ser Asp Leu Val Pro Arg
                210                 215                 220

Gly Ser Pro Gly Ile Pro Gly Ser Thr Arg Ala Ala Ser Arg Val
225                 230                 235                 240

Gly Gln Cys Thr Asp Ser Asp Val Arg Arg Pro Trp Ala Arg Ser Cys
                245                 250                 255

Ala His Gln Gly Cys Gly Ala Gly Thr Arg Asn Ser His Gly Cys Ile
                260                 265                 270

Thr Arg Pro Leu Arg Gln Ala Ser Ala His
                275                 280

(2) INFORMATION FOR SEQ ID NO: 242:

(i) SEQUENCE CHARACTERISTICS:
        (A) LENGTH: 257 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 242:

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
                20                  25                  30

Tyr Glu Arg Asp Glu Gly Asp Lys Trp Arg Asn Lys Lys Phe Glu Leu
                35                  40                  45

Gly Leu Glu Phe Pro Asn Leu Pro Tyr Tyr Ile Asp Gly Asp Val Lys
50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
                115                 120                 125

Met Leu Lys Met Phe Glu Asp Arg Leu Cys His Lys Thr Tyr Leu Asn
130                 135                 140
```

-continued

```
Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Pro Gly Ile Pro Gly Ser Thr Arg Ala Ala Ser Arg Val
225                 230                 235                 240

Gly Gln Cys Thr Asp Ser Asp Val Arg Arg Pro Trp Ala Arg Ser Cys
                245                 250                 255

Ala (2) INFORMATION FOR SEQ ID NO: 243:

(i) SEQUENCE CHARACTERISTICS:
        (A) LENGTH: 259 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 243:

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
                20                  25                  30

Tyr Glu Arg Asp Glu Gly Asp Lys Trp Arg Asn Lys Lys Phe Glu Leu
            35                  40                  45

Gly Leu Glu Phe Pro Asn Leu Pro Tyr Tyr Ile Asp Gly Asp Val Lys
        50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
        130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220
```

```
Gly Ser Pro Gly Ile Pro Gly Ser Thr Arg Ala Ala Ala Ser Val Arg
225                 230                 235                 240

Arg Pro Trp Ala Arg Ser Cys Ala His Gln Gly Cys Gly Ala Gly Thr
                245                 250                 255

Arg Asn Ser
```

(2) INFORMATION FOR SEQ ID NO: 244:

(i) SEQUENCE CHARACTERISTICS:
        (A) LENGTH: 257 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 244:

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
                20                  25                  30

Tyr Glu Arg Asp Glu Gly Asp Lys Trp Arg Asn Lys Lys Phe Glu Leu
            35                  40                  45

Gly Leu Glu Phe Pro Asn Leu Pro Tyr Tyr Ile Asp Gly Asp Val Lys
50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
                115                 120                 125

Met Leu Lys Met Phe Glu Asp Arg Leu Cys His Lys Thr Tyr Leu Asn
130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
                180                 185                 190

Leu Lys Ser Ser Lys Tyr Ile Ala Trp Pro Leu Gln Gly Trp Gln Ala
                195                 200                 205

Thr Phe Gly Gly Gly Asp His Pro Pro Lys Ser Asp Leu Val Pro Arg
    210                 215                 220

Gly Ser Pro Gly Ile Pro Gly Ser Thr Arg Ala Ala Ala Ser Gly Thr
225                 230                 235                 240

Arg Asn Ser His Gly Cys Ile Thr Arg Pro Leu Arg Gln Ala Ser Gln
                245                 250                 255

His
```

(2) INFORMATION FOR SEQ ID NO: 245:

(i) SEQUENCE CHARACTERISTICS:
        (A) LENGTH: 282 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 245:

```
Met Ser Pro Ile Leu Gly Tyr Trp Lys Ile Lys Gly Leu Val Gln Pro
  1               5                  10                  15
Thr Arg Leu Leu Leu Glu Tyr Leu Glu Glu Lys Tyr Glu Glu His Leu
                 20                  25                  30
Tyr Glu Arg Asp Glu Gly Asp Lys Trp Arg Asn Lys Lys Phe Glu Leu
             35                  40                  45
Gly Leu Glu Phe Pro Asn Leu Pro Tyr Tyr Ile Asp Gly Asp Val Lys
 50                  55                  60
Leu Thr Gln Ser Met Ala Ile Ile Arg Tyr Ile Ala Asp Lys His Asn
 65                  70                  75                  80
Met Leu Gly Gly Cys Pro Lys Glu Arg Ala Glu Ile Ser Met Leu Glu
                 85                  90                  95
Gly Ala Val Leu Asp Ile Arg Tyr Gly Val Ser Arg Ile Ala Tyr Ser
                100                 105                 110
Lys Asp Phe Glu Thr Leu Lys Val Asp Phe Leu Ser Lys Leu Pro Glu
            115                 120                 125
Met Leu Lys Met Phe Glu Asp Arg Leu Cys His Lys Thr Tyr Leu Asn
130                 135                 140
Gly Asp His Val Thr His Pro Asp Phe Met Leu Tyr Asp Ala Leu Asp
145                 150                 155                 160
Val Val Leu Tyr Met Asp Pro Met Cys Leu Asp Ala Phe Pro Lys Leu
                165                 170                 175
Val Cys Phe Lys Lys Arg Ile Glu Ala Ile Pro Gln Ile Asp Lys Tyr
                180                 185                 190
Leu Lys Ser Ser Lys Tyr Ile Ala Trp Pro Leu Gln Gly Trp Gln Ala
            195                 200                 205
Thr Phe Gly Gly Asp His Pro Pro Lys Ser Asp Leu Val Pro Arg
210                 215                 220
Gly Ser Pro Gly Ile Pro Gly Ser Thr Arg Ala Ala Ala Ser Arg Tyr
225                 230                 235                 240
Lys His Asp Ile Gly Cys Asp Ala Gly Val Asp Lys Lys Ser Ser Ser
                245                 250                 255
Val Arg Gly Gly Cys Gly Ala His Ser Ser Pro Pro Arg Ala Gly Arg
                260                 265                 270
Gly Pro Arg Gly Thr Met Val Ser Arg Leu
            275                 280
```

(2) INFORMATION FOR SEQ ID NO: 246:

(i) SEQUENCE CHARACTERISTICS:
        (A) LENGTH: 262 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 246:

```
Met Ser Pro Ile Leu Gly Tyr Trp Lys Ile Lys Gly Leu Val Gln Pro
  1               5                  10                  15
Thr Arg Leu Leu Leu Glu Tyr Leu Glu Glu Lys Tyr Glu Glu His Leu
                 20                  25                  30
Tyr Glu Arg Asp Glu Gly Asp Lys Trp Arg Asn Lys Lys Phe Glu Leu
             35                  40                  45
```

```
Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
                115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
                180                 185                 190

Leu Lys Ser Ser Lys Tyr Ile Ala Trp Pro Leu Gln Gly Trp Gln Ala
                195                 200                 205

Thr Phe Gly Gly Asp His Pro Pro Lys Ser Asp Leu Val Pro Arg
    210                 215                 220

Gly Ser Pro Gly Ile Pro Gly Ser Thr Arg Ala Ala Ser Arg Tyr
225                 230                 235                 240

Lys His Asp Ile Gly Cys Asp Ala Gly Val Asp Lys Lys Ser Ser Ser
                245                 250                 255

Val Arg Gly Gly Cys Gly
                260

(2) INFORMATION FOR SEQ ID NO: 247:

(i) SEQUENCE CHARACTERISTICS:
        (A) LENGTH: 264 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 247:

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
                20                  25                  30

Tyr Glu Arg Asp Glu Gly Asp Lys Trp Arg Asn Lys Lys Phe Glu Leu
                35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
                115                 120                 125
```

```
Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                     150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Pro Gly Ile Pro Gly Ser Thr Arg Ala Ala Ser Gly Cys
225                 230                 235                 240

Asp Ala Gly Val Asp Lys Lys Ser Ser Val Arg Gly Gly Cys Gly
                245                 250                 255

Ala His Ser Ser Pro Pro Arg Ala
            260
```

(2) INFORMATION FOR SEQ ID NO: 248:

(i) SEQUENCE CHARACTERISTICS:
        (A) LENGTH: 259 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 248:

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
                35                  40                  45

Gly Leu Glu Phe Pro Asn Leu Pro Tyr Tyr Ile Asp Gly Asp Val Lys
50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                     150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205
```

```
Thr Phe Gly Gly Gly Asp His Pro Pro Lys Ser Asp Leu Val Pro Arg
    210                 215                 220

Gly Ser Pro Gly Ile Pro Gly Ser Thr Arg Ala Ala Ala Ser Gly Ala
225                 230                 235                 240

His Ser Ser Pro Pro Arg Ala Gly Arg Gly Pro Arg Gly Thr Met Val
                245                 250                 255

Ser Arg Leu
```

(2) INFORMATION FOR SEQ ID NO: 249:

(i) SEQUENCE CHARACTERISTICS:
        (A) LENGTH: 44 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 249:

```
Ser Gly Ser Pro Pro Cys Cys Cys Ser Trp Gly Arg Phe Met Gln Gly
1               5                   10                  15

Gly Leu Phe Gly Gly Arg Thr Asp Gly Cys Gly Ala His Arg Asn Arg
                20                  25                  30

Thr Ser Ala Ser Leu Glu Pro Pro Ser Ser Asp Tyr
                35                  40
```

(2) INFORMATION FOR SEQ ID NO: 250:

(i) SEQUENCE CHARACTERISTICS:
        (A) LENGTH: 40 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 250:

```
Ser His Ser Gly Gly Met Asn Arg Ala Tyr Gly Asp Val Phe Arg Glu
1               5                   10                  15

Leu Arg Asp Arg Trp Asn Ala Thr Ser His His Thr Arg Pro Thr Pro
                20                  25                  30

Gln Leu Pro Arg Gly Pro Asn Ser
                35                  40
```

(2) INFORMATION FOR SEQ ID NO: 251:

(i) SEQUENCE CHARACTERISTICS:
        (A) LENGTH: 21 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 251:

```
Asp Thr Asn Ala Lys His Ser Ser His Asn Arg Arg Leu Arg Thr Arg
1               5                   10                  15

Ser Arg Pro Asn Gly
                20
```

(2) INFORMATION FOR SEQ ID NO: 252:

(i) SEQUENCE CHARACTERISTICS:
        (A) LENGTH: 23 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 252:

```
Cys Gly Ala Gly Thr Arg Asn Ser His Gly Cys Ile Thr Arg Pro Leu
 1               5                  10                  15

Arg Gln Ala Ser Ala His Gly
            20
```

(2) INFORMATION FOR SEQ ID NO: 253:

(i) SEQUENCE CHARACTERISTICS:
        (A) LENGTH: 11 amino acids
        (B) TYPE: amino acid
        (C) STRANDEDNESS: <Unknown>
        (D) TOPOLOGY: unknown (ii) MOLECULE TYPE: peptide (ix) FEATURE:
        (A) NAME/KEY: Modified Site
        (B) LOCATION: 1
        (D) OTHER INFORMATION: "Xaa=Ser or Thr"

(xi) SEQUENCE DESCRIPTION: SEQ ID NO: 253:

```
Xaa Thr Xaa Xaa Ser Xaa Xaa Xaa Asn Xaa Arg
 1               5                  10
```

(2) INFORMATION FOR SEQ ID NO: 254:

(i) SEQUENCE CHARACTERISTICS:
        (A) LENGTH: 8 amino acids
        (B) TYPE: amino acid
        (C) STRANDEDNESS: <Unknown>
        (D) TOPOLOGY: unknown (ii) MOLECULE TYPE: peptide (ix) FEATURE:
        (A) NAME/KEY: Modified Site
        (B) LOCATION: 2
        (D) OTHER INFORMATION: "Xaa=Ser, Ala or Gly"

(xi) SEQUENCE DESCRIPTION: SEQ ID NO: 254:

```
Asp Xaa Asp Xaa Arg Arg Xaa Xaa
 1               5
```

(2) INFORMATION FOR SEQ ID NO: 255:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: unknown (ii) MOLECULE TYPE: peptide (ix) FEATURE:
        (A) NAME/KEY: Modified Site
        (B) LOCATION: 7
        (D) OTHER INFORMATION: "Xaa=Ala or Phe"

(xi) SEQUENCE DESCRIPTION: SEQ ID NO: 255:

Val Arg Ser Gly Cys Gly Xaa Xaa Ser Ser
1               5                   10

(2) INFORMATION FOR SEQ ID NO: 256:

(i) SEQUENCE CHARACTERISTICS:
        (A) LENGTH: 11 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 256:

Asn Thr Arg Lys Ser Ser Arg Ser Asn Pro Arg
1               5                   10

(2) INFORMATION FOR SEQ ID NO: 257:

(i) SEQUENCE CHARACTERISTICS:
        (A) LENGTH: 11 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 257:

Ser Thr Lys Arg Ser Leu Ile Tyr Asn His Arg
1               5                   10

(2) INFORMATION FOR SEQ ID NO: 258:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 258:

Ser Thr Gly Arg Lys Val Phe Asn Arg Arg
1               5                   10

(2) INFORMATION FOR SEQ ID NO: 259:

(i) SEQUENCE CHARACTERISTICS:
        (A) LENGTH: 11 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 259:

Thr Asn Ala Lys His Ser Ser His Asn Arg Arg
1               5                   10

(2) INFORMATION FOR SEQ ID NO: 260:

(i) SEQUENCE CHARACTERISTICS:
        (A) LENGTH: 8 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 260:

Asp Ser Asp Val Arg Arg Pro Trp
1               5

(2) INFORMATION FOR SEQ ID NO: 261:

(i) SEQUENCE CHARACTERISTICS:
            (A) LENGTH: 8 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 261:

Ala Ala Asp Gln Arg Arg Gly Trp
1               5

(2) INFORMATION FOR SEQ ID NO: 262:

(i) SEQUENCE CHARACTERISTICS:
            (A) LENGTH: 8 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 262:

Asp Gly Arg Gly Gly Arg Ser Tyr
1               5

(2) INFORMATION FOR SEQ ID NO: 263:

(i) SEQUENCE CHARACTERISTICS:
            (A) LENGTH: 4 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 263:

Arg Val Arg Ser
1

(2) INFORMATION FOR SEQ ID NO: 264:

(i) SEQUENCE CHARACTERISTICS:
            (A) LENGTH: 12 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 264:

Ser Val Arg Ser Gly Cys Gly Phe Arg Gly Ser Ser
1               5                   10

(2) INFORMATION FOR SEQ ID NO: 265:

(i) SEQUENCE CHARACTERISTICS:
            (A) LENGTH: 11 amino acids
            (B) TYPE: amino acid
            (C) STRANDEDNESS: <Unknown>
            (D) TOPOLOGY: unknown

```
        (ii) MOLECULE TYPE: peptide (xi) SEQUENCE DESCRIPTION: SEQ ID NO: 265:

Ser Val Arg Gly Gly Cys Gly Ala His Ser Ser
 1               5                  10

(2) INFORMATION FOR SEQ ID NO: 266:

(i) SEQUENCE CHARACTERISTICS:
            (A) LENGTH: 37 amino acids
            (B) TYPE: amino acid
            (C) STRANDEDNESS: single
            (D) TOPOLOGY: unknown (ii) MOLECULE TYPE: peptide (ix) FEATURE:
            (A) NAME/KEY: Other
            (B) LOCATION: 2...2
            (D) OTHER INFORMATION: Xaa=Lys(dns)

(xi) SEQUENCE DESCRIPTION: SEQ ID NO: 266:

Cys Xaa Phe Ile Thr Lys Ala Leu Gly Ile Ser Tyr Gly Arg Lys Lys
 1               5                  10                  15

Arg Arg Gln Arg Arg Arg Pro Pro Gln Gly Ser Gln Thr His Gln Val
             20                  25                  30

Ser Leu Ser Lys Gln
         35

(2) INFORMATION FOR SEQ ID NO: 267:

(i) SEQUENCE CHARACTERISTICS:
            (A) LENGTH: 18 amino acids
            (B) TYPE: amino acid
            (C) STRANDEDNESS: single
            (D) TOPOLOGY: unknown (ii) MOLECULE TYPE: peptide (ix) FEATURE:
            (A) NAME/KEY: Other
            (B) LOCATION: 1...1
            (D) OTHER INFORMATION: Xaa=Ac-Cys (xi) SEQUENCE DESCRIPTION: SEQ ID NO: 267:

Xaa Leu Asn Gly Gly Val Lys Met Tyr Val Glu Ser Val Asp Arg Tyr
 1               5                  10                  15

Val Cys (2) INFORMATION FOR SEQ ID NO: 268:

(i) SEQUENCE CHARACTERISTICS:
            (A) LENGTH: 22 amino acids
            (B) TYPE: amino acid
            (C) STRANDEDNESS: single
            (D) TOPOLOGY: unknown (ii) MOLECULE TYPE: peptide (ix) FEATURE:
            (A) NAME/KEY: Other
            (B) LOCATION: 1...1
            (D) OTHER INFORMATION: Xaa=Ac-Cys
```

(xi) SEQUENCE DESCRIPTION: SEQ ID NO: 268:

Xaa Leu Asn Gly Gly Val Lys Phe Ile Thr Cys Met Tyr Val Glu Ser
 1               5                  10                  15

Val Asp Arg Tyr Val Cys
            20

(2) INFORMATION FOR SEQ ID NO: 269:

(i) SEQUENCE CHARACTERISTICS:
        (A) LENGTH: 21 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 2...2
        (D) OTHER INFORMATION: Xaa=Lys(dns)

(xi) SEQUENCE DESCRIPTION: SEQ ID NO: 269:

Cys Xaa Arg Leu Asn Gly Gly Val Ser Met Tyr Val Glu Ser Val Asp
 1               5                  10                  15

Arg Tyr Val Cys Arg
            20

(2) INFORMATION FOR SEQ ID NO: 270:

(i) SEQUENCE CHARACTERISTICS:
        (A) LENGTH: 40 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=biotin-Lys(dns)

(xi) SEQUENCE DESCRIPTION: SEQ ID NO: 270:

Xaa Ser Ala Arg Asp Ser Gly Pro Ala Glu Asp Gly Ser Arg Ala Val
 1               5                  10                  15

Arg Leu Asn Gly Val Glu Asn Ala Asn Thr Arg Lys Ser Ser Arg Ser
            20                  25                  30

Asn Pro Arg Gly Arg Arg His Pro
            35                  40

(2) INFORMATION FOR SEQ ID NO: 271:

(i) SEQUENCE CHARACTERISTICS:
        (A) LENGTH: 45 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=biotin-Lys(dns)

(xi) SEQUENCE DESCRIPTION: SEQ ID NO: 271:

Xaa Ser Ser Ala Asp Ala Glu Lys Cys Ala Gly Ser Leu Leu Trp Trp
1               5                   10                  15

Gly Arg Gln Asn Asn Ser Gly Cys Gly Ser Pro Thr Lys Lys His Leu
                20                  25                  30

Lys His Arg Asn Arg Ser Gln Thr Ser Ser Ser His
        35                  40                  45

(2) INFORMATION FOR SEQ ID NO: 272:

(i) SEQUENCE CHARACTERISTICS:
        (A) LENGTH: 45 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=biotin-Lys(dns)

(xi) SEQUENCE DESCRIPTION: SEQ ID NO: 272:

Xaa Arg Glu Phe Ala Glu Arg Arg Leu Trp Gly Cys Asp Asp Leu Ser
1               5                   10                  15

Trp Arg Leu Asp Ala Glu Gly Cys Gly Pro Thr Pro Ser Asn Arg Ala
                20                  25                  30

Val Lys His Arg Lys Pro Arg Pro Arg Ser Pro Ala Leu
        35                  40                  45

(2) INFORMATION FOR SEQ ID NO: 273:

(i) SEQUENCE CHARACTERISTICS:
        (A) LENGTH: 41 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=biotin-Ser (xi) SEQUENCE DESCRIPTION: SEQ ID NO: 273:

Xaa Gly Ser His Ser Gly Gly Met Asn Arg Ala Tyr Gly Asp Val Phe
1               5                   10                  15

Arg Glu Leu Arg Asp Arg Trp Tyr Ala Thr Ser His His Thr Arg Pro
                20                  25                  30

Thr Pro Gln Leu Pro Arg Gly Pro Asn
        35                  40

(2) INFORMATION FOR SEQ ID NO: 274:

(i) SEQUENCE CHARACTERISTICS:
        (A) LENGTH: 42 amino acids
        (B) TYPE: amino acid
        (C) STRANDEDNESS: single
        (D) TOPOLOGY: unknown

```
    (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 274:

Xaa Ser Gly Ser His Ser Gly Gly Met Asn Arg Ala Tyr Gly Asp Val
 1               5                  10                  15

Phe Arg Glu Leu Arg Asp Arg Trp Tyr Ala Thr Ser His His Thr Arg
            20                  25                  30

Pro Thr Pro Gln Leu Pro Arg Gly Pro Asn
            35                  40

(2) INFORMATION FOR SEQ ID NO: 275:

(i) SEQUENCE CHARACTERISTICS:
        (A) LENGTH: 40 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=biotin-Lys(dns)

(xi) SEQUENCE DESCRIPTION: SEQ ID NO: 275:

Xaa Ser His Ser Gly Gly Met Asn Arg Ala Tyr Gly Asp Val Phe Arg
 1               5                  10                  15

Glu Leu Arg Asp Arg Trp Asn Ala Thr Ser His His Thr Arg Pro Thr
            20                  25                  30

Pro Gln Leu Pro Arg Gly Pro Asn
            35                  40

(2) INFORMATION FOR SEQ ID NO: 276:

(i) SEQUENCE CHARACTERISTICS:
        (A) LENGTH: 41 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 276:

Xaa Ser His Ser Gly Gly Met Asn Arg Ala Tyr Gly Asp Val Phe Arg
 1               5                  10                  15

Glu Leu Arg Asp Arg Trp Asn Ala Thr Ser His His Thr Arg Pro Thr
            20                  25                  30

Pro Gln Leu Pro Arg Gly Pro Asn Ser
            35                  40
```

-continued (2) INFORMATION FOR SEQ ID NO: 277:

(i) SEQUENCE CHARACTERISTICS:
  (A) LENGTH: 45 amino acids
  (B) TYPE: amino acid
  (C) STRANDEDNESS: single
  (D) TOPOLOGY: unknown (ii) MOLECULE TYPE: peptide (ix) FEATURE:
  (A) NAME/KEY: Other
  (B) LOCATION: 1...1
  (D) OTHER INFORMATION: Xaa=Lys(dns)

(xi) SEQUENCE DESCRIPTION: SEQ ID NO: 277:

```
Xaa Ser Gln Gly Ser Lys Gln Cys Met Gln Tyr Arg Thr Gly Arg Leu
 1               5                  10                  15
Thr Val Gly Ser Glu Tyr Gly Cys Gly Met Asn Pro Ala Arg His Ala
                20                  25                  30
Thr Pro Ala Tyr Pro Ala Arg Leu Leu Pro Arg Tyr Arg
            35                  40                  45
```

(2) INFORMATION FOR SEQ ID NO: 278:

(i) SEQUENCE CHARACTERISTICS:
  (A) LENGTH: 45 amino acids
  (B) TYPE: amino acid
  (C) STRANDEDNESS: single
  (D) TOPOLOGY: unknown (ii) MOLECULE TYPE: peptide (ix) FEATURE:
  (A) NAME/KEY: Other
  (B) LOCATION: 1...1
  (D) OTHER INFORMATION: Xaa=Lys(dns)

(xi) SEQUENCE DESCRIPTION: SEQ ID NO: 278:

```
Xaa Arg Val Gly Gln Cys Thr Asp Ser Asp Val Arg Arg Pro Trp Ala
 1               5                  10                  15
Arg Ser Cys Ala His Gln Gly Cys Gly Ala Gly Thr Arg Asn Ser His
                20                  25                  30
Gly Cys Ile Thr Arg Pro Leu Arg Gln Ala Ser Ala His
            35                  40                  45
```

(2) INFORMATION FOR SEQ ID NO: 279:

(i) SEQUENCE CHARACTERISTICS:
  (A) LENGTH: 24 amino acids
  (B) TYPE: amino acid
  (C) STRANDEDNESS: single
  (D) TOPOLOGY: unknown (ii) MOLECULE TYPE: peptide (ix) FEATURE:
  (A) NAME/KEY: Other
  (B) LOCATION: 1...1
  (D) OTHER INFORMATION: Xaa=biotin-Lys(dns)

(xi) SEQUENCE DESCRIPTION: SEQ ID NO: 279:

```
Xaa Ser Gly Ser Gly Arg Val Gly Gln Cys Thr Asp Ser Asp Val Arg
 1               5                  10                  15
Arg Pro Trp Ala Arg Ser Cys Ala
                20
```

-continued (2) INFORMATION FOR SEQ ID NO: 280:

(i) SEQUENCE CHARACTERISTICS:
        (A) LENGTH: 20 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 280:

```
Xaa Arg Val Gly Gln Cys Thr Asp Ser Asp Val Arg Arg Pro Trp Ala
 1               5                  10                  15
Arg Ser Cys Ala
            20
```

(2) INFORMATION FOR SEQ ID NO: 281:

(i) SEQUENCE CHARACTERISTICS:
        (A) LENGTH: 41 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 281:

```
Xaa Ser Thr Pro Pro Ser Arg Glu Ala Tyr Ser Arg Pro Tyr Ser Val
 1               5                  10                  15
Asp Ser Asp Ser Asp Thr Asn Ala Lys His Ser Ser His Asn Arg Arg
            20                  25                  30
Leu Arg Thr Arg Ser Arg Pro Asn Gly
            35                  40
```

(2) INFORMATION FOR SEQ ID NO: 282:

(i) SEQUENCE CHARACTERISTICS:
        (A) LENGTH: 40 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 282:

```
Xaa Arg Gly Ser Thr Gly Thr Ala Gly Gly Glu Arg Ser Gly Val Leu
 1               5                  10                  15
Asn Leu His Thr Arg Asp Asn Ala Ser Gly Ser Gly Phe Lys Pro Trp
            20                  25                  30
Tyr Pro Ser Asn Arg Gly His Lys
            35                  40
```

```
(2) INFORMATION FOR SEQ ID NO: 283:

(i) SEQUENCE CHARACTERISTICS:
        (A) LENGTH: 20 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 283:

Xaa Ser Gly Ser Gly Leu Tyr Ala Asn Pro Gly Met Tyr Ser Arg Leu
 1               5                  10                  15

His Ser Pro Ala
            20

(2) INFORMATION FOR SEQ ID NO: 284:

(i) SEQUENCE CHARACTERISTICS:
        (A) LENGTH: 20 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=biotin-Lys(dns)

(xi) SEQUENCE DESCRIPTION: SEQ ID NO: 284:

Xaa Ser Gly Ser Gly Leu Tyr Ala Asn Pro Gly Met Tyr Ser Arg Leu
 1               5                  10                  15

His Ser Pro Ala
            20

(2) INFORMATION FOR SEQ ID NO: 285:

(i) SEQUENCE CHARACTERISTICS:
        (A) LENGTH: 45 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 285:

Xaa Ser Asp His Ala Leu Gly Thr Asn Leu Arg Ser Asp Asn Ala Lys
 1               5                  10                  15

Glu Pro Gly Asp Tyr Asn Cys Cys Gly Asn Gly Asn Ser Thr Gly Arg
                20                  25                  30

Lys Val Phe Asn Arg Arg Arg Pro Ser Ala Ile Pro Thr
                35                  40                  45
```

-continued (2) INFORMATION FOR SEQ ID NO: 286:

(i) SEQUENCE CHARACTERISTICS:
        (A) LENGTH: 42 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 286:

```
Xaa Ser Pro Cys Gly Gly Ser Trp Gly Arg Phe Met Gln Gly Gly Leu
 1               5                  10                  15

Phe Gly Gly Arg Thr Asp Gly Cys Gly Ala His Arg Asn Arg Thr Ser
                20                  25                  30

Ala Ser Leu Glu Pro Pro Ser Ser Asp Tyr
                35                  40
```

(2) INFORMATION FOR SEQ ID NO: 287:

(i) SEQUENCE CHARACTERISTICS:
        (A) LENGTH: 45 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 287:

```
Xaa Arg Tyr Lys His Asp Ile Gly Cys Asp Ala Gly Val Asp Lys Lys
 1               5                  10                  15

Ser Ser Ser Val Arg Gly Gly Cys Gly Ala His Ser Ser Pro Pro Arg
                20                  25                  30

Ala Gly Arg Gly Pro Arg Gly Thr Met Val Ser Arg Leu
                35                  40                  45
```

(2) INFORMATION FOR SEQ ID NO: 288:

(i) SEQUENCE CHARACTERISTICS:
        (A) LENGTH: 42 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 288:

```
Xaa Ser Ala Arg Asp Ser Gly Pro Ala Glu Asp Gly Ser Arg Ala Val
 1               5                  10                  15

Arg Leu Asn Gly Val Glu Asn Ala Asn Thr Arg Lys Ser Ser Arg Ser
                20                  25                  30

Asn Pro Arg Gly Arg Arg His Pro Gly Gly
                35                  40
```

(2) INFORMATION FOR SEQ ID NO: 289:

(i) SEQUENCE CHARACTERISTICS:
        (A) LENGTH: 40 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 289:

```
Xaa Ser Lys Ser Gly Glu Gly Gly Asp Ser Ser Arg Gly Glu Thr Gly
 1               5                  10                  15

Trp Ala Arg Val Arg Ser His Ala Met Thr Ala Gly Arg Phe Arg Trp
            20                  25                  30

Tyr Asn Gln Leu Pro Ser Asp Arg
        35                  40
```

(2) INFORMATION FOR SEQ ID NO: 290:

(i) SEQUENCE CHARACTERISTICS:
        (A) LENGTH: 41 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 290:

```
Xaa Ser Glu Ala Asn Leu Asp Gly Arg Lys Ser Arg Tyr Ser Ser Pro
 1               5                  10                  15

Arg Arg Asn Ser Ser Thr Arg Pro Arg Thr Ser Pro Asn Ser Val His
            20                  25                  30

Ala Arg Tyr Pro Ser Thr Asp His Asp
        35                  40
```

(2) INFORMATION FOR SEQ ID NO: 291:

(i) SEQUENCE CHARACTERISTICS:
        (A) LENGTH: 44 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Modified Base
        (B) LOCATION: 1...1
        (D) OTHER INFORMATION: Xaa=biotin-S (xi) SEQUENCE DESCRIPTION: SEQ ID NO: 291:

```
Xaa Gly Ser Gly Ser Thr Pro Pro Ser Arg Glu Ala Tyr Ser Arg Pro
 1               5                  10                  15

Tyr Ser Val Asp Ser Asp Ser Asp Thr Asn Ala Lys His Ser Ser His
            20                  25                  30

Asn Arg Arg Leu Arg Thr Arg Ser Arg Pro Asn Gly
        35                  40
```

(2) INFORMATION FOR SEQ ID NO: 292:

(i) SEQUENCE CHARACTERISTICS:
       (A) LENGTH: 23 amino acids
       (B) TYPE: amino acid
       (C) STRANDEDNESS: single
       (D) TOPOLOGY: unknown (ii) MOLECULE TYPE: peptide (ix) FEATURE:
       (A) NAME/KEY: Other
       (B) LOCATION: 1...1
       (D) OTHER INFORMATION: Xaa=Lys(dns)

(xi) SEQUENCE DESCRIPTION: SEQ ID NO: 292:

Xaa Arg Val Gly Gln Cys Thr Asp Ser Asp Val Arg Arg Pro Trp Ala
 1               5                  10                  15

Arg Ser Cys Ala His Gln Gly
            20

(2) INFORMATION FOR SEQ ID NO: 293:

(i) SEQUENCE CHARACTERISTICS:
       (A) LENGTH: 24 amino acids
       (B) TYPE: amino acid
       (C) STRANDEDNESS: single
       (D) TOPOLOGY: unknown (ii) MOLECULE TYPE: peptide (ix) FEATURE:
       (A) NAME/KEY: Other
       (B) LOCATION: 1...1
       (D) OTHER INFORMATION: Xaa=Lys(dns)

(xi) SEQUENCE DESCRIPTION: SEQ ID NO: 293:

Xaa Cys Gly Ala Gly Thr Arg Asn Ser His Gly Cys Ile Thr Arg Pro
 1               5                  10                  15

Leu Arg Gln Ala Ser Ala His Gly
            20

(2) INFORMATION FOR SEQ ID NO: 294:

(i) SEQUENCE CHARACTERISTICS:
       (A) LENGTH: 21 amino acids
       (B) TYPE: amino acid
       (C) STRANDEDNESS: single
       (D) TOPOLOGY: unknown (ii) MOLECULE TYPE: peptide (ix) FEATURE:
       (A) NAME/KEY: Other
       (B) LOCATION: 1...1
       (D) OTHER INFORMATION: Xaa=Lys(dns)

(xi) SEQUENCE DESCRIPTION: SEQ ID NO: 294:

Xaa Glu Asn Ala Asn Thr Arg Lys Ser Ser Arg Ser Asn Pro Arg Gly
 1               5                  10                  15

Arg Arg His Pro Gly
            20

(2) INFORMATION FOR SEQ ID NO: 295:

(i) SEQUENCE CHARACTERISTICS:
       (A) LENGTH: 12 amino acids
       (B) TYPE: amino acid
       (C) STRANDEDNESS: single
       (D) TOPOLOGY: unknown

```
        (ii) MOLECULE TYPE: peptide (ix) FEATURE:
             (A) NAME/KEY: Other
             (B) LOCATION: 1...1
             (D) OTHER INFORMATION: Xaa=Lys(dns)

(xi) SEQUENCE DESCRIPTION: SEQ ID NO: 295:

Xaa Thr Arg Lys Ser Ser Arg Ser Asn Pro Arg Gly
1               5                   10

(2) INFORMATION FOR SEQ ID NO: 296:

(i) SEQUENCE CHARACTERISTICS:
             (A) LENGTH: 16 amino acids
             (B) TYPE: amino acid
             (C) STRANDEDNESS: single
             (D) TOPOLOGY: unknown (ii) MOLECULE TYPE: peptide (ix) FEATURE:
             (A) NAME/KEY: Other
             (B) LOCATION: 1...1
             (D) OTHER INFORMATION: Xaa=Lys(dns)

(xi) SEQUENCE DESCRIPTION: SEQ ID NO: 296:

Xaa Glu Asn Ala Asn Thr Arg Lys Ser Ser Arg Ser Asn Pro Arg Gly
1               5                   10                  15

(2) INFORMATION FOR SEQ ID NO: 297:

(i) SEQUENCE CHARACTERISTICS:
             (A) LENGTH: 17 amino acids
             (B) TYPE: amino acid
             (C) STRANDEDNESS: single
             (D) TOPOLOGY: unknown (ii) MOLECULE TYPE: peptide (ix) FEATURE:
             (A) NAME/KEY: Other
             (B) LOCATION: 1...1
             (D) OTHER INFORMATION: Xaa=Lys(dns)

(xi) SEQUENCE DESCRIPTION: SEQ ID NO: 297:

Xaa Thr Arg Lys Ser Ser Arg Ser Asn Pro Arg Gly Arg Arg His Pro
1               5                   10                  15
Gly (2) INFORMATION FOR SEQ ID NO: 298:

(i) SEQUENCE CHARACTERISTICS:
             (A) LENGTH: 20 amino acids
             (B) TYPE: amino acid
             (C) STRANDEDNESS: single
             (D) TOPOLOGY: unknown (ii) MOLECULE TYPE: peptide (ix) FEATURE:
             (A) NAME/KEY: Other
             (B) LOCATION: 1...1
             (D) OTHER INFORMATION: Xaa=Lys(dns)

(xi) SEQUENCE DESCRIPTION: SEQ ID NO: 298:

Xaa Thr Asn Ala Lys His Ser Ser His Asn Arg Arg Leu Arg Thr Arg
1               5                   10                  15
Ser Arg Pro Asn
            20
```

```
(2) INFORMATION FOR SEQ ID NO: 299:

(i) SEQUENCE CHARACTERISTICS:
        (A) LENGTH: 16 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 299:

Xaa Thr Asn Ala Lys His Ser Ser His Asn Arg Arg Leu Arg Thr Arg
 1               5                  10                  15

(2) INFORMATION FOR SEQ ID NO: 300:

(i) SEQUENCE CHARACTERISTICS:
        (A) LENGTH: 15 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 300:

Xaa Ser Ser His Asn Arg Arg Leu Arg Thr Arg Ser Arg Pro Asn
 1               5                  10                  15

(2) INFORMATION FOR SEQ ID NO: 301:

(i) SEQUENCE CHARACTERISTICS:
        (A) LENGTH: 11 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 301:

Xaa Ser Ser His Asn Arg Arg Leu Arg Thr Arg
 1               5                  10

(2) INFORMATION FOR SEQ ID NO: 302:

(i) SEQUENCE CHARACTERISTICS:
        (A) LENGTH: 22 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)
```

(xi) SEQUENCE DESCRIPTION: SEQ ID NO: 302:

Xaa Val Arg Arg Pro Trp Ala Arg Ser Cys Ala His Gln Gly Cys Gly
 1               5                  10                  15

Ala Gly Thr Arg Asn Ser
            20

(2) INFORMATION FOR SEQ ID NO: 303:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 303:

Xaa Cys Thr Asp Ser Asp Val Arg Arg Pro Trp Ala Arg Ser Cys
 1               5                  10                  15

(2) INFORMATION FOR SEQ ID NO: 304:

(i) SEQUENCE CHARACTERISTICS:
        (A) LENGTH: 41 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 304:

Xaa Ser Arg Ala Asn Thr Asp Gly Arg Lys Ser Arg Tyr Ser Ser Pro
 1               5                  10                  15

Arg Arg Asn Ser Ser Thr Glu Pro Arg Leu Ser Pro Asn Ser Val His
            20                  25                  30

Ala Arg Tyr Pro Ser Thr Asp His Asp
            35                  40

(2) INFORMATION FOR SEQ ID NO: 305:

(i) SEQUENCE CHARACTERISTICS:
        (A) LENGTH: 11 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 305:

Xaa Glu Asn Ala Asn Thr Arg Lys Ser Ser Arg
 1               5                  10

```
(2) INFORMATION FOR SEQ ID NO: 306:

(i) SEQUENCE CHARACTERISTICS:
        (A) LENGTH: 11 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 306:

Xaa Ser Asn Pro Arg Gly Arg Arg His Pro Gly
 1               5                  10

(2) INFORMATION FOR SEQ ID NO: 307:

(i) SEQUENCE CHARACTERISTICS:
        (A) LENGTH: 6 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 307:

Xaa Glu Asn Ala Asn Thr
 1               5

(2) INFORMATION FOR SEQ ID NO: 308:

(i) SEQUENCE CHARACTERISTICS:
        (A) LENGTH: 7 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 308:

Xaa Ala Asn Thr Arg Lys Ser
 1               5

(2) INFORMATION FOR SEQ ID NO: 309:

(i) SEQUENCE CHARACTERISTICS:
        (A) LENGTH: 6 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)
```

```
      (xi) SEQUENCE DESCRIPTION: SEQ ID NO: 309:

Xaa Thr Arg Lys Ser Ser
1               5

(2) INFORMATION FOR SEQ ID NO: 310:

(i) SEQUENCE CHARACTERISTICS:
          (A) LENGTH: 6 amino acids
          (B) TYPE: amino acid
          (C) STRANDEDNESS: single
          (D) TOPOLOGY: unknown (ii) MOLECULE TYPE: peptide (ix) FEATURE:
          (A) NAME/KEY: Other
          (B) LOCATION: 1...1
          (D) OTHER INFORMATION: Xaa=Lys(dns)

(xi) SEQUENCE DESCRIPTION: SEQ ID NO: 310:

Xaa Arg Lys Ser Ser Arg
1               5

(2) INFORMATION FOR SEQ ID NO: 311:

(i) SEQUENCE CHARACTERISTICS:
          (A) LENGTH: 7 amino acids
          (B) TYPE: amino acid
          (C) STRANDEDNESS: single
          (D) TOPOLOGY: unknown (ii) MOLECULE TYPE: peptide (ix) FEATURE:
          (A) NAME/KEY: Other
          (B) LOCATION: 1...1
          (D) OTHER INFORMATION: Xaa=Lys(dns)

(xi) SEQUENCE DESCRIPTION: SEQ ID NO: 311:

Xaa Lys Ser Ser Arg Ser Asn
1               5

(2) INFORMATION FOR SEQ ID NO: 312:

(i) SEQUENCE CHARACTERISTICS:
          (A) LENGTH: 8 amino acids
          (B) TYPE: amino acid
          (C) STRANDEDNESS: single
          (D) TOPOLOGY: unknown (ii) MOLECULE TYPE: peptide (ix) FEATURE:
          (A) NAME/KEY: Other
          (B) LOCATION: 1...1
          (D) OTHER INFORMATION: Xaa=Lys(dns)

(xi) SEQUENCE DESCRIPTION: SEQ ID NO: 312:

Xaa Ser Ser Arg Ser Asn Pro Gly
1               5

(2) INFORMATION FOR SEQ ID NO: 313:

(i) SEQUENCE CHARACTERISTICS:
          (A) LENGTH: 7 amino acids
          (B) TYPE: amino acid
          (C) STRANDEDNESS: single
          (D) TOPOLOGY: unknown
```

```
        (ii) MOLECULE TYPE: peptide (ix) FEATURE:
             (A) NAME/KEY: Other
             (B) LOCATION: 1...1
             (D) OTHER INFORMATION: Xaa=Lys(dns)

(xi) SEQUENCE DESCRIPTION: SEQ ID NO: 313:

Xaa Arg Ser Asn Pro Arg Gly
1               5

(2) INFORMATION FOR SEQ ID NO: 314:

(i) SEQUENCE CHARACTERISTICS:
             (A) LENGTH: 6 amino acids
             (B) TYPE: amino acid
             (C) STRANDEDNESS: single
             (D) TOPOLOGY: unknown (ii) MOLECULE TYPE: peptide (ix) FEATURE:
             (A) NAME/KEY: Other
             (B) LOCATION: 1...1
             (D) OTHER INFORMATION: Xaa=Lys(dns)

(xi) SEQUENCE DESCRIPTION: SEQ ID NO: 314:

Xaa Ser Asn Pro Arg Gly
1               5

(2) INFORMATION FOR SEQ ID NO: 315:

(i) SEQUENCE CHARACTERISTICS:
             (A) LENGTH: 7 amino acids
             (B) TYPE: amino acid
             (C) STRANDEDNESS: single
             (D) TOPOLOGY: unknown (ii) MOLECULE TYPE: peptide (ix) FEATURE:
             (A) NAME/KEY: Other
             (B) LOCATION: 1...1
             (D) OTHER INFORMATION: Xaa=Lys(dns)

(xi) SEQUENCE DESCRIPTION: SEQ ID NO: 315:

Xaa Pro Arg Gly Arg Arg His
1               5

(2) INFORMATION FOR SEQ ID NO: 316:

(i) SEQUENCE CHARACTERISTICS:
             (A) LENGTH: 6 amino acids
             (B) TYPE: amino acid
             (C) STRANDEDNESS: single
             (D) TOPOLOGY: unknown (ii) MOLECULE TYPE: peptide (ix) FEATURE:
             (A) NAME/KEY: Other
             (B) LOCATION: 1...1
             (D) OTHER INFORMATION: Xaa=Lys(dns)

(xi) SEQUENCE DESCRIPTION: SEQ ID NO: 316:

Xaa Arg Arg His Pro Gly
1               5
```

-continued (2) INFORMATION FOR SEQ ID NO: 317:

(i) SEQUENCE CHARACTERISTICS:
        (A) LENGTH: 7 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 317:

Xaa Lys Ser Ser Arg Gly Asn
1               5

(2) INFORMATION FOR SEQ ID NO: 318:

(i) SEQUENCE CHARACTERISTICS:
        (A) LENGTH: 16 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 318:

Xaa Lys Thr Ser Glu Arg Ser Gln Pro Arg Gly Arg Gln Pro Gly
1               5                   10                  15

(2) INFORMATION FOR SEQ ID NO: 319:

(i) SEQUENCE CHARACTERISTICS:
        (A) LENGTH: 17 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 319:

Xaa Thr Arg Lys Ser Ser Arg Ser Asn Pro Arg Gly Arg Arg His Pro
1               5                   10                  15
Gly (2) INFORMATION FOR SEQ ID NO: 320:

(i) SEQUENCE CHARACTERISTICS:
        (A) LENGTH: 17 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 320:

Xaa Thr Arg Lys Ser Ser Arg Ser Asn Pro Arg Gly Arg Arg His Pro
1               5                   10                  15

Gly (2) INFORMATION FOR SEQ ID NO: 321:

(i) SEQUENCE CHARACTERISTICS:
        (A) LENGTH: 10 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 321:

Xaa Thr Asn Ala Lys His Ser Ser His Asn
1               5                   10

(2) INFORMATION FOR SEQ ID NO: 322:

(i) SEQUENCE CHARACTERISTICS:
        (A) LENGTH: 11 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 322:

Xaa Arg Arg Leu Arg Thr Arg Ser Arg Pro Asn
1               5                   10

(2) INFORMATION FOR SEQ ID NO: 323:

(i) SEQUENCE CHARACTERISTICS:
        (A) LENGTH: 9 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 323:

Xaa Arg Arg Leu Arg Thr Arg Ser Arg
1               5

(2) INFORMATION FOR SEQ ID NO: 324:

(i) SEQUENCE CHARACTERISTICS:
        (A) LENGTH: 7 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 324:

Xaa Arg Arg Leu Arg Thr Arg
 1               5

(2) INFORMATION FOR SEQ ID NO: 325:

(i) SEQUENCE CHARACTERISTICS:
        (A) LENGTH: 11 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 325:

Xaa Arg Arg Leu Arg Thr Arg Ser Arg Pro Asn
 1               5                   10

(2) INFORMATION FOR SEQ ID NO: 326:

(i) SEQUENCE CHARACTERISTICS:
        (A) LENGTH: 27 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 326:

Xaa Ser Asp His Ala Leu Gly Thr Asn Leu Arg Ser Asp Asn Ala Lys
 1               5                   10                  15

Glu Pro Gly Asp Tyr Asn Cys Cys Gly Asn Gly
                20                  25

(2) INFORMATION FOR SEQ ID NO: 327:

(i) SEQUENCE CHARACTERISTICS:
        (A) LENGTH: 28 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 327:

Xaa Gly Asp Tyr Asn Cys Cys Gly Asn Gly Asn Ser Thr Gly Arg Lys
 1               5                  10                  15

Val Phe Asn Arg Arg Arg Pro Ser Ala Ile Pro Thr
                20                  25

(2) INFORMATION FOR SEQ ID NO: 328:

(i) SEQUENCE CHARACTERISTICS:
        (A) LENGTH: 20 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 328:

Xaa Ser Asp His Ala Leu Gly Thr Asn Leu Arg Ser Asp Asn Ala Lys
 1               5                  10                  15

Glu Pro Gly Cys
                20

(2) INFORMATION FOR SEQ ID NO: 329:

(i) SEQUENCE CHARACTERISTICS:
        (A) LENGTH: 14 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 329:

Xaa Gly Asp Tyr Asn Cys Cys Gly Asn Gly Asn Ser Thr Gly
 1               5                  10

(2) INFORMATION FOR SEQ ID NO: 330:

(i) SEQUENCE CHARACTERISTICS:
        (A) LENGTH: 15 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 330:

Xaa Arg Lys Val Phe Asn Arg Arg Arg Pro Ser Ala Ile Pro Thr
 1               5                  10                  15

(2) INFORMATION FOR SEQ ID NO: 331:

(i) SEQUENCE CHARACTERISTICS:
        (A) LENGTH: 11 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 331:

Xaa Arg Lys Val Phe Asn Arg Arg Arg Pro Ser
1            5                  10

(2) INFORMATION FOR SEQ ID NO: 332:

(i) SEQUENCE CHARACTERISTICS:
        (A) LENGTH: 11 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 332:

Xaa Asn Arg Arg Arg Pro Ser Ala Ile Pro Thr
1            5                  10

(2) INFORMATION FOR SEQ ID NO: 333:

(i) SEQUENCE CHARACTERISTICS:
        (A) LENGTH: 7 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 333:

Xaa Asn Arg Arg Arg Pro Ser
1            5

(2) INFORMATION FOR SEQ ID NO: 334:

(i) SEQUENCE CHARACTERISTICS:
        (A) LENGTH: 40 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 334:

Ser Thr Pro Pro Ser Arg Glu Ala Tyr Ser Arg Pro Tyr Ser Val Asp
1            5                  10                  15

```
Ser Asp Ser Asp Thr Asn Ala Lys His Ser Ser His Asn Arg Arg Leu
            20                  25                  30

Arg Thr Arg Ser Arg Pro Asn Gly
            35                  40

(2) INFORMATION FOR SEQ ID NO: 335:

(i) SEQUENCE CHARACTERISTICS:
        (A) LENGTH: 44 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 335:

Ser Asp His Ala Leu Gly Thr Asn Leu Arg Ser Asp Asn Ala Lys Glu
 1               5                  10                  15

Pro Gly Asp Tyr Asn Cys Cys Gly Asn Gly Asn Ser Thr Gly Arg Lys
            20                  25                  30

Val Phe Asn Arg Arg Arg Pro Ser Ala Ile Pro Thr
            35                  40

(2) INFORMATION FOR SEQ ID NO: 336:

(i) SEQUENCE CHARACTERISTICS:
        (A) LENGTH: 30 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 336:

Xaa Ser Asp His Ala Leu Gly Thr Asn Leu Arg Ser Asp Asn Ala Lys
 1               5                  10                  15

Glu Pro Gly Asp Tyr Asn Cys Cys Gly Asn Gly Asn Ser Thr
            20                  25                  30

(2) INFORMATION FOR SEQ ID NO: 337:

(i) SEQUENCE CHARACTERISTICS:
        (A) LENGTH: 30 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 337:

Xaa Asn Leu Arg Ser Asp Asn Ala Lys Glu Pro Gly Asp Tyr Asn Cys
 1               5                  10                  15

Cys Gly Asn Gly Asn Ser Thr Gly Arg Lys Val Phe Asn Arg
            20                  25                  30
```

(2) INFORMATION FOR SEQ ID NO: 338:

(i) SEQUENCE CHARACTERISTICS:
        (A) LENGTH: 28 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 338:

Xaa Pro Gly Asp Tyr Asn Cys Cys Gly Asn Gly Asn Ser Thr Gly Arg
1               5                   10                  15

Lys Val Phe Asn Arg Arg Pro Ser Ala Ile Pro Thr
            20                  25

(2) INFORMATION FOR SEQ ID NO: 339:

(i) SEQUENCE CHARACTERISTICS:
        (A) LENGTH: 11 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 339:

Xaa Ala Ser His Asn Arg Arg Leu Arg Thr Arg
1               5                   10

(2) INFORMATION FOR SEQ ID NO: 340:

(i) SEQUENCE CHARACTERISTICS:
        (A) LENGTH: 11 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 340:

Xaa Ser Ala His Asn Arg Arg Leu Arg Thr Arg
1               5                   10

(2) INFORMATION FOR SEQ ID NO: 341:

(i) SEQUENCE CHARACTERISTICS:
        (A) LENGTH: 11 amino acids
        (B) TYPE: amino acid
        (C) STRANDEDNESS: single
        (D) TOPOLOGY: unknown

```
        (ii) MOLECULE TYPE: peptide (ix) FEATURE:
             (A) NAME/KEY: Other
             (B) LOCATION: 1...1
             (D) OTHER INFORMATION: Xaa=Lys(dns)

(xi) SEQUENCE DESCRIPTION: SEQ ID NO: 341:

Xaa Ser Ser Ala Asn Arg Arg Leu Arg Thr Arg
 1               5                  10

(2) INFORMATION FOR SEQ ID NO: 342:

(i) SEQUENCE CHARACTERISTICS:
             (A) LENGTH: 11 amino acids
             (B) TYPE: amino acid
             (C) STRANDEDNESS: single
             (D) TOPOLOGY: unknown (ii) MOLECULE TYPE: peptide (ix) FEATURE:
             (A) NAME/KEY: Other
             (B) LOCATION: 1...1
             (D) OTHER INFORMATION: Xaa=Lys(dns)

(xi) SEQUENCE DESCRIPTION: SEQ ID NO: 342:

Xaa Ser Ser His Ala Arg Arg Leu Arg Thr Arg
 1               5                  10

(2) INFORMATION FOR SEQ ID NO: 343:

(i) SEQUENCE CHARACTERISTICS:
             (A) LENGTH: 11 amino acids
             (B) TYPE: amino acid
             (C) STRANDEDNESS: single
             (D) TOPOLOGY: unknown (ii) MOLECULE TYPE: peptide (ix) FEATURE:
             (A) NAME/KEY: Other
             (B) LOCATION: 1...1
             (D) OTHER INFORMATION: Xaa=Lys(dns)

(xi) SEQUENCE DESCRIPTION: SEQ ID NO: 343:

Xaa Ser Ser His Asn Ala Arg Leu Arg Thr Arg
 1               5                  10

(2) INFORMATION FOR SEQ ID NO: 344:

(i) SEQUENCE CHARACTERISTICS:
             (A) LENGTH: 11 amino acids
             (B) TYPE: amino acid
             (C) STRANDEDNESS: single
             (D) TOPOLOGY: unknown (ii) MOLECULE TYPE: peptide (ix) FEATURE:
             (A) NAME/KEY: Other
             (B) LOCATION: 1...1
             (D) OTHER INFORMATION: Xaa=Lys(dns)

(xi) SEQUENCE DESCRIPTION: SEQ ID NO: 344:

Xaa Ser Ser His Asn Arg Ala Leu Arg Thr Arg
 1               5                  10
```

(2) INFORMATION FOR SEQ ID NO: 345:

(i) SEQUENCE CHARACTERISTICS:
        (A) LENGTH: 11 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 345:

Xaa Ser Ser His Asn Arg Arg Ala Arg Thr Arg
 1               5                  10

(2) INFORMATION FOR SEQ ID NO: 346:

(i) SEQUENCE CHARACTERISTICS:
        (A) LENGTH: 11 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 346:

Xaa Ser Ser His Asn Arg Arg Leu Ala Thr Arg
 1               5                  10

(2) INFORMATION FOR SEQ ID NO: 347:

(i) SEQUENCE CHARACTERISTICS:
        (A) LENGTH: 11 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 347:

Xaa Ser Ser His Asn Arg Arg Leu Arg Ala Arg
 1               5                  10

(2) INFORMATION FOR SEQ ID NO: 348:

(i) SEQUENCE CHARACTERISTICS:
        (A) LENGTH: 11 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 348:

Xaa Ser Ser His Asn Arg Arg Leu Arg Thr Ala
1               5                   10

(2) INFORMATION FOR SEQ ID NO: 349:

(i) SEQUENCE CHARACTERISTICS:
        (A) LENGTH: 10 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 349:

Ser Ser His Asn Arg Arg Leu Arg Thr Arg
1               5                   10

(2) INFORMATION FOR SEQ ID NO: 350:

(i) SEQUENCE CHARACTERISTICS:
        (A) LENGTH: 41 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 350:

Xaa Gly Arg Asn His Asp Val Val Ser Ser Asn Thr His Lys Ser Tyr
1               5                   10                  15

Arg Ser Pro Arg Ser Ala Ser Tyr Pro Arg Leu Ser Asn Asp Arg Thr
            20                  25                  30

Asp Arg Thr Glu Pro Ala Pro Ser Ser
        35                  40

(2) INFORMATION FOR SEQ ID NO: 351:

(i) SEQUENCE CHARACTERISTICS:
        (A) LENGTH: 20 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 351:

Xaa Arg Asn Thr Arg Asn Lys Thr Ser Arg Leu Ser Ala Asn Pro His
1               5                   10                  15

Arg Ser His Arg
        20

(2) INFORMATION FOR SEQ ID NO: 352:

(i) SEQUENCE CHARACTERISTICS:
       (A) LENGTH: 20 amino acids
       (B) TYPE: amino acid
       (C) STRANDEDNESS: single
       (D) TOPOLOGY: unknown (ii) MOLECULE TYPE: peptide (ix) FEATURE:
       (A) NAME/KEY: Other
       (B) LOCATION: 20...20
       (D) OTHER INFORMATION: Xaa=Lys(dns)

(xi) SEQUENCE DESCRIPTION: SEQ ID NO: 352:

Thr Asn Ala Lys His Ser Ser His Asn Arg Arg Leu Arg Thr Arg Ser
1               5                   10                  15

Arg Pro Asn Xaa
            20

(2) INFORMATION FOR SEQ ID NO: 353:

(i) SEQUENCE CHARACTERISTICS:
       (A) LENGTH: 10 amino acids
       (B) TYPE: amino acid
       (C) STRANDEDNESS: single
       (D) TOPOLOGY: unknown (ii) MOLECULE TYPE: peptide (ix) FEATURE:
       (A) NAME/KEY: Other
       (B) LOCATION: 10...10
       (D) OTHER INFORMATION: Xaa=Lys(dns)

(xi) SEQUENCE DESCRIPTION: SEQ ID NO: 353:

Arg Arg Leu Arg Thr Arg Ser Arg Lys Xaa
1               5                   10

(2) INFORMATION FOR SEQ ID NO: 354:

(i) SEQUENCE CHARACTERISTICS:
       (A) LENGTH: 21 amino acids
       (B) TYPE: amino acid
       (C) STRANDEDNESS: single
       (D) TOPOLOGY: unknown (ii) MOLECULE TYPE: peptide (ix) FEATURE:
       (A) NAME/KEY: Other
       (B) LOCATION: 1...1
       (D) OTHER INFORMATION: Xaa=Lys(dns)

(xi) SEQUENCE DESCRIPTION: SEQ ID NO: 354:

Xaa Ser Asp His Ala Leu Gly Thr Asn Leu Arg Ser Asp Asn Ala Lys
1               5                   10                  15

Glu Pro Gly Asp Tyr
            20

(2) INFORMATION FOR SEQ ID NO: 355:

(i) SEQUENCE CHARACTERISTICS:
       (A) LENGTH: 21 amino acids
       (B) TYPE: amino acid
       (C) STRANDEDNESS: single
       (D) TOPOLOGY: unknown

```
        (ii) MOLECULE TYPE: peptide (ix) FEATURE:
             (A) NAME/KEY: Other
             (B) LOCATION: 1...1
             (D) OTHER INFORMATION: Xaa=Lys(dns)

(xi) SEQUENCE DESCRIPTION: SEQ ID NO: 355:

Xaa Ser Asp Asn Ala Lys Glu Pro Gly Asp Tyr Asn Cys Cys Gly Asn
1               5                   10                  15

Gly Asn Ser Thr Gly
            20

(2) INFORMATION FOR SEQ ID NO: 356:

(i) SEQUENCE CHARACTERISTICS:
             (A) LENGTH: 16 amino acids
             (B) TYPE: amino acid
             (C) STRANDEDNESS: single
             (D) TOPOLOGY: unknown (ii) MOLECULE TYPE: peptide (ix) FEATURE:
             (A) NAME/KEY: Other
             (B) LOCATION: 1...1
             (D) OTHER INFORMATION: Xaa=Lys(dns)

(xi) SEQUENCE DESCRIPTION: SEQ ID NO: 356:

Xaa Ser Asp His Ala Leu Gly Thr Asn Leu Arg Ser Asp Asn Ala Lys
1               5                   10                  15

(2) INFORMATION FOR SEQ ID NO: 357:

(i) SEQUENCE CHARACTERISTICS:
             (A) LENGTH: 16 amino acids
             (B) TYPE: amino acid
             (C) STRANDEDNESS: single
             (D) TOPOLOGY: unknown (ii) MOLECULE TYPE: peptide (ix) FEATURE:
             (A) NAME/KEY: Other
             (B) LOCATION: 1...1
             (D) OTHER INFORMATION: Xaa=Lys(dns)

(xi) SEQUENCE DESCRIPTION: SEQ ID NO: 357:

Xaa Glu Pro Gly Asp Tyr Asn Cys Cys Gly Asn Gly Asn Ser Thr Gly
1               5                   10                  15

(2) INFORMATION FOR SEQ ID NO: 358:

(i) SEQUENCE CHARACTERISTICS:
             (A) LENGTH: 15 amino acids
             (B) TYPE: amino acid
             (C) STRANDEDNESS: single
             (D) TOPOLOGY: unknown (ii) MOLECULE TYPE: peptide (ix) FEATURE:
             (A) NAME/KEY: Other
             (B) LOCATION: 1...1
             (D) OTHER INFORMATION: Xaa=Lys(dns)

(xi) SEQUENCE DESCRIPTION: SEQ ID NO: 358:

Xaa Pro Gly Asp Tyr Asn Cys Cys Gly Asn Gly Asn Ser Thr Gly
1               5                   10                  15
```

(2) INFORMATION FOR SEQ ID NO: 359:

(i) SEQUENCE CHARACTERISTICS:
        (A) LENGTH: 11 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 359:

Xaa Pro Gly Asp Tyr Asn Cys Cys Gly Asn Gly
 1               5                   10

(2) INFORMATION FOR SEQ ID NO: 360:

(i) SEQUENCE CHARACTERISTICS:
        (A) LENGTH: 11 amino acids
        (B) TYPE: amino acid
        (C) STRANDEDNESS: single
        (D) TOPOLOGY: unknown (ii) MOLECULE TYPE: peptide (vi) ORIGINAL SOURCE:
        (A) ORGANISM: MEMORY
        (B) STRAIN: DISPLAY MEMORY (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 360:

Xaa Asn Cys Cys Gly Asn Gly Asn Ser Thr Gly
 1               5                   10

(2) INFORMATION FOR SEQ ID NO: 361:

(i) SEQUENCE CHARACTERISTICS:
        (A) LENGTH: 18 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 361:

Xaa Lys Thr Arg Lys Ser Ser Arg Ser Asn Pro Arg Gly Arg Arg His
 1               5                   10                  15

Pro Gly (2) INFORMATION FOR SEQ ID NO: 362:

(i) SEQUENCE CHARACTERISTICS:
        (A) LENGTH: 18 amino acids
        (B) TYPE: amino acid
        (C) STRANDEDNESS: single
        (D) TOPOLOGY: unknown (ii) MOLECULE TYPE: peptide (ix) FEATURE:
            (A) NAME/KEY: Other
            (B) LOCATION: 1...1
            (D) OTHER INFORMATION: Xaa=Lys(dns)

(xi) SEQUENCE DESCRIPTION: SEQ ID NO: 362:

Xaa Lys Thr Arg Lys Ser Ser Arg Ser Asn Pro Arg Gly Arg Arg His
1               5                   10                  15

Pro Gly (2) INFORMATION FOR SEQ ID NO: 363:

(i) SEQUENCE CHARACTERISTICS:
            (A) LENGTH: 17 amino acids
            (B) TYPE: amino acid
            (C) STRANDEDNESS: single
            (D) TOPOLOGY: unknown (ii) MOLECULE TYPE: peptide (ix) FEATURE:
            (A) NAME/KEY: Other
            (B) LOCATION: 1...1
            (D) OTHER INFORMATION: Xaa=Lys(dns)

(xi) SEQUENCE DESCRIPTION: SEQ ID NO: 363:

Xaa Lys Thr Asn Ala Lys His Ser Ser His Asn Arg Arg Leu Arg Thr
1               5                   10                  15

Arg (2) INFORMATION FOR SEQ ID NO: 364:

(i) SEQUENCE CHARACTERISTICS:
            (A) LENGTH: 16 amino acids
            (B) TYPE: amino acid
            (C) STRANDEDNESS: single
            (D) TOPOLOGY: unknown (ii) MOLECULE TYPE: peptide (ix) FEATURE:
            (A) NAME/KEY: Other
            (B) LOCATION: 1...1
            (D) OTHER INFORMATION: Xaa=Lys(dns)

(xi) SEQUENCE DESCRIPTION: SEQ ID NO: 364:

Xaa Thr Asn Ala Lys His Ser Ser Cys Asn Arg Arg Cys Arg Thr Arg
1               5                   10                  15

(2) INFORMATION FOR SEQ ID NO: 365:

(i) SEQUENCE CHARACTERISTICS:
            (A) LENGTH: 16 amino acids
            (B) TYPE: amino acid
            (C) STRANDEDNESS: single
            (D) TOPOLOGY: unknown (ii) MOLECULE TYPE: peptide (ix) FEATURE:
            (A) NAME/KEY: Other
            (B) LOCATION: 1...1
            (D) OTHER INFORMATION: Xaa=Lys(dns)

(xi) SEQUENCE DESCRIPTION: SEQ ID NO: 365:

Xaa Thr Asn Ala Lys His Ser Ser Cys Asn Arg Arg Leu Arg Cys Arg
1               5                   10                  15

```
(2) INFORMATION FOR SEQ ID NO: 366:

(i) SEQUENCE CHARACTERISTICS:
        (A) LENGTH: 16 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 366:

Xaa Ala Asn Ala Lys His Ser Ser His Asn Arg Arg Leu Arg Thr Arg
 1               5                  10                  15

(2) INFORMATION FOR SEQ ID NO: 367:

(i) SEQUENCE CHARACTERISTICS:
        (A) LENGTH: 16 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 367:

Xaa Thr Ala Ala Lys Asn Ser Ser His Asn Arg Arg Leu Arg Thr Arg
 1               5                  10                  15

(2) INFORMATION FOR SEQ ID NO: 368:

(i) SEQUENCE CHARACTERISTICS:
        (A) LENGTH: 16 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 368:

Xaa Thr Asn Gly Lys Asn Ser Ser His Asn Arg Arg Leu Arg Thr Arg
 1               5                  10                  15

(2) INFORMATION FOR SEQ ID NO: 369:

(i) SEQUENCE CHARACTERISTICS:
        (A) LENGTH: 16 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)
```

(xi) SEQUENCE DESCRIPTION: SEQ ID NO: 369:

Xaa Thr Asn Ala Lys Ala Ser Ser His Asn Arg Arg Leu Arg Thr Arg
1               5                   10                  15

(2) INFORMATION FOR SEQ ID NO: 370:

(i) SEQUENCE CHARACTERISTICS:
        (A) LENGTH: 16 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 370:

Xaa Thr Asn Ala Lys His Ala Ser His Asn Arg Arg Leu Arg Thr Arg
1               5                   10                  15

(2) INFORMATION FOR SEQ ID NO: 371:

(i) SEQUENCE CHARACTERISTICS:
        (A) LENGTH: 16 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 371:

Xaa Thr Asn Ala Lys His Ser Ala His Asn Arg Arg Leu Arg Thr Arg
1               5                   10                  15

(2) INFORMATION FOR SEQ ID NO: 372:

(i) SEQUENCE CHARACTERISTICS:
        (A) LENGTH: 16 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 372:

Xaa Thr Asn Ala Lys His Ser Ser Ala Asn Arg Arg Leu Arg Thr Arg
1               5                   10                  15

(2) INFORMATION FOR SEQ ID NO: 373:

(i) SEQUENCE CHARACTERISTICS:
        (A) LENGTH: 16 amino acids
        (B) TYPE: amino acid
        (C) STRANDEDNESS: single
        (D) TOPOLOGY: unknown

```
        (ii) MOLECULE TYPE: peptide (ix) FEATURE:
             (A) NAME/KEY: Other
             (B) LOCATION: 1...1
             (D) OTHER INFORMATION: Xaa=Lys(dns)

(xi) SEQUENCE DESCRIPTION: SEQ ID NO: 373:

Xaa Thr Asn Ala Lys His Ser Ser His Ala Arg Arg Leu Arg Thr Arg
 1               5                  10                  15

(2) INFORMATION FOR SEQ ID NO: 374:

(i) SEQUENCE CHARACTERISTICS:
             (A) LENGTH: 16 amino acids
             (B) TYPE: amino acid
             (C) STRANDEDNESS: single
             (D) TOPOLOGY: unknown (ii) MOLECULE TYPE: peptide (ix) FEATURE:
             (A) NAME/KEY: Other
             (B) LOCATION: 1...1
             (D) OTHER INFORMATION: Xaa=Lys(dns)

(xi) SEQUENCE DESCRIPTION: SEQ ID NO: 374:

Xaa Thr Asn Ala Lys His Ser Ser His Asn Ala Arg Leu Arg Thr Arg
 1               5                  10                  15

(2) INFORMATION FOR SEQ ID NO: 375:

(i) SEQUENCE CHARACTERISTICS:
             (A) LENGTH: 16 amino acids
             (B) TYPE: amino acid
             (C) STRANDEDNESS: single
             (D) TOPOLOGY: unknown (ii) MOLECULE TYPE: peptide (ix) FEATURE:
             (A) NAME/KEY: Other
             (B) LOCATION: 1...1
             (D) OTHER INFORMATION: Xaa=Lys(dns)

(xi) SEQUENCE DESCRIPTION: SEQ ID NO: 375:

Xaa Thr Asn Ala Lys His Ser Ser His Asn Arg Ala Leu Arg Thr Arg
 1               5                  10                  15

(2) INFORMATION FOR SEQ ID NO: 376:

(i) SEQUENCE CHARACTERISTICS:
             (A) LENGTH: 16 amino acids
             (B) TYPE: amino acid
             (C) STRANDEDNESS: single
             (D) TOPOLOGY: unknown (ii) MOLECULE TYPE: peptide (ix) FEATURE:
             (A) NAME/KEY: Other
             (B) LOCATION: 1...1
             (D) OTHER INFORMATION: Xaa=Lys(dns)

(xi) SEQUENCE DESCRIPTION: SEQ ID NO: 376:

Xaa Thr Asn Ala Lys His Ser Ser His Asn Arg Arg Ala Arg Thr Arg
 1               5                  10                  15
```

-continued

```
(2) INFORMATION FOR SEQ ID NO: 377:

(i) SEQUENCE CHARACTERISTICS:
        (A) LENGTH: 16 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 377:

Xaa Thr Asn Ala Lys His Ser Ser His Asn Arg Arg Leu Ala Thr Arg
 1               5                  10                  15

(2) INFORMATION FOR SEQ ID NO: 378:

(i) SEQUENCE CHARACTERISTICS:
        (A) LENGTH: 16 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 378:

Xaa Thr Asn Ala Lys His Ser Ser His Asn Arg Arg Leu Arg Ala Arg
 1               5                  10                  15

(2) INFORMATION FOR SEQ ID NO: 379:

(i) SEQUENCE CHARACTERISTICS:
        (A) LENGTH: 16 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 379:

Xaa Thr Asn Ala Lys His Ser Ser His Asn Arg Arg Leu Arg Thr Ala
 1               5                  10                  15

(2) INFORMATION FOR SEQ ID NO: 380:

(i) SEQUENCE CHARACTERISTICS:
        (A) LENGTH: 16 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)
```

(xi) SEQUENCE DESCRIPTION: SEQ ID NO: 380:

Xaa Thr Asn Ala Lys His Ser Ser His Asn Arg Arg Leu Arg Thr Arg
 1               5                  10                  15

(2) INFORMATION FOR SEQ ID NO: 381:

(i) SEQUENCE CHARACTERISTICS:
            (A) LENGTH: 17 amino acids
            (B) TYPE: amino acid
            (C) STRANDEDNESS: single
            (D) TOPOLOGY: unknown (ii) MOLECULE TYPE: peptide (ix) FEATURE:
            (A) NAME/KEY: Other
            (B) LOCATION: 1...1
            (D) OTHER INFORMATION: Xaa=Lys(dns)

(xi) SEQUENCE DESCRIPTION: SEQ ID NO: 381:

Xaa Lys Thr Asn Ala Lys His Ser Ser His Asn Arg Arg Leu Arg Thr
 1               5                  10                  15
Arg (2) INFORMATION FOR SEQ ID NO: 382:

(i) SEQUENCE CHARACTERISTICS:
            (A) LENGTH: 16 amino acids
            (B) TYPE: amino acid
            (C) STRANDEDNESS: single
            (D) TOPOLOGY: unknown (ii) MOLECULE TYPE: peptide (ix) FEATURE:
            (A) NAME/KEY: Other
            (B) LOCATION: 1...1
            (D) OTHER INFORMATION: Xaa=Lys(dns)

(xi) SEQUENCE DESCRIPTION: SEQ ID NO: 382:

Xaa Thr Asn Ala Lys His Ser Ser His Asn Arg Arg Leu Arg Thr Arg
 1               5                  10                  15

(2) INFORMATION FOR SEQ ID NO: 383:

(i) SEQUENCE CHARACTERISTICS:
            (A) LENGTH: 12 amino acids
            (B) TYPE: amino acid
            (C) STRANDEDNESS: single
            (D) TOPOLOGY: unknown (ii) MOLECULE TYPE: peptide (ix) FEATURE:
            (A) NAME/KEY: Other
            (B) LOCATION: 1...1
            (D) OTHER INFORMATION: Xaa=Lys(dns)

(xi) SEQUENCE DESCRIPTION: SEQ ID NO: 383:

Xaa Lys Ser Ser His Asn Arg Arg Leu Arg Thr Arg
 1               5                  10

(2) INFORMATION FOR SEQ ID NO: 384:

(i) SEQUENCE CHARACTERISTICS:
            (A) LENGTH: 12 amino acids
            (B) TYPE: amino acid
            (C) STRANDEDNESS: single
            (D) TOPOLOGY: unknown

```
    (ii) MOLECULE TYPE: peptide (ix) FEATURE:
         (A) NAME/KEY: Other
         (B) LOCATION: 1...1
         (D) OTHER INFORMATION: Xaa=Lys(dns)

(xi) SEQUENCE DESCRIPTION: SEQ ID NO: 384:

Xaa Lys Ser Ser His Asn Arg Arg Leu Arg Thr Arg
1               5                   10

(2) INFORMATION FOR SEQ ID NO: 385:

(i) SEQUENCE CHARACTERISTICS:
        (A) LENGTH: 12 amino acids
        (B) TYPE: amino acid
        (C) STRANDEDNESS: single
        (D) TOPOLOGY: unknown (ii) MOLECULE TYPE: peptide (ix) FEATURE:
         (A) NAME/KEY: Other
         (B) LOCATION: 1...1
         (D) OTHER INFORMATION: Xaa=Lys(dns)

(xi) SEQUENCE DESCRIPTION: SEQ ID NO: 385:

Xaa Lys Thr Asn Ala Lys His Ser Ser His Asn Arg
1               5                   10

(2) INFORMATION FOR SEQ ID NO: 386:

(i) SEQUENCE CHARACTERISTICS:
        (A) LENGTH: 12 amino acids
        (B) TYPE: amino acid
        (C) STRANDEDNESS: single
        (D) TOPOLOGY: unknown (ii) MOLECULE TYPE: peptide (ix) FEATURE:
         (A) NAME/KEY: Other
         (B) LOCATION: 1...1
         (D) OTHER INFORMATION: Xaa=Lys(dns)

(xi) SEQUENCE DESCRIPTION: SEQ ID NO: 386:

Xaa Lys Thr Asn Ala Lys His Ser Ser His Asn Arg
1               5                   10

(2) INFORMATION FOR SEQ ID NO: 387:

(i) SEQUENCE CHARACTERISTICS:
        (A) LENGTH: 16 amino acids
        (B) TYPE: amino acid
        (C) STRANDEDNESS: single
        (D) TOPOLOGY: unknown (ii) MOLECULE TYPE: peptide (ix) FEATURE:
         (A) NAME/KEY: Other
         (B) LOCATION: 1...1
         (D) OTHER INFORMATION: Xaa=Lys(dns)

(xi) SEQUENCE DESCRIPTION: SEQ ID NO: 387:

Xaa Thr Asn Ala Lys His Ser Ser His Asn Arg Arg Leu Arg Thr Arg
1               5                   10                  15
```

-continued

```
(2) INFORMATION FOR SEQ ID NO: 388:

(i) SEQUENCE CHARACTERISTICS:
        (A) LENGTH: 15 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 388:

Xaa Ala Gly Asp Tyr Asn Cys Cys Gly Asn Gly Asn Ser Thr Gly
 1               5                  10                  15

(2) INFORMATION FOR SEQ ID NO: 389:

(i) SEQUENCE CHARACTERISTICS:
        (A) LENGTH: 15 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 389:

Xaa Pro Ala Asp Tyr Asn Cys Cys Gly Asn Gly Asn Ser Thr Gly
 1               5                  10                  15

(2) INFORMATION FOR SEQ ID NO: 390:

(i) SEQUENCE CHARACTERISTICS:
        (A) LENGTH: 15 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 390:

Xaa Pro Gly Ala Tyr Asn Cys Cys Gly Asn Gly Asn Ser Thr Gly
 1               5                  10                  15

(2) INFORMATION FOR SEQ ID NO: 391:

(i) SEQUENCE CHARACTERISTICS:
        (A) LENGTH: 15 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)
```

(xi) SEQUENCE DESCRIPTION: SEQ ID NO: 391:

Xaa Pro Gly Asp Ala Asn Cys Cys Gly Asn Gly Asn Ser Thr Gly
 1               5                  10                  15

(2) INFORMATION FOR SEQ ID NO: 392:

(i) SEQUENCE CHARACTERISTICS:
        (A) LENGTH: 15 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 392:

Xaa Pro Gly Asp Tyr Ala Cys Cys Gly Asn Gly Asn Ser Thr Gly
 1               5                  10                  15

(2) INFORMATION FOR SEQ ID NO: 393:

(i) SEQUENCE CHARACTERISTICS:
        (A) LENGTH: 15 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 393:

Xaa Pro Gly Asp Tyr Asn Ala Cys Gly Asn Gly Asn Ser Thr Gly
 1               5                  10                  15

(2) INFORMATION FOR SEQ ID NO: 394:

(i) SEQUENCE CHARACTERISTICS:
        (A) LENGTH: 15 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 394:

Xaa Pro Gly Asp Tyr Asn Cys Ala Gly Asn Gly Asn Ser Thr Gly
 1               5                  10                  15

(2) INFORMATION FOR SEQ ID NO: 395:

(i) SEQUENCE CHARACTERISTICS:
        (A) LENGTH: 15 amino acids
        (B) TYPE: amino acid
        (C) STRANDEDNESS: single
        (D) TOPOLOGY: unknown

```
    (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 395:

Xaa Pro Gly Asp Tyr Asn Cys Cys Ala Asn Gly Asn Ser Thr Gly
 1               5                  10                  15

(2) INFORMATION FOR SEQ ID NO: 396:

(i) SEQUENCE CHARACTERISTICS:
        (A) LENGTH: 15 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 396:

Xaa Pro Gly Asp Tyr Asn Cys Cys Gly Ala Gly Asn Ser Thr Gly
 1               5                  10                  15

(2) INFORMATION FOR SEQ ID NO: 397:

(i) SEQUENCE CHARACTERISTICS:
        (A) LENGTH: 15 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 397:

Xaa Pro Gly Asp Tyr Asn Cys Cys Gly Asn Ala Asn Ser Thr Gly
 1               5                  10                  15

(2) INFORMATION FOR SEQ ID NO: 398:

(i) SEQUENCE CHARACTERISTICS:
        (A) LENGTH: 15 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 398:

Xaa Pro Gly Asp Tyr Asn Cys Cys Gly Asn Gly Ala Ser Thr Gly
 1               5                  10                  15
```

(2) INFORMATION FOR SEQ ID NO: 399:

(i) SEQUENCE CHARACTERISTICS:
       (A) LENGTH: 15 amino acids
       (B) TYPE: amino acid
       (C) STRANDEDNESS: single
       (D) TOPOLOGY: unknown (ii) MOLECULE TYPE: peptide (ix) FEATURE:
       (A) NAME/KEY: Other
       (B) LOCATION: 1...1
       (D) OTHER INFORMATION: Xaa=Lys(dns)

(xi) SEQUENCE DESCRIPTION: SEQ ID NO: 399:

Xaa Pro Gly Asp Tyr Asn Cys Cys Gly Asn Gly Asn Ala Thr Gly
1               5                   10                  15

(2) INFORMATION FOR SEQ ID NO: 400:

(i) SEQUENCE CHARACTERISTICS:
       (A) LENGTH: 15 amino acids
       (B) TYPE: amino acid
       (C) STRANDEDNESS: single
       (D) TOPOLOGY: unknown (ii) MOLECULE TYPE: peptide (ix) FEATURE:
       (A) NAME/KEY: Other
       (B) LOCATION: 1...1
       (D) OTHER INFORMATION: Xaa=Lys(dns)

(xi) SEQUENCE DESCRIPTION: SEQ ID NO: 400:

Xaa Pro Gly Asp Tyr Asn Cys Cys Gly Asn Gly Asn Ser Ala Gly
1               5                   10                  15

(2) INFORMATION FOR SEQ ID NO: 401:

(i) SEQUENCE CHARACTERISTICS:
       (A) LENGTH: 15 amino acids
       (B) TYPE: amino acid
       (C) STRANDEDNESS: single
       (D) TOPOLOGY: unknown (ii) MOLECULE TYPE: peptide (ix) FEATURE:
       (A) NAME/KEY: Other
       (B) LOCATION: 1...1
       (D) OTHER INFORMATION: Xaa=Lys(dns)

(xi) SEQUENCE DESCRIPTION: SEQ ID NO: 401:

Xaa Pro Gly Asp Tyr Asn Cys Cys Gly Asn Gly Asn Ser Thr Ala
1               5                   10                  15

(2) INFORMATION FOR SEQ ID NO: 402:

(i) SEQUENCE CHARACTERISTICS:
       (A) LENGTH: 15 amino acids
       (B) TYPE: amino acid
       (C) STRANDEDNESS: single
       (D) TOPOLOGY: unknown (ii) MOLECULE TYPE: peptide (xi) SEQUENCE DESCRIPTION: SEQ ID NO: 402:

Thr Asn Ala Lys His Ser Ser His Asn Arg Arg Leu Arg Thr Arg
1               5                   10                  15

(2) INFORMATION FOR SEQ ID NO: 403:

(i) SEQUENCE CHARACTERISTICS:
       (A) LENGTH: 14 amino acids
       (B) TYPE: amino acid
       (C) STRANDEDNESS: single
       (D) TOPOLOGY: unknown (ii) MOLECULE TYPE: peptide (xi) SEQUENCE DESCRIPTION: SEQ ID NO: 403:

Pro Gly Asp Tyr Asn Cys Cys Gly Asn Cys Asn Ser Thr Gly
1               5                  10

(2) INFORMATION FOR SEQ ID NO: 404:

(i) SEQUENCE CHARACTERISTICS:
       (A) LENGTH: 40 amino acids
       (B) TYPE: amino acid
       (C) STRANDEDNESS: <Unknown>
       (D) TOPOLOGY: unknown (ii) MOLECULE TYPE: peptide (xi) SEQUENCE DESCRIPTION: SEQ ID NO: 404:

Ser Ala Arg Asp Ser Gly Pro Ala Glu Asp Gly Ser Arg Ala Val Arg
1               5                  10                  15

Leu Asn Gly Val Glu Asn Ala Asn Thr Arg Lys Ser Ser Arg Ser Asn
            20                  25                  30

Pro Arg Gly Arg Arg His Pro Gly
        35                  40

(2) INFORMATION FOR SEQ ID NO: 405:

(i) SEQUENCE CHARACTERISTICS:
       (A) LENGTH: 19 amino acids
       (B) TYPE: amino acid
       (C) STRANDEDNESS: <Unknown>
       (D) TOPOLOGY: unknown (ii) MOLECULE TYPE: peptide (xi) SEQUENCE DESCRIPTION: SEQ ID NO: 405:

Gly Thr Arg Asn Ser His Gly Cys Ile Thr Arg Pro Leu Arg Gln Ala
1               5                  10                  15

Ser Ala His (2) INFORMATION FOR SEQ ID NO: 406:

(i) SEQUENCE CHARACTERISTICS:
       (A) LENGTH: 21 amino acids
       (B) TYPE: amino acid
       (C) STRANDEDNESS: <Unknown>
       (D) TOPOLOGY: unknown (ii) MOLECULE TYPE: peptide (ix) FEATURE:
       (A) NAME/KEY: Other
       (B) LOCATION: 1...1
       (D) OTHER INFORMATION: Xaa=Lys(dns)

(xi) SEQUENCE DESCRIPTION: SEQ ID NO: 406:

Xaa Arg Val Gly Gln Cys Thr Asp Ser Asp Val Arg Arg Pro Trp Ala
1               5                  10                  15

Arg Ser Cys Ala His
            20

```
(2) INFORMATION FOR SEQ ID NO: 407:

(i) SEQUENCE CHARACTERISTICS:
        (A) LENGTH: 23 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Other
        (B) LOCATION: 1...1
        (D) OTHER INFORMATION: Xaa=Lys(dns)

(xi) SEQUENCE DESCRIPTION: SEQ ID NO: 407:

Xaa Cys Gly Ala Gly Thr Arg Asn Ser His Gly Cys Ile Thr Arg Pro
 1               5                  10                  15

Leu Arg Gln Ala Ser Ala His
                20
```